US008183039B2

(12) United States Patent
Schmitz et al.

(10) Patent No.: US 8,183,039 B2
(45) Date of Patent: May 22, 2012

(54) METHOD FOR ISOLATING BDCA-4+ DENDRITIC CELLS

(75) Inventors: Juergen Schmitz, Bergheim (DE); David William Buck, Sussex (GB); Andrzej Dzionek, Cologne (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 1014 days.

(21) Appl. No.: 11/393,155

(22) Filed: Mar. 29, 2006

(65) Prior Publication Data

US 2006/0233840 A1     Oct. 19, 2006

Related U.S. Application Data

(63) Continuation of application No. 09/714,712, filed on Nov. 15, 2000, now Pat. No. 7,030,228.

(60) Provisional application No. 60/197,205, filed on Apr. 13, 2000, provisional application No. 60/196,824, filed on Apr. 11, 2000, provisional application No. 60/180,775, filed on Feb. 7, 2000, provisional application No. 60/179,003, filed on Jan. 28, 2000, provisional application No. 60/167,076, filed on Nov. 23, 1999, provisional application No. 60/165,555, filed on Nov. 15, 1999.

(51) Int. Cl.
*C12N 5/00* (2006.01)
*C12N 5/02* (2006.01)
*C07K 1/00* (2006.01)
*C12Q 1/24* (2006.01)

(52) U.S. Cl. ............................ 435/325; 435/372; 435/30

(58) Field of Classification Search ........................ None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,683,202 A | 7/1987 | Mullis |
| 4,754,065 A | 6/1988 | Levenson et al. |
| 4,800,159 A | 1/1989 | Mullis et al. |
| 5,625,126 A | 4/1997 | Lonberg et al. |
| 5,643,786 A | 7/1997 | Cohen et al. |
| 5,750,119 A | 5/1998 | Srivastava |
| 5,788,963 A | 8/1998 | Murphy et al. |
| 5,789,650 A | 8/1998 | Lonberg et al. |
| 5,876,917 A | 3/1999 | Hart |
| 5,972,627 A | 10/1999 | Galy |
| 5,985,660 A | 11/1999 | Galy |
| 5,994,126 A | 11/1999 | Inaba et al. |
| 6,004,807 A | 12/1999 | Banchereau et al. |
| 6,008,004 A | 12/1999 | Olweus et al. |
| 6,010,905 A | 1/2000 | Cohen et al. |
| 6,015,554 A | 1/2000 | Galy |
| 6,017,527 A | 1/2000 | Maraskovsky et al. |
| 6,046,158 A | 4/2000 | Ariizumi et al. |
| 6,255,458 B1 | 7/2001 | Lonberg et al. |
| 6,300,129 B1 | 10/2001 | Lonberg et al. |

FOREIGN PATENT DOCUMENTS

| | | |
|---|---|---|
| EP | 0329400 | 9/1993 |
| EP | 922758 | 6/1999 |
| WO | WO91/13632 | 9/1991 |
| WO | WO93/07286 | 4/1993 |
| WO | WO93/20185 | 10/1993 |
| WO | WO95/12409 | 5/1995 |
| WO | WO96/07097 | 3/1996 |
| WO | WO96/10411 | 4/1996 |
| WO | WO96/28732 | 9/1996 |
| WO | WO97/02342 | 1/1997 |
| WO | WO97/03186 | 1/1997 |
| WO | WO97/06821 | 2/1997 |
| WO | WO97/10000 | 3/1997 |
| WO | WO97/10001 | 3/1997 |
| WO | WO97/24447 | 7/1997 |
| WO | WO97/29182 | 8/1997 |
| WO | WO98/14561 | 4/1998 |
| WO | WO98/15579 | 4/1998 |
| WO | WO98/23735 | 6/1998 |
| WO | WO 98/28332 | 7/1998 |
| WO | WO98/28332 | 7/1998 |
| WO | WO98/34641 | 8/1998 |
| WO | WO98/34642 | 8/1998 |
| WO | WO98/46785 | 10/1998 |
| WO | WO99/02562 | 3/1999 |
| WO | WO 99/21997 | 5/1999 |
| WO | WO99/43350 | 9/1999 |
| WO | WO99/47646 | 9/1999 |
| WO | WO99/57266 | 11/1999 |
| WO | WO99/63050 | 12/1999 |
| WO | WO00/06588 | 2/2000 |
| WO | WO00/08191 | 2/2000 |
| WO | WO00/09151 | 2/2000 |
| WO | WO00/18803 | 4/2000 |
| WO | WO00/35949 | 6/2000 |
| WO | WO 01/72773 | 10/2001 |

OTHER PUBLICATIONS

Reza et al., "Neuropilin-1 is expressed on adult mammalian dorsal root ganglion neurons and mediates semaphorin3a/collapsin-1-induced growth cone collapse by small diameter sensory afferents", Molecular and Cellular Neuroscience, 14(4-5):317-326, (1999).
Dzionek et al., 2002, "Plasmacytoid dendritic cells: from specific surface markers to specific cellular functions" *Hum Immunol.* 63(12):1133-48.
Zola et al. Leukocyte and Stromal Cell Molecules: The CD Markers, 2007, John Wiley & Sons, Inc. Hoboken, New Jersey, pp. 486-487.
O'Doherty et al. (1993) "Tolerizing mice to human leukocytes: a step toward the production of monoclonal antibodies specific for human dendritic cells" Adv. Exp. Med. Biol. 329:165-72.
Facchetti et al. (1998) "Plasmacytoid T cells. Immunohistochemical evidence for their monocyte/macrophage origin" Am. J. Pathol. 133:15-21.

(Continued)

*Primary Examiner* — Gerald R Ewoldt
(74) *Attorney, Agent, or Firm* — Kilpatrick Townsend & Stockton LLP

(57) ABSTRACT

The application describes, inter alia, a method for isolating or enriching for dendritic cells from a mixture of human cells involving contacting cells in the mixture with an antibody that binds BDCA-4, or antigen-binding fragment thereof, under conditions in which the antibody or antigen-binding fragment binds BDCA-4+ dendritic cells, and separating dendritic cells bound by the antibody or antigen-binding fragment from other cells in the mixture.

17 Claims, 19 Drawing Sheets

OTHER PUBLICATIONS

Brugger et al. (1999) "Approaches to dendritic cell-based immunotherapy after peripheral blood stem cell transplantation" Ann. N.Y. Acad. Sci. 872:363-71.

Picker et al. (1992) "Physiological and molecular mechanisms of lymphocyte homing" Annu. Rev. Immunol. 10:561-91.

Wolff et al. (1984) "The use of monoclonal anti-Thy1 IgG1 for the targeting of liposomes to AKR-A cells in vitro and in vivo" Biochim. Biophys. Acta 802:259-73.

Nederman et al. (1990) "An in vitro bioassay for quantitation of human interferons by measurements of antiproliferative activity on a continuous human lymphoma cell line" Biologicals 18:29-34.

Cockett et al. (1990) "High Level Expression of Tissue Inhibitor of Metalloproteinases in Chinese Hamster Ovary Cells using Glutamine Synthetase Gene Amplification". Bio/Technology 8:662-667.

Tempest et al. (1991) "Reshaping a human monoclonal antibody to inhibit human respiratory syncytial virus infection in vivo" Biotechnol. 9:266-71.

Fiedler et al. (1995) "High-level production and long-term storage of engineered antibodies in transgenic tobacco seeds" Biotechnol. 13:1090-3.

Maiti et at (19g7) "Development and characterization of Pancarcinoma specific Human Monoclonal Antibody H11 (NovoMAb- G2)" Biotechnol. Int. 1:85-93.

LeBien et al. (1989) "The common acute lymphoblastic leukemia antigen (CD0)-emancipation from a functional enigma" Blood 73:625-635.

Uckunet et al. (1990) "Regulation of human B-cell ontogeny" Blood 76:1908-23.

Terstappen et at (1991) "Sequential Generations of hematopoietic colonies derived from single nonlineage committed CD34+CD38 progenitor cells" Blood 77:1218-1227.

Terstappen et al. (1992) "Flow cytometric assessment of human T-cell differentiation in thymus and bone marrow" Blood 79:666-77.

Bregni et at (1992) "Human peripheral blood hematopoietic progenitors are optimal targets of retroviral-mediated gene transfer" Blood 80:1418-1422.

van Noesel et at (1993) "Architecture of human B cell antigen receptors" Blood 82:363-73.

Barcena et al. (1993) "Phenotypic and functional analysis of T-cell precursors in the human fetal liver and thymus: CD7 expression in the early stages of T- and myeloid-cell development" Blood 82:3401-14.

Galy et al. (1994) "Generation of T cells from cytokine-mobilized peripheral blood and adult bone marrow CD34+ cells" Blood 84:104-10.

Mackensen et at (1995) "Delineation of the dendritic cell lineage by generating large numbers of Birbeck granule-positive Langerhans cells from human peripheral blood progenitor cells in vitro" Blood 86:2699-707.

Strunk et al. (1996) "Generation of human dendritic cells/Langerhans cells from circulating CD34+ hematopoietic progenitor cells" Blood 87:1292-302.

Herbst et al. (1996) "In vitro differentiation of CD34+ hematopoietic progenitor cells toward distinct dendritic cell subsets of the Birbeck granule and MIIC-positive Langerhans cell and the interdigitating dendritic cell type" Blood 88:2541-8.

Yin et al. (1997) "AC133, a novel marker for human hematopoietic stem and progenitor cells" Blood 90:5002-12.

Fearnley et al. (1997) "Isolation of human blood dendritic cells using the CMRF-44 monoclonal antibody: implications for studies on antigen-presenting cell function and immunotherapy" Blood 89:3708-16.

Gabrilovich et al. (1998) "Vascular endothelial growth factor inhibits the development of dendritic cells and dramatically affects the differentiation of multiple hematopoietic lineages in vivo" Blood 92:4150-66.

Avigan (1999) "Dendritic cells: development, function and potential use for cancer immunotherapy" Blood Rev. 13:51-64.

Fearnley et al. (1999) "Monitoring human blood dendritic cell numbers in normal individuals and in stem cell transplantation" Blood 93:728-36.

Sorg et al. (1999) "Identification of cord blood dendritic cells as an immature CD11c-population" Blood 93:2302-7.

Gilboa et al. (1998) "Immunotherapy of cancer with dendritic-cell-based vaccines" Cancer Immunol. Immunother. 46:82-87.

Rabinowich et al. (1987) "Functional analysis of mononuclear cells infiltrating into tumors: lysis of autologous human tumor cells by cultured infiltrating lymphocytes" Cancer Res. 47:173-177.

Henderikx et al. (1998) "Human single-chain Fv antibodies to MUC1 core peptide selected from phage display libraries recognize unique epitopes and predominantly bind adenocarcinoma" Canc. Res. 58:4324-32.

Watson et al. (1998) "The recirculation of naive and memory lymphocytes" Cell Adhes. Commun. 6:105-10.

Vallin et al. (1999) "Patients with systemic lupus erythematosus (SLE) have a circulating inducer of interferon-α (IFN-α) production acting on leukocytes resembling immature dendritic cells" Clin. Exp. Immunol. 115:196-202.

Bradley et al. (1996) "Lymphocyte migration into tissue: the paradigm derived from CD4 subsets" Curr. Opin. Immunol. 8:312-20.

Tarlinton (1998) "Germinal centers: Form and function" Curr. Opin. Immunol. 10:245-251.

He et al. (1997) "Neuropilin is a receptor for the axonal chemorepellent Semaphorin III" Cell 90:739-51.

Kolodkin et al. (1997) "Neuropilin is a semaphorin III receptor" Cell 90:753-62.

Young et al. (1988) "Accessory Cell Requirements for the Mixed-Leukocyte Reaction and Polyclonal Mitogens, as Studied with a New Technique for Enriching Blood Dendritic Cells" Cell Immunol. 111:167.

Gabrilovich et al. (1999) "Antibodies to Vascular Endothelial Growth Factor Enhance the Efficacy of Cancer Immunotherapy by Improving Endogenous Dendritic Cell Function" Clin. Cancer Res. 5:2963-2970.

Weissman et al. (1997) "Role of Dendritic Cells in Immunopathogenesis of Human Immunodeficiency Virus Infection" Clin. Microbial. Rev. 10:358-367.

Austyn (1998) "Dendritic Cells" Curr. Opin. Hematol. 5:3-15.

Fernandez et al. (1998) "Active specific T-cell-based immunotherapy for cancer: nucleic acids, peptides, whole native proteins, recombinant viruses, with dendritic cells adjuvants or whole tumor cell-based vaccines. Principles and future prospects" Cyto. Cell. Mol. Ther. 4:53-65.

Miltenyti et al. (1990) "High Gradient Magnetic Cell Separation With MACS" Cytometry 11:231-238.

Kuhn et al. (1997) "Current Status of Melanoma Vaccines" Dermatol. Surg. 23:649-54.

Nissim et al. (1994) "Antibody fragments from a 'single pot' phage display library as immunochemical reagents" EMBO J. 13:692-698.

Valitutti et al. (1993) "Role of cAMP in regulating cytotoxic T lymphocyte adhesion and motility" Eur. J. Immunol. 23:790-795.

Heufler et al. (1996) "IL12 is produced by dendritic cells and mediates T helper1 development as well as interferon-γ production by T helper1 cells" Eur. J. Immunol. 26:659-68.

Parronchi et al. (1996) "Effects of interferon-α on cytokine profile, T cell receptor repertoire and peptide reactivity of human allergen-specific T cells" Eur. J. Immunol. 26:697-703.

Robinson et al. (1999) "Human peripheral blood contains two distinct lineages of dendritic cells" Eur. J. Immunol. 29:2769-2778.

Xu et al. (1994) "Correction of the enzyme deficiency in hematopoietic cells of Gaucher patients using a clinically acceptable retroviral supernatant transduction protocol" Exp. Hematol. 22:223-230.

Wan et al. (1997) "Dendritic Cells Transduced with an Adenoviral Vector Encoding a Model Tumor-Associated Antigen for Tumor Vaccination" Hum. Gene Ther. 8:1355-63.

Douillard et al. (1986) "Monoclonal Antibodies Specific Immunotherapy of Gastrointestinal Tumors" Hybridomas (Supp.) 1:5139.

Smith et al. (1997) "Oncogenic mutations in *ras* create HLA-A2.1 binding peptides but affect their extracellular antigen processing" Int. Immunol. 9:1085-93.

O'Doherty et al. (1994) "Human blood contains two subsets of dendritic cells, one immunologically mature and the other immature" Immunol. 82:487-493.

Hock et al. (1994) "Characterization of CMRF-44 a novel monoclonal antibody to an activation antigen expressed by the allostimulatory cells within peripheral blood, including dendritic cells" Immunol. 83:573-581.

Godfrey and Zlotnik (1993) "Control points in early T-cell development" Immunol. Today 14:547-553.

Ibrahim et al. (1995) "The injured cell: the role of the dendritic cell system as a sentinel receptor pathway" Immunol. Today 16:181-186.

Scollay et al. (1986) "Dynamics of Early T Cells: Prothymocyte Migration and Proliferation in the Adult Mouse Thymus" Immunol. Rev. 91:129-157.

Kearney et al. (1994) "Visualization of Peptide-Specific T Cell Immunity and Peripheral Tolerance Induction In Vivo" Immunity 1:327-339.

Valladeau et al. (2000) "Langerin, a novel C-type lectin specific to Langerhans cells, is an endocytic receptor that induces the formation of Birbeck granules" Immunity 12:71-81.

Hoogenboom et al. (1998) "Antibody phage display technology and its applications" Immunotechnol. 4:1-20.

Posnett et al. (1988) "A Novel Method for Producing Anti-peptide Antibodies" J. Biol. Chem. 263:1719-1725.

Rosok et al. (1996) "A Combinatorial Library Strategy for the Rapid Humanization of Anticarcinoma BR96 Fab" J. Biol. Chem. 271:22611-22618.

Baca et al. (1997) "Antibody Humanization Using Monovalent Phage Display" J. Biol. Chem. 272:10678-10684.

Ariizumi et al. (2000) "Cloning of a Second Dendritic Cell-associated C-type Lectin (Dectin-2) and Its Alternatively Spliced Isoforms" J. Biol. Chem. 16:11957.

Zoeteweij et al. (1998) "HIV-Dendritic Cell Interactions Promote Efficient Viral Infection of T Cells" J. Biomed. Sci. 5:253-259.

Hughes et al. (1992) "Retroviral Gene Transfer to Primitive Normal and Leukemic Hematopoietic Cells Using Clinically Applicable Procedures" J. Clin. Invest. 89:1817.

Van Voorhis et al. (1982) "Human Dendritic Cells: Enrichment and Characterization from Peripheral Blood" J. Exp. Med. 155:1172.

Lanzavecchia et al. (1988) "Antibodies as Antigens: The use of Mouse Monoclonal Antibodies to Focus Human T Cells against Selected Targets" J. Exp. Med. 167:345-352.

Peault et al. (1991) "Lymphoid Reconstitution of the Human Fetal Thymus in SCID Mice with CD34$^+$Precursor Cells" J. Exp. Med. 174:1283-1286.

Jacob et al. (1992) "In Situ Studies of the Primary Immune Response to (4-hydroxy-3-nitrophenyl)acetyl. II. A Common Clonal Origin for Periarteriolar Lymphoid Sheath-associated Foci and Germinal Centers" J. Exp. Med. 176:679-687.

Galy et al. (1993) "Precursors of CD3$^+$CD4$^+$CD8$^+$Cells in the Human Thymus Are Defined by Expression of CD34. Delineation of Early Events in Human Thymic Development" J. Exp. Med. 178:391-401.

Li et al. (1993) "The Regulated Expression of B Lineage Associated Genes during B Cell Differentiation in Bone Marrow and Fetal Liver" J. Exp. Med. 178:951-960.

O'Doherty et al. (1993) "Dendritic Cells Freshly Isolated from Human Blood Express CD4 and Mature into Typical Immunostimulatory Dendritic Cells after Culture in Monocyte-Conditioned Medium" J. Exp. Med. 178:1067-1076.

Sanchez et al. (1993) "Human Natural Killer Cell Committed Thymocytes and Their Relation to the T Cell Lineage" J. Exp. Med. 178:1857-1866.

Sallusto et al. (1994) "Efficient presentation of soluble antigen by cultured human dendritic cells is maintained by granulocyte/macrophage colony-stimulating factor plus Interleukin 4 and downregulated by tumor necrosis factor α" J. Exp. Med. 179:1109-1118.

Romani et al. (1994) "Proliferating Dendritic Cell Progenitors in Human Blood" J. Exp. Med. 180:83-93.

Nijman et al. (1995) "Antigen Capture and Major Histocompatibility Class II Compartments of Freshly Isolated and Cultured Human Blood Dendritic Cells", J. Exp. Med. 182:163-174.

Sallusto et al. (1995) "Dendritic Cells Use Macropinocytosis and the Mannose Receptor to Concentrate Macromolecules in the Major Histocompatibility Complex Class II Compartment: Downregulation by Cytokines and Bacterial Products" J. Exp. Med. 182:389-400.

Bruno et al. (1997) "Identification of a Committed T Cell Precursor Population in Adult Human Peripheral Blood" J. Exp. Med. 185:875-884.

Grouard et al. (1997) "The Enigmatic Plasmacytoid T Cells Develop into Dendritic Cells with Interleukin (IL)-3 and CD40-Ligand" J. Exp. Med. 185:1101-1111.

Robert et al. (1999) "Interaction of Dendritic Cells with Skin Endothelium: A New Perspective on Immunosurveillance" J. Exp. Med. 189:627-636.

Sallusto et al. (1998) "Rapid and coordinated switch in chemokine receptor expression during dendritic cell maturation" Eur. J. Immunol. 28:2760-9.

Mannering et al. (1988) "Optimisation of the conditions for generating human DC initiated antigen specific T lymphocyte lines in vitro" J. Immunol. Met. 219:69-83.

Zhou et al. (1992) "A Novel Cell-Surface Molecule Expressed By Human Interdigitating Reticulum Cells, Langerhans Cells, and activated Lymphocytes is a New Member bf the Ig Superfamily" J. Immunol. 149:735-742.

Glaser et al. (1992) "Dissection of the Combining Site in A Humanized Anti-Tac Antibody" J. Immunol. 149:2606.

Thomas et al. (1993) "Isolation and Characterization of Human Peripheral Blood Dendritic Cells" J. Immunol. 150:821-834.

Ferbas et al. (1994) "CD4+ Blood Dendritic Cells Are Potent Producers of IFN-α in Response to in vitro HIV-1 Infection" Immunol. 152:4649-4662.

Thomas et al. (1994) "Human peripheral blood dendritic cell subsets" J. Immunol. 153:4016-4028.

Zhou et al. (1995) "Human Blood Dendritic Cells Selectively Express CD83, A Member of the Immunoglobulin Superfamily" J. Immunol. 154:3821-3835.

Szabolcs et al. (1995) "Expansion of immunostimulatory dendritic cells among the myeloid progeny of human CD34$^+$bone marrow precursors cultured with c-kit ligand, GM-CSF, and TNF-α$^{1,2}$ " Immunol. 154:5851-5861.

Fanger et al. (1996) "Type I (CD64) and Type II (CD32) Fcγ Receptor-Mediated Phagocytosis by Human Blood Dendritic Cells" J. Immunol. 157:541-548.

Maurer et al. (1996) "Peripheral Blood Dendritic Cells EXpress FcεRI as a Complex Composed of FcεRIα- and FcεRIγ-Chains and Can Use This Receptor for IgE-Mediated Allergen Presentation" J. Immunol. 157:607-616.

Pickl et al. (1996) "Molecular and Functional Characteristics of Dendritic Cells Generated from Highly Purified CD14$^+$Peripheral Blood Monocytes" J. Immunol. 157:3850-3859.

Fanger et al. (1997) "Characterization of Expression, Cytokine Regulation, and Effector Function of the High Affinity IgG Receptor FcγRI (CD64) Expressed on Human Blood Dendritic Cells" J. Immunol. 158:3090-3098.

De Palma et al. (1999) "Use of Antagonist Peptides to Inhibit In Vitro T Cell Responses to Par j1, the Major Allergen of Parietaria judaica Pollen" J. Immunol. 162:1982-1987.

Shalaby et al. (1992) "Development of Humanized Bispecific Antibodies Reactive with Cytotoxic Lymphocytes and Tumor Cells Overexpressing the HER2 Protooncogene" J. Exp. Med. 175:217-225.

Oyama et al. (1998) "Vascular Endothelial Growth Factor Affects Dendritic Cell Maturation Through the Inhibition of Nuclear Factor-κb Activation in Hemopoietic Progenitor Cells" J. Immunol. 160:1224-1232.

Strobl et al. (1998) "Identification of CD68$^+$1in Peripheral Blood Cells with Dendritic Precursor Characteristics" J. Immunol. 161:740-748.

Ridderstaad et al. (1998) "Kinetics of Establishing the Memory B Cell Population as Revealed by CD38 Expression" J. Immunol. 160:4688-4695.

Ishida, et al. (1998) "Defective function of Langerhans cells in tumor-bearing animals is the result of defective maturation from hemopoietic progenitors" J. Immunol. 161:4842-4851.

Ito et al. (1999) "A CD1a⁺/CD11c⁺ Subset of Human Blood Dendritic Cells is a Direct Precursor of Langerhans Cells" J. Immunol. 163:1409-1419.

Bates et al. (1999) "APCs express DCIR, a novel C-type lectin surface receptor containing an immunoreceptor tyrosine-based inhibitory motif" J. Immunol. 163:1973-1983.

Kohrgruber et al. (1999) "Survival, maturation, and function of CD11c⁻ and CD11c⁺ peripheral blood dendritic cells are differentially regulated by cytokines" J. Immunol. 163:3250-3259.

Ohm et al. (1999) "Effect of Vascular Endothelial Growth Factor and FLT3 Ligand on Dendritic Cell Generation in Vivo" J. Immunol. 163:3260-3268.

Crawford et al. (1999) "Circulating CD2⁺ Monocytes Are Dendritic Cells" J. Immunol. 163:5920-5928.

Bave et al. (1999) "The Combination of Apoptotic U937 and Lupus IgG is a Potent IFN-α Inducer" J. Immunol. 163:6306-6313.

Vallin et al. (2000) "Anti-Double-Stranded DNA Antibodies and Immunostiumlatory Plasmid DNA in Combination Mimic the Endogenous IFN-α Inducer in Systemic Lupus Erythematosus" J. Immunol. 165:3519-3526.

Yamaguchi et al. (1995) "Difficulties obtaining monoclonal antibodies to subsets of human leukocytes using neonatal tolerance induction in mice" J. Immunol. Met. 181:115-124.

Bender et al. (1996) "Improved methods for the generation of dendritic cells from nonproliferating progenitors in human blood" J. Immunol. Met. 196:121-135.

Romani et al. (1996) "Generation of mature dendritic cells from human blood An improved method with special regard to clinical applicability" J. Immunol. Met. 196:137-151.

Pizza et al. (1984) "Tumor Regression After Intralesional Injection of Interleukin 2 (IL-2) In Bladder Cancer Preliminary Report" J. Int. Cancer 34:359-367.

Levitt et al. (1983) "Molecular Dynamics of Native Protein" J. Mol. Biol. 168:595.

Marks et al. (1991) "By-passing Immunization Human Antibodies from V-gene Libraries Displayed on Phage" J. Mol. Biol. 222:581-597.

Conforti et al. (1997) "Update on Active Specific Immunotherapy With Melanoma Vaccines" J. Surg. Oncol. 66:55-64.

Lennert et al. (1975) "T-Associated Plasma Cells" Lancet 1:1031-1032.

Tarte et al. (1999) "Dendritic cell-based vaccine: a promising approach for cancer immunotherapy" Leukemia 113:653-663.

Fletcher et al. (1987) "Recent Advances in the Understanding of the Biochemistry and Clinical Pharmacology of Interleukin-2" Lymphokine Res. 6:45.

Tam (1989) "High-Density Multiple Antigen-Peptide System for Preparation of Antipeptide Antibodies" Met. Enz. 168:7-15.

Miller et al. (1985) "Generation of helper-free amphotropic retroviruses transduce dominant-acting, methotrexate-resistant dihydrofolate reductase gene" Mol. Cell. Biol. 5:431-437.

Miller et al. (1986) "Redesign of retrovirus Packaging Cell Lines to Avoid Recombination Leading to Helper Virus Production" Mol. Cell. Biol. 6:2895-2902.

Colaco (1999) "Why are dendritic cells central to cancer immunotherapy?" Molec. Med. Today 5:14-17.

Kohler and Milstein (1975) "Continuous cultures of fused cells secreting antibody of predefined specificity" Nature 256:495-497.

Winter and Milstein (1991) "Man-made antibodies" Nature 349:293-299.

Caux et al. (1992) "GM-CSF and TNF-α cooperate in the generation of dendritic Langerhans cells" Nature 360:258-261.

Vaughan et al. (1996) "Human Antibodies with Sub-nanomolar Affinities Isolated from a Large Non-immunized Phage Display Library" Nature Biotechnol. 14:309-314.

Zhao et at (1998) "Molecular evolution by staggered extension process (Step) in vitro recombination" Nature Biotechnol. 15:258.

Singh et al. (1999) "Advances in vaccine adjuvants" Nature Biotechnol. 17:1075-1081.

Gabrilovich et al. (1996) "Production of vasular endothelial growth factor by human tumors inhibits the functional maturation of dendritic cells" Nature Med. 2:1267.

Cella et al. (1999) "Plasmacytoid monocytes migrate to inflamed lymph nodes and produce large amounts of type I interferon" Nature Med. 5:919-923.

Baldessarini et al. (1973) "Serotonin Metabolism in Rat Brain after Surgical Diversion of the Portal Venous Circulation" Nature New Biol. 245:25-27.

Hermans et al. (1998) "The emerging role of the dendritic cell in novel cancer therapies" N.Z. Med. J. 111:111-113.

Fitzgerald-Bocarsly (1993) "Human Natural Interferon-α Producing Cells" Pharmacol. Ther. 60:39-62.

Danos et al. (1988) "Safe and efficient generation of recombinant retroviruses with amphotropic and ecotropic host ranges" Proc. Natl. Acad. Sci. USA 85:6460-6464.

Miyamura et al. (1994) "Parvovirus particles as platforms for protein presentation" Proc. Natl. Acad. Sci. USA 91:8507-8511.

Zhou et al. (1996) "CD14⁺ blood monocytes can differentiate into functionally mature CD83⁺ dendritic cells" Proc. Natl. Acad. Sci. USA 93:2588-2592.

Olweus et al. (1997) "Dendritic cell ontogeny: A human dendritic cell lineage of myeloid origin" Proc. Natl. Acad. Sci. USA 94:12551-12556.

Sheets et al. (1998) "Efficient construction of a large nonimmune phage antibody library: The production of high-affinity human single-chain antibodies to protein antigens" Proc. Natl. Acad. Sci. USA 95:6175-6162.

Rader et al. (1998) "A phage display approach for rapid antibody humanization: designed combinatorial V gene libraries" Proc. Natl. Acad. Sci. USA 95:8910-8915.

Diener et al. (1986) "Specific Immunosuppression by Immunotoxins Containing Daunomycin" Science 231:148.

Vitatta (1987) "Redesigning Nature's Poisons to Create Anti-Tumor Reagents" Science. 238:1098-1104.

Bird et al. (1988) "Single-chain Antigen-Binding Proteins" Science 242:423-426.

McCune et al. (1988) "The SCID-hu Mouse: Murine Model for the Analysis of Human Hematolymphoid Differentiation and Function" Science 241:1632-1639.

Rosenberg et al. (1989) "A New Approach to the Adoptive Immunotherapy of Cancer with Tumor-Infiltrating Lymphocytes" Science 233:1318.

Butcher et al. (1996) "Lymphocyte Homing and Homeostasis" Science 272:60-66.

Rissoan et al. (1999) "Reciprocal Control of T Helper Cell and Dendritic Cell Differentiation" Science 283:1183-1186.

Siegal et al. 1999 "The Nature of the Principal Type 1 Interferon-Producing Cells in Human Blood" Science 284:1835-1837.

Hart et al. (1999) "Presentation of Tumor Antigens" Semin. Hematol. 36:21-25.

Thomas et al. (1996) "Dendritic cells: Origin and differentiation" Stem Cells 14:196-206.

De Wynter et al. (1998) "CD34⁺AC133⁺ Cells Isolated from Cord Blood are Highly Enriched in Long-Term Culture-Initiating Cells, NOD/SCID-Repopulating Cells and Dendritic Cell Progenitors" Stem Cells 16:387-396.

Peiper et al. (1997) "Generation of peptide-specific cytotoxic T lymphocytes using allogeneic dendritic cells capable of lysing human pancreatic cancer cells" Surgery 122:235-41.

Hock et al. (1999) "Human dendritic cells express a 95 kDa activation/differentiation antigen defined by CMRF-56" Tiss. Antigens 53:320-334.

Thurnher et al. (1998) "Dendritic Cell-Based Immunotherapy of Renal Cell Carcinoma" Urol. Int. 61:67-71.

Brown et al. (1994) "Chimeric Parvovirus B19 Capsids for the Presentation of Foreign Epitopes" Virol. 198:477-488.

Olsnes et al. (1981) "Chimeric Toxins" Pharmac. Ther. 15:355-381.

"Monoclonal Antibodies for Cancer Detection and Therapy," eds. Baldwin and Byers, pp. 159-179, 224-266, Academic Press (1985).

Kantor et al. (1997) Magnetic cell sorting with colloidal superparamagnetic particles. In, Cell Separation Methods and Applications, Recktenwald et al. Eds. Marcel Dekker Inc. New York, pp. 153-173.

Miltenyi et al. (1999) High gradient magnetic cell sorting In, Flow cytometry and cell sorting, Ed., Radbruch Springer-Verlag, Berlin pp. 218-247.

Bagot, M. et al. (1997). "CD101 is Expressed by Skin Dendritic Cells: Role in T-Lymphocyte Activation," *Tissue Antigens* 50(5): 439-448.

Brossart, P. et al. (1997). "Virus-Mediated Delivery of Antigenic Epitopes into Dendritic Cells as a Means to Induce CTL," *J. Immunol.* 155(158):3270-3276.

de Saint-Vis, B. et al. (1998). "The Cytokine Profile Expressed by Human Dendritic Cells is Dependent on Cell Subtype and Mode of Activation," *J. Immunol.* 160(4):1666-1676.

Dzionek, A. et al. (2000). "BDCA-2, BDCA-3 and BCDA-4: Three Markers for Distinct Subsets of Dendritic Cells in Human Peripheral Blood;" *J. Immunol.*. 165:6037-6046.

Dzionek, A. et al. (2000). "BDCA-2, BDCA-3 and BCDA-4: Three Novel Markers for Distinct Subsets of Dendritic Cells in Human Peripheral Blood," *Tissue Antigens* 55(Supp. 1):55-56.

Engels, F.H. et al. (1999). "Calcium Signaling Induces Acquisition of Dendritic Cell Characteristics in Chronic Myelogenous Leukemia Myeloid Progenitor Cells," *PNAS* 96(18):10332-10337.

Everson, M.P. et al. (1993). "Dendritic Cells Regulate Th1 Versus Th3 Responses," *J. Leukocyte Biology* (*International Congress on the Regulation of Leukocyte Production and Immune Funtion held at the Joint Meeting of the Australiasian Society for Immunology and Society for Leukocyte Biology*). p. 72 (AbStract No. 237).

U.S. Appl. No. 60/192,934, filed Mar. 29, 2000, Werner et al.

U.S. Appl. No. 60/205,020, filed May 18, 2000, Werner et al.

U.S. Appl. No. 60/205,026, filed May 18, 2000, Mourier.

U.S. Appl. No. 60/205,767, filed May 19, 2000, Werner et al.

U.S. Appl. No. 60/205,769, filed May 19, 2000, Jaritz et al.

Fitzgerald-Bocarsly, P. et al. (1999). "Virally-Responsive IFN-alpha Producing Cells in Human Blood and Tonsil are CD11C/CD123+ Cells Identical to Precursors of Type Two Dendritic Cells (pDC2)," *J. Interferon and Cytokine Research* 19(Supp. 1):S117. (Abstract No. P81).

Kahan, M. (1997). "Detecting Intracellular Cytokines in Activated Monocytes," Becton Dickinson and Co. Application Note 2. pp. 1-11.

Larregina, A. et al. (1997). "Pattern of Cytokine Receptors Expressed by Human Dendritic Cells Migrated from Dermal Explants," *Immunology* 91(2):303-313.

Liu et al. (1991). "The Enhancing Effect of Calcium Ionophore A23187 on the Accessory Function of Mouse Dendritic Cells," *Zhongguo Yi Xue Ke Xue Yuan Xue Bao.* 13(3):176-80. (Abstract attached).

Luft, T. et al. (1998). "Type I IFNs Enhance the Terminal Differntiation of Dendritic Cells," *J. Immunol.* 161:1947-1953.

Munzny D.M. et al. (Feb. 5, 1999). Database EMBL Online ID: AC006517, p. 1-3.

Rovere, P. et al. (1998). "Dendritic Cells Preferentially Internalized Apoptotic Cells Opsonized by Anti-beta2-Glycoprotein I Antibodies," *J. Autoimmunity* 11(5):403-411.

Rubartelli, A. et al. (1997). "The Selevtive Engulfment of Apoptotic Bodies by Dendritic Cells is Mediated by the alph(v)beta3 Intergrin and Requires Intracellular and Extracellular Calcium," *Euro. J. Immunol.* 27(8):1893-1900.

Schmitt, D. et al. (1987). "Antigenic Thymus-Epidermis Relationships Reactivity of a Panel of Anti-Thymic Cell Monoclonal Antibodies on Human Keratinocytes and Langerhans Cells," *Dermatologica* 175(3):109-120.

Soler, P. et al. (1989). "Cigarette Smoking-Induced Changes in the Number and Differentiated State of Pulmonay Dendritic Cells-Langerhans Cells," *American Review of Respiratory Disease* 139(5):1112-1117.

Suni, M.A. et al. (1998). "Detection of Antigen-Specific T-Cell Cytokine Expression in Whole Blood by Flow Cytometry," *Journal of Immunological Methods* 212:89-98.

Theodora, I. et al. (1990). "CD1 Stimulation of Human T Cell Lines Induces a Rapid Increase in the Intracellular Free Calcium Ion Concentration and the Production of IL-2," *J. Immunol.* 144(7):2518-2523.

Tuting, T. et al. (1998). "Autologous Human Monocyte-Derived Dendritic Cells Genetically Modified to Express Melanoma Antigens Elicit Primary Cytotoxic T Cell Responses in vitro: Enhancement by Contrasfection of Genes Encoding the Th1-Biasing Cytokines IL-12 and IFN-alpha," *J. Immunol.* 160(3):1139-1147.

Valladeau, J. et al. (1998). "A Monoclonal Antibody Against Langerin, a Protein Specific of Langerhans Cells, is Internalized in Coated Pits and Birbeck Granule," *J of Leukocyte Biology* Suppl. 2 (Abstract No. A35).

Willmann, K. and Dunne, J.F. (2000). "A Flow Cytometric Immune Function Assay for Human Peripheral Blood Dendritic Cells," *Journal of Leukocyte Biology* 67:536-544.

Willmann, K. et al. (1998). "Peripheral Blood Dendritic Cells Revealed by Flow Cytometry" Becton Dickinson and Co. Application Note 3. pp. 1-12.

Borrebaeck el al., "Human monoclonal antibodies produced by primary in vitro immunization of peripheral blood lymphocytes," *PNAS*, 85:3995-3999 (1988).

Duenas at al., "In Vitro Immunization of naive human B cells yields high affinity immunoglobulin G antibodies as illustrated by phage display," *Immunology*, 89:1-7 (1996).

Kellermann et al., "Antibody discovery: the use of transgenic mice to generate human monoclonal antibodies for therapeutics," *Current Opinion in Biotechnology*, 13:593-597 (2002).

Koda et al., "Immunotherapy for Recurrent Colorectal Cancers with Human Monoclonal Antibody SK-1," *Anticancer Research*, 21:621-628 (2001).

Mendez et al., "Functional transplant of megabase human immunoglobulin loci recapitulates human antibody response in mice," *Nature Genetics*, 15:146-156 (1997).

Muzny et al., accession No. AC006517, from EMBL/Genbank/DDBJ database, submitted Feb. 5, 1999, Homo sapiens chromosome 12p13.1-17.1-21.3 clone RPCIII-277J24, working draft sequence, 63 unordered pieces.

FIGURE 1
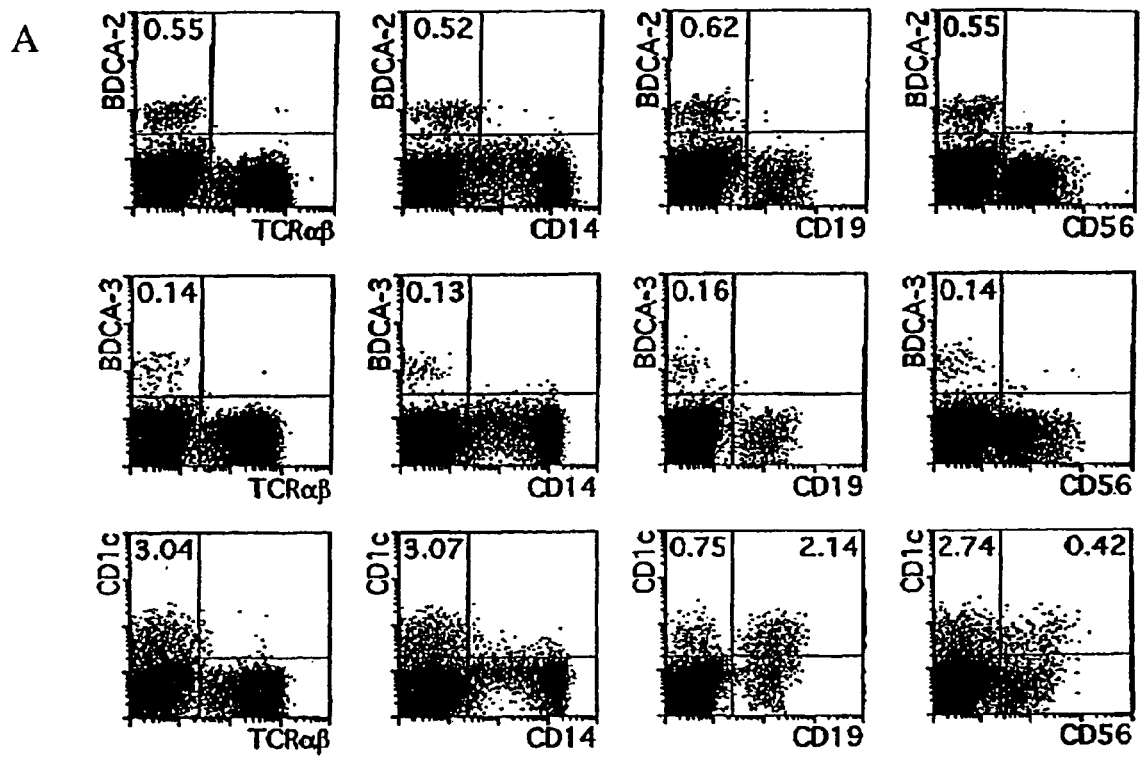
B
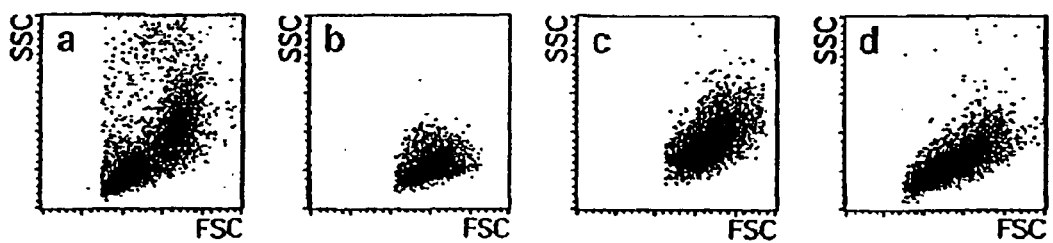

MVPEEEPQDREKGLWWFQLKVWSMAVVSILLLSVCFTVSSVVPHNFMYS
KTVKRLSKLREYQQYHPSLTCVMEGKDIEDWSCCPTPWTSFQSSCYFISTG
MQSWTKSQKNCSVMGADLVVINTREEQDFIIQNLKRNSSYFLGLSDPGGR
RHWQWVDQTPYNENVTFWHSGEPNNLDERCAIINFRSSEEWGWNDIHCH
VPQKSICKMKKIYI (SEQ ID NO: )

FIGURE 12

CAGTGATTCTCGTGCCTCAGCCTCCTGAGTAGCCGAAATTACAGACGTG
TGCCACCATGCTTGGCTAATTTTTTGGATTTTTAGTAGAGATGGGGTTTC
ACTATGTTGGCCAGGCTAGTCTTGAACTCCTGGCCTGAAGCAATCCGCC
CACCTCAGCCTCCCAAAGTGCTGAGATTATAGGCACGAGCCACTACAC
CTGGCCACAAAATTCTTTAAAGAAGCCAATCCCATCCTCCCTCAAGAGC
CAAGGGGCCACCTCACCCTCTTGTTACAGCAGATCCTGCCTCCACAGTC
ACCCTGCTCCCAAGTGCAACCTCTGTCTGACCCTGCATGGTGTGCGGTG
CCCTCCTGCCTCAGGCCGCGAAGAAGGATCTAAGGGCTTGGCTTGTTTG
AAAGAACCACACCCCGAAAGTAACATCTTTGGAGAAAGTGATACAAGA
GCTTCTGCACCGACCTGATAGAGGAAGTCCAAAGGGTGTGCGCACACA
CAATGGTGCCTGAAGAAGAGCCTCAAGACCGAGAGAAAGGACTCTGGT
GGTTCCAGTTGAAGGTCTGGTCCATGGCAGTCGTATCCATCTTGCTCCT
CAGTGTCTGTTTCACTGTGAGTTCTGTGGTGCCTCACAATTTTATGTATA
GCAAACTGTCAAGAGGCTGTCCAAGTTACGAGAGTATCAACAGTATC
ATCCAAGCCTGACCTGCGTCATGGAAGGAAAGGACATAGAAGATTGGA
GCTGCTGCCCAACCCCTTGGACTTCATTTCAGTCTAGTTGCTACTTTATT
TCTACTGGGATGCAATCTTGGACTAAGAGTCAAAAGAACTGTTCTGTGA
TGGGGGCTGATCTGGTGGTGATCAACACCAGGGAAGAACAGGATTTCA
TCATTCAGAATCTGAAAAGAAATTCTTCTTATTTCTGGGGCTGTCAGA
TCCAGGGGGTCGGCGACATTGGCAATGGGTTGACCAGACACCATACAA
TGAAAATGTCACATTCTGGCACTCAGGTGAACCCAATAACCTTGATGA
GCGTTGTGCGATAATAAATTTCCGTTCTTCAGAAGAATGGGGCTGGAAT
GACATTCACTGTCATGTACCTCAGAAGTCAATTTGCAAGATGAAGAAG
ATCTACATATAAATGAAATATTCTCCCTGGAAATGTGTTTGGGTTGGCA
TCCACCGTTGTAGAAAGCTAAATTGATTTTTTAATTTATGTGTAAGTTTT
GTACAAGGAATGCCCCTAAAATGTTTCAGCAGGCTGTCACCTATTACAC
TTATGATATAATCCAAAAAAAAAAAAAAAAAAAAAAAAAAAAAA
(SEQ ID NO: )

FIGURE 13
A 
B 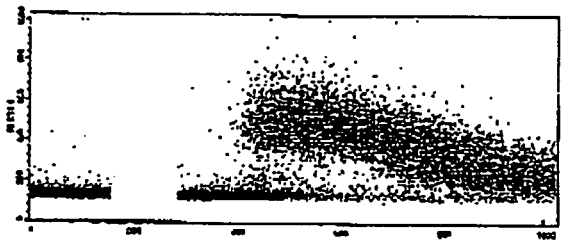
C 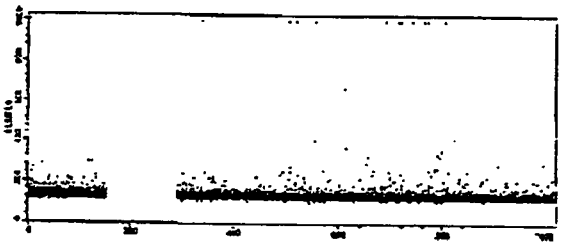
D 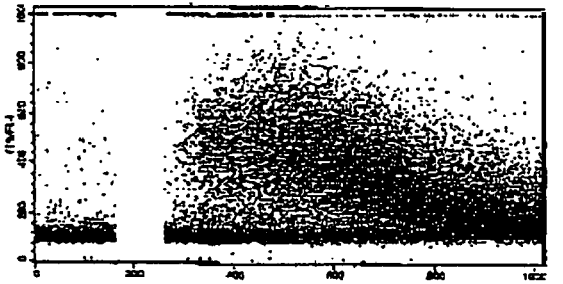
E 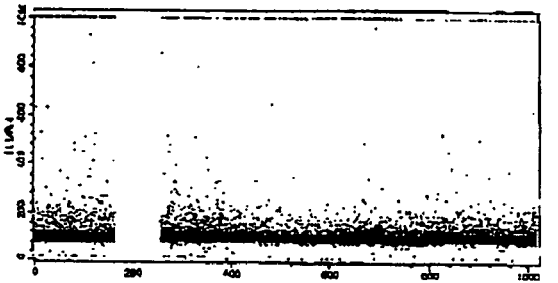

FIGURE 14
A
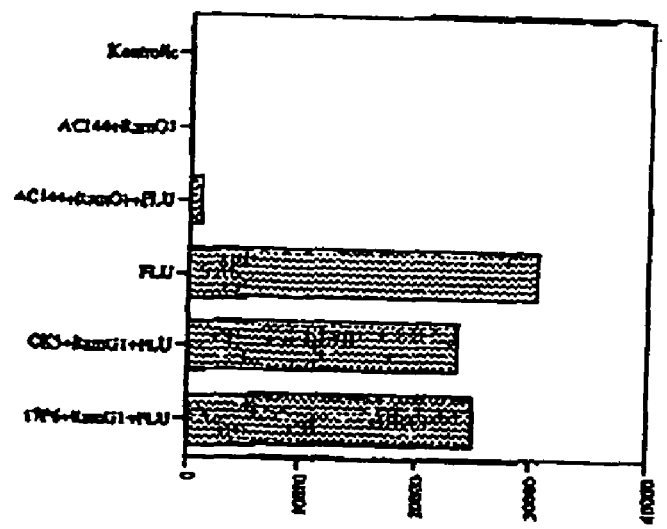
Type I interferon
B
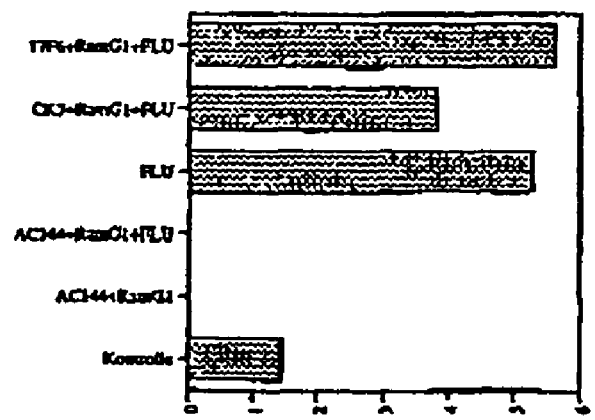
Type I interferon

FIGURE 22

```
1 mDectin2alph
                    360  intron  370        380        390        400        410
BDCA2cDNA.tx    CCTCAGGCCGCGAAGAAGGATCTAAGGGCTTGGCTTGTTTGAAAGAACCACACCCCGAA-
                :  :  ::::   :   :  ::  :::    :      :::  ::   :::    :  :::
mDectin2alph    CATTGGCCCGCTCTGTGGCATTTAA----CTCAAGTGTGTG-TGGAAGTTGATTCTGAAC
                    10         20         30         40         50
                    420        430        440        450        460
BDCA2cDNA.tx    AGTAACATCTTTG-GAGAA-AGTGATACAAGAG----CTTCTGCACCCACCTGATAGAGG
                :  :  ::::::   ::::      :  :  :      ::  ::  :  ::  :   :::
mDectin2alph    TCTGGCCTCTTTGACAGAAGCCAGGTCCCTGAGTCGTATTTTGGAGACAGATGCAAGA--
                    60         70         80   Met  90         100        110
                    470        480        490   Met  500        510        520 intron
BDCA2cDNA.tx    AAGTCCAAAGGGTGTGGGCACACACAATGGTGCCTGAAGAAGAGCCCTCAAGACCGACGA
                :: ::   :: ::    ::  ::::    :            :  :::     :: :: ::
mDectin2alph    AACCCCTGACCTTCTGAACATACACCTCAACAATGGTGCAGGAAAGACAATCCCAAGGGA
                    120        130        140 Met 150        160        170
                    530        540        550        560        570        580  intron
BDCA2cDNA.tx    AAGGACTCTGGTGGTTCCAGTTGAAGGTCTGGTCCATGGCAGTCGTATCCATCTTGCTCC
                :  :::  ::::  :::  ::  :    :  ::::::::  :::::::::  :::  :::
mDectin2alph    AGGGAGTCTGCTGGACCCTG---AGACTCTGGTCAGCTGCTGTGATTTCCATGTTACTCT
                    180        190        200        210        220        230
                    590        600        610 intron 620        630        640
BDCA2cDNA.tx    TCAGTGTCTGTTTCACTGTGAGTTCTGTGGTGCCTCACAATTTTATGTATAGCAAAACTG
                :  :::  :::::::  ::  :::   :  :::::::   ::  ::  ::  :::    :  :
mDectin2alph    TGAGTACCTGTTTCATTGCGAGCTGTGTGGTGACTTACCAATTTAT-TAT---GGACCAG
                    240        250        260 intron 270        280
                    650        660        670        680        690        700
BDCA2cDNA.tx    TCAAGAGGCTGTCCAAGTTACGAGAGTATCAACAGTATCATCCAAGCCTGACCTGCGTCA
                :  ::   :   :  :.       ::  ::   :  :   :  :::::   :  ::::::  :::
mDectin2alph    CCCAGTAGAAG---ACTATATGA-ACT-TCACACATACCATTCCAGTCTCACCTGCTTCA
                    290        300        310 intron 320        330        340
                    710        720        730        740        750
BDCA2cDNA.tx    -TGGAAGGA--AAGG--ACATAGAAGAT-TGGAGCTGCTGCCCAACCCCTTGGACTTCAT
                ::  :  :::   :  :::   ::  ::  ::  ::  :::  :  X::::::::::  :  ::::   ::::
mDectin2alph    GTGAAGGGACTATGGTGTCAGAAAAAATGTGGGGATGCTGCCCAAATCACTGGAAGTCAT
                    350        360        370        380        390        400
                    760        770        780 intron 790        800        810
BDCA2cDNA.tx    TTCAGTCTAGTTGCTACTTTATTTCTACTGGGATGCAATCTTGGACTAAGAGTCAAAAGA
                ::     ::  ::  ::::::    ::::::::::      :   :   :  :  :::    ::::        :::
mDectin2alph    TTGGCTCCAGCTGCTACCTCATTTCTACCAAGGAGAACTTCTGGAGCACCAGTGAGCAGA
                    410        420        430        440        450        460 intron
                    820        830        840        850        860        870
BDCA2cDNA.tx    ACTGTTCTGTGATGGGGGCTGATCTGGTGGTGATCAACACCAGGGAAGAACAGGATTTCA
                :::::     :    ::::::::::::   :::::::::::::   ::       ::   ::   :::::::
mDectin2alph    ACTGTGTTCAGATGGGGGCTCATCTGGTGGTGATCAATACTGAAGCGGAGCGAAATTTCA
                    470        480        490        500        510        520 intron
                    880        890        900        910        920        930
BDCA2cDNA.tx    TCATTCAGAATCTGAA-AAGAAATTCTTCTTATTTTCTGGGGCTGTCAGATCCAGGGGGT
                :::     :::  :  :::::    :::::    :: :::::     :  :::::     :::
mDectin2alph    TCACCCAGCAGCTGAATGAGTCACT-TTCTTACTTCCTGGGTCTTTCGGATCCACAAGGT
                    530        540        550        560        570        580
                    940        950        960        970        980
BDCA2cDNA.tx    CGGCGACATTGGCAATGGGTTGACCAGACACCATACAATGAAAATGTCACATTCTGGCAC
                :       :  ::::::::::  ::   ::   :  ::   :  ::::::::::::  :::::::::::::
mDectin2alph    AATGGCAAATGGCAATGGATCGATGATACTCCTTTCAGTCAAAATGTCAGGTCTGGCAC
                    590        600        610        620        630        640 intron
                    1000       1010       1020       1030       1040       1050
BDCA2cDNA.tx    TCAGGTGAACCCAATAACCTTGATGAGCGTTGTGCGATAATAAATTTCCGTTCTTCAGAA
                :      ::::::::::::  ::  ::::::  ::  :::::    :::       ::   ::::::::
mDectin2alph    CCCCATGAACCCAATCTTCCAGAAGAGCGGTGTGTTTCAATAGTTTACTGGAATCCTTCG
                    650        660        670        680        690        700
                    1060       1070       1080       1090       1100       1110
BDCA2cDNA.tx    GAATGGGGCTGGAATGACATTCACTGTCATGTACCTCAGAAGTCAATTTGCAAGATGAAG
                :::::::::::::::::::   ::   ::::   ::        ::  :::  ::::: ::        ::::::
mDectin2alph    AAATGGGGCTGGAATGATGTTTTCTGTGATAGTAAACACAATTCAATATGTGAAATGAAG
                    710        720        730        740        750        760
                    1120       1130 stop  1140       1150       1160       1170
BDCA2cDNA.tx    AAGATCTACATATAAATGAAATATTCTCCCTGGAAATGTGTTTGGGTTGGCATCCACCGT
                ::::X       ::   ::  : :          :::  ::::::::  ::      :::
mDectin2alph    AAGATTTACCTATGATG-CCTGTTATTCATTAATATCT-TTAAAGTTCAGACCTACC--
                    770        780        790        800        810
                    1180       1190 stop  1200       1210       1220       1230
BDCA2cDNA.tx    TGTAGAAAGCTAAATTGATTTTTTAATTTATGTGTAAG-TTTTGTACAAGGAAT-GCCCC
                    ::::   :   ::    ::          :: ::    ::   ::::::::    :      :::  :
mDectin2alph    --AAGAAGCCATAACTTCTTGGCCTGTACATCTGACAGAGGCCGTTCTTTTCCTAGCCAC
                    820        830        840        850        860        870
                    1240       1250       1260       1270       1280       1290
BDCA2cDNA.tx    TAAAATGT---TTCAGCAGGCTGTCACCTATTACACTTATGATATAATCCAAAAAAAAAA
                ::  :          ::  :::  :::  :::::
mDectin2alph    TATTCTTTACTCAAACAGAATGAGCCCT-TTCTCCTTCTGATGGTTAGAGTTTTGTCAAC
                    880        890        900        910        920        930
                    1300       1310
BDCA2cDNA.tx    AAAAAAAAAAAAAAAAAAAA mDectin2alph    TTGACACAAACTAGAGTCA
                    940        950
```

FIGURE 23

```
BDCA-2    MVPEEEPQDR--EKGLWWFQLKVWSMAV------------------VSILLLSVCFTVS  39
DECTIN-2  MVQERQSQG----KGVCWT-LRLWSAAV--------------------ISMLLLSTCFIAS 36
DCIR      MTSEITYAEVRFKNEFKSSGINTASSAASKERTAPHKSNTGFPKLLCASLLIFFLLLATS  60
          *. *         :.     :.  * *.                      *:*::   : *

C   W        C H
BDCA-2    SVVPHNFMYSKTVKRLSKLREYQQYHPSLTCVMEGKDIED--WSC              97
DECTIN-2  CVVTYQFIMDQPSRRLYEL---HTYHSSLTCFSEGTMVSEKMWGC              93
DCIR      FFIAFVIFFQKYSQLLEKKTTKELVHTTLECVKKNMPVEETAWSC             120
          .:.. ::  .: :* :    . *.:* *. :.   :.: *.*** . *.** *.**.*

A    A  C     A A    E  HA          AAGA +       A H
BDCA-2                                                            157
DECTIN-2                                                          153
DCIR                                                              180
          **     *   *.::*    * *.*:****.  **.**  *:*:... :**.:***** *..:****.*

H     W    +P++   ++CA         W++   C         C
BDCA-2                                                            KMKKIYI---- 213
DECTIN-2                                                          MKKIYL---  209
DCIR                                                              MMKIHL---  237
          :**:.:.  ***. **.   :***. : :    ...****:  *    :..*:*:* **::
```

METHOD FOR ISOLATING BDCA-4+ DENDRITIC CELLS

CROSS-REFERENCE TO RELATED APPLICATIONS

This application is a continuation of U.S. application Ser. No. 09/714,712, filed Nov. 15, 2000, the entire contents of which are incorporated by reference herein for all purposes; which claims the benefit of United States patent applications Application No. 60/197,205 filed Apr. 13, 2000; Application No. 60/196,824 filed Apr. 11, 2000; Application No. 60/180,775 filed Feb. 7, 2000; Application No. 60/179,003 filed Jan. 28, 2000; Application No. 60/167,076 filed Nov. 23, 1999; and Application No. 60/165,555 filed Nov. 15, 1999.

STATEMENT OF RIGHTS TO INVENTIONS MADE UNDER FEDERALLY SPONSORED RESEARCH

Not applicable.

TECHNICAL FIELD

The present invention relates to antibodies and derivatives thereof specific for subpopulations of dendritic cells (DCs). Compositions and methods of use thereof are also provided including isolation and purification of DCs and subpopulations thereof and antibody- or ligand-mediated immunotherapy. The invention also provides substantially isolated DC subpopulations. Methods of use thereof are also provided including DC-based immuunotherapy, characterization of various diseases and in vivo numeric DC expansion for instance with flt3-Ligand.

BACKGROUND OF THE INVENTION

The hematopoietic development of dendritic cells (DCs), potent antigen presenting cells (APCs) is distinct and may follow several precursor pathways some closely linked to monocytes. DCs may be derived from a lymphoid precursor. Thomas et al. (1993) J. Immunol. 150:821-834. Like in blood, there may be three distinct subsets of DCs present in the thymus: 1) plasmacytoid CD4+CD11c– DCs; 2) CD4+ CD11c+ DCs and 3) interdigitating DCs. It has been proposed that thymic DCs and T cells arise from a common stem cell. Thomas et al. (1996) Stem Cells 14:196-206.

Generation of large numbers of DCs for potential clinical use has recently been accomplished through the in vitro culturing of progenitors with cytokines. Various strategies have been adopted to introduce antigens into dendritic cells so that they may be more effectively presented to T cells in the context of costimulation. It has also been shown that dendritic cells can influence the T cell response to antigen to follow either a humoral or systemic pathway.

T cells are unable to respond to unprocessed proteins, rather, they require accessory cells to present antigen as peptide epitopes displayed on the cell surface in conjunction with MHC molecules. Antigens generated endogenously in the cell cytoplasm are typically presented in the Class I pathway and stimulate cytotoxic T lymphocyte (CTL) reactions while exogenous protein is process in MHC Class II compartments and induce helper (CD4) T cell responses. The stimulation of naive T cells requires the presence of costimulatory molecules that act as secondary signals in the activation of primary immunity. APCs such as B cells and macrophages are typically incapable of inducing primary responses. In contrast, dendritic cells drive their potency from the constitutive unregulated expression of costimulatory, adhesion and MHC Class I and II molecules essential for the initiation of effective cellular immunity. For review see, Avigan (1999) Blood Rev. 13:51-64.

DCs are APC that are essential for initiation of primary immune responses and the development of tolerance. DCs express MHC, necessary for stimulation of naive T cell populations. The hematopoietic development of DCs is distinct and may follow several precursor pathways, some of which are closely linked to monocytes. See, for review, Avigan (1999) Blood Rev. 13:51-64. Different DC subsets have distinct developmental pathways. The emerging concept is that one DC subset has regulatory functions that may contribute to the induction of tolerance to self-antigens. Austyn (1998) Curr. Opin. Hematol. 5:3-15. Conversely, DCs, or a subset thereof, may also be involved in the induction of immune responses to self-proteins. It is thought that certain autoimmune responses may be due to microenvironmental tissue injury followed by local DC activation and subsequent interaction with T cells to initiate an immune response. Ibrahim et al. (1995) Immunol. Today 16:181-186.

The ability of DCs to initiate T cell responses is being used in DC cancer vaccines. Hart et al. (1999) Sem. Hematol. 36::21-25. For instance, DCs are generated in vitro from $CD34^+$ cells or monocytes, pulsed with tumor-derived peptides or proteins and returned to the patient to act as APCs in cancer-specific T cell induction. Brugger et al. (1999) Ann. N.Y. Acad. Sci. 872:363-371. Animal models have demonstrated that DC tumor vaccines reverse T cell anergy and result in subsequent tumor rejection. Avigan (1999); see also, Tarte et al. (1999) Leukemia 13:653-663; Colaco (1999) Molec. Med. Today 5:14-17; Timmerman et al. (1999) Ann. Rev. Med. 50:507-529; Hart et al. (1999) Semin. Hematol. 36:21-25; Thurnher et.al. (1998) Urol. Int. 61:67-71; and Hermans et al. (1998) N.Z. Med. J. 111:111-113. One approach has been to increase DCs in vivo by administration of flt-Ligand. This has the effect of compensating for VEGF-induced DC suppression. Ohm et al. (1999) J. Immunol. 163:3260-3268. DCs have been proposed for use as adjuvants in vaccination and in recombinant vaccines. Fernandez et al. (1998) Cyto. Cell. Mol. Ther. 4:53-65; and Gilboa et al. (1998) Cancer Immunol. Immunother. 46:82-87. DC have also been proposed for use in enhancing immunity after stem cell transplantation. Brugger et al. (1999) Ann. NY Acad. Sci. 363-371. DCs play a number of potential roles in immunology. For instance, DCs are involved in human immunodeficiency virus (HIV) infection. Zoeteweij et al. (1998) J. Biomed. Sci. 5:253-259. DCs have also been proposed as suitable for use in HIV therapy. Weissman et al. (1997) Clin. Microbiol. Rev. 10:358-367.

Additional immunologic functions are related to DCs such as differential induction of Th1 or Th2 responses, autoimmune reactions and allergies. Rissoan et al. (1999) Science 283:1183-1186; Hermans et al. (1998) NZ Med. J. 111:111-113; and De Palma et al. (1999) J. Immunol. 162:1982-1987.

Increased levels of circulating IFN-α and of IFN-α inducing factor (something like a complex of anti-DNA antibody and DNA) are found in SLE patients and correlate to disease activity. Furthermore, patients-with non-autoimmune disorders treated with IFN-α frequently develop autoantibodies and occasionally SLE. Several papers from Ronnblom et al. (1999) Clin. Exp. Immunol. 115: 196-202; (1999) J. Immunol. 163: 6306-6313; and (2000) J. Immunol. 165: 3519-3526) show that IFN-α inducing factors derived from patients induce secretion of IFN-α in PBMC from healthy donors and they selectively activate natural IFN-α producing cells (NIPC=plasmacytoid DC).

Studies on DC's in blood have been hampered by scarcity of the cells and the relative lack of DC-specific cell surface markers. Methods for DC isolation are based on either maturational change after a short culture period, like the acquisition of low buoyant density or the expression of DC activation/maturation antigens (CD83, CMRF-44 and CMRF-56). Young et al. (1988) Cell Immunol. 111:167; Van Voorhis et al. (1982) J. Exp. Med. 155:1172; Zhou et al. (1995) J. Immunol. 154:3821-3835; Fearnley et al. (1997) Blood 89:3708-3716; Mannering et al. (1988) J. Immunol. Met. 219:69-83; Hock et al. (1999) Tiss. Antigens 53:320-334; and Hock et al. Immunol. 83:573-581.

Functional CD1a$^+$ DCs are typically generated ex vivo from monocytes and from CD34$^+$ hematopoietic progenitor cells. Bender et al. (1996) J. Immunol. Met. 196:121-135; Pickl et al. (1996) J. Immunol. 157:3850-3859; Romani et al. (1994) J. Exp. Med. 180:83-93; Sallusto et al. (1994) J. Exp. Med. 179:1109-1118; Caux et al. (1992) Nature 360:258-261; Mackensen et al. (1995) Blood 86:2699-2707; Szabolcs et al. (1995) J. Immunol. 154:5851-5861; Herbst et al. (1996) Blood 88:2541-2548; de Wynter et al. (1998) Stem Cells 16:387-396; Strunk et al. (1996) Blood 87:1292-1302 U.S. Pat. Nos. 6,010,905; and 6,004,807. It is not known if DCs generated in vitro from monocytes and hematopoietic progenitor cells retain or obtain all of the characteristics of in vivo DCs.

In addition, several attempts to generate mAb specific for human DC have failed, yielding only mAb that bind antigens expressed by both DC and other leukocytes. Human DC share a large number of immunogenic cell surface structures with other blood cells, including HLA molecules, CD18, CD29, CD31, CD43, CD44, CD45, CD54, and CD58. These antigens may dominate the immune response to injected DC to a level where B cells with specificity for DC-specific antigens are not at all or only very rarely represented among B cells that have the capability to fuse with myeloma cells.

Many investigators have tried to overcome this problem by injecting adult mice with non-DC and cyclophosphamide, in order to ablate B cells with specificity for shared antigens, or by injecting neonatal mice with non-DC, in order to tolerize B cells with specificity for shared antigens. O'Doherty et al. (1993) Adv. Exp. Med. Biol. 329:165-172; and Yamaguchi et al. (1995) J. Immunol. Met. 181:115-124.

A mAb designated CMRF44 has been used to monitor DCs in stem cell transplant patients. Fearnley et al. (1999) Blood 93:728-736. These CMRF44$^+$ cells were proposed to be suitable for use in initiating, maintaining and directing immune responses. Fearnley et al. (1997). DCs have been isolated most often by using a combination of cell surface markers. For instance, U.S. Pat. No. 5,972,627 describes "hematopoietic cells enriched for human hematopoietic dendritic progenitor cells" as having "at least 80% expressing CD34, CD45RA, and CD10 but not CD19, CD2, CD3, CD4, CD8, CD20, CD14, CD15, CD16 CD56 and glycophorin."

Isolation of DCs from blood relies on a multitude of immunophenotypic criteria, like the absence of a panel of leukocyte lineage (lin)-specific antigens (e.g. CD3, CD 14, CD19 and CD56) and the presence of HLA-DR, CD4 or CD33. Romani et al. (1996) J. Immunol. Met. 196:137-151; Thomas et al. (1993) J. Immunol. 150:821-834; Thomas et al. (1994) J. Immunol. 153:4016-4028; O'Doherty et al. (1994) Immunol. 82:487-493; O'Doherty et al. (1993) J. Exp. Med. 178:1067-1076; Nijman et al. (1995) J. Exp. Med. 182:163-174; Ferbas et al. (1994) J. Immunol. 152:4649-4662; Heufler et al. (1996) Eur. J. Immunol. 26:659-668; Ito et al. (1999) J. Immunol. 163:1409-1419; Cella et al. (1999) Nature Med. 5:919-923; Robinson et al. (1999) Eur. J. Immunol. 29:2769-2778; Olweus et al. (1997) Proc. Natl. Acad. Sci. USA 94:12551-12556; Robert et al. (1999) J. Exp. Med. 189:627-636; and Kohrgruber et al. (1999) J. Immunol. 163:3250-3259.

From analyses of DC isolated-from non-cultured blood it became evident that blood DC are not a homogeneous cell population but a mixture of at least two populations. Thomas et al. (1994); O'Doherty et al. (1994); Ito et al. (1999); Cella et al. (1999); Robinson et al. (1999); Olweus et al. (1997); Kohrgruber et al. (1999); Strobl et al. (1998) J. Immunol. 161:740-748; and Rissoan et al. (1999) Science 283:1183-1186. The first blood DC subpopulation is CD123$^{bright}$CD11c$^-$ DC, which possesses a plasmacytoid morphology and potent T cell stimulatory function. The second blood DC subpopulation is CD123$^{dim}$ CD11c$^{bright}$, which is rather monocytoid in appearance, expresses CD45RO and spontaneously develops into typical mature DCs even when cultured without any exogenous cytokines. Plasmacytoid CD123$^{bright}$ CD11c$^-$ DC display some features, like the expression of the pre-T cell receptor α chain, which indicate that they may arise from lymphoid precursors. Strobl et al. (1998); Rissoan et al. (1999); and Bruno et al. (1997) J. Exp. Med. 185:875-884. CD123$^{dim}$ CD11c$^{bright}$ DC display all the criteria of myeloid DCs. O'Doherty et al. (1994); and Ito et al. (1999). Robinson et al. (1999); Kohrgruber et al. (1999); and Strobl et al. (1998). DCs resembling plasmacytoid CD123$^{bright}$CD11c$^-$ DC have been detected in the T cell-rich areas of lymphoid tissue and were initially erroneously designated plasmacytoid T cells or plasmacytoid monocytes due to their morphology and phenotype. Grouard et al. (1997) J. Exp. Med. 185:1101-1111; Lennert et al. (1975) Lancet 1:1031-1032; Lennert et al. (1984) in Leukocyte Typing. Human Leukocyte differentiation antigens detected by monoclonal antibodies. Bernard et al. eds. Springer-Verlag, Berlin; and Facchetti et al. (1988) Am. J. Pathol. 133:15. DCs resembling CD123$^{dim}$CD11c$^{bright}$ blood DC have been found in the dark and light zone of germinal centers. Grouard (1996) Nature 384:364-367.

Splice Variants

Estimates of the total number of expressed genes range from 40,000 to more than 150,000. This number is not an accurate reflection of the number of proteins encoded since, in many cases, more than one splice variant from the mRNAs (transcriptome) produced from these genes. Estimates again vary, but perhaps as many as 500,000 different mRNAs are produced in the human. It is estimated that at least 30% of the human genes have several splice variants. Mironov et al. (1999) Genome Research 9:1288-1293). These numbers are believed by some to be conservative. Similar numbers are believed to be true for mouse and rat and alternative splicing occurs also in lower organisms, such as *Drosophila melanogaster* and *Caenorhabditis elegans*. Proteins translated from different splice variants can have significantly different functions, as evidenced by a growing number of research papers. Different splice variants may be expressed in different tissues, different developmental stages and different disease states.

C-Type Lectins

C-type lectins are a family of glycoproteins that exhibit amino acid sequence similarities in their carbohydrate recognition domains (CRD) and that bind to selected carbohydrates in a Ca$^{2+}$-dependent manner. C-type lectins have been subdivided into four categories (Vasta et al., 1994; and Spiess 1990). The first group comprises type II membrane-integrated proteins, such as asialoglycoprotein receptors, macrophage galactose and N-acetyl glucosamine (GlcNac)-specific lectin, and CD23 (Fc$_\epsilon$RII). Many members in this group exhibit specificity for galactose/fucose, galactosamine/Gal-Nac or GlcNac residues. The second group includes cartilage and fibroblast proteoglycan core proteins. The third group includes the so-called "collectins" such as serum mannose-binding proteins, pulmonary surfactant protein SP-A, and conglutinin. The fourth group includes certain adhesion molecules known as LEC-CAMs (e.g., Mel-14, GMP-140, and ELAM-1).

C-type lectins are known to function as agglutinins, opsonins, complement activators, and cell-associated recognition molecules (Vasta et al. 1994; Spiess 1990; and Kery 1991). For instance, macrophage mannose receptors serve a scavenger function (Shepherd et al., 1990), as well as mediating the uptake of pathogenic organisms, including *Pneumocystis carinii* (Ezekowitz et al. 1991) and *Candida albicans* (Ezekowitz et al. 1990). Serum mannose-binding protein mimics Clq in its capacity to activate complement through the classical pathway. Genetic mutations in this lectin predispose for severe recurrent infections, diarrhea, and failure to thrive (Reid et al. 1994). Thus, C-type lectins exhibit diverse functions with biological significance.

Carbohydrate moieties do not necessarily serve as "natural" ligands for C-type lectins. For example, CD23 (FC$_\epsilon$RII), which belongs to the C-type lectin family as verified by its binding of Gal-Gal-Nac (Kijimoto-Ochiai et al. 1994) and by its CRD sequence, is now known to recognize IgE in a carbohydrate-independent manner; an enzymatically deglycosylated form of IgE as well as recombinant (non-glycosylated) IgE produced in *E. coli* both bind to CD23 (Vercelli et al. 1989). Thus, some C-type lectins recognize polypeptide sequences in their natural ligands.

Several C-type lectins have been identified on the surface of DCs. First, Jiang et al. cloned the protein recognized by the NLDC-145 mAb, one of the most widely used mAb against murine DC (Jiang et al., 1995). This protein, now termed DEC-205, was found to be a new member of the C-type lectin family, one that contains ten distinct CRD. Second, Sallusto et al. reported that human DC express macrophage mannose receptors (MMR), which also contain multiple CRD (Sallusto et al., 1995). Both receptors have been proposed to mediate endocytosis of glycosylated molecules by DC, based on the observations that: a) polyclonal rabbit antibodies against DEC-205 not only bound to DEC-205 on DC surfaces, but were subsequently internalized; b) these DC activated effectively a T cell line reactive to rabbit IgG; and c) internalization of FITC-dextran by DC was blocked effectively with mannan, a mannose receptor competitor (Jiang et al. 1995; and Sallusto et al. 1995). With respect to cell type specificity, DEC-205 is now known to be also expressed, albeit at lower levels, by B cells and epithelial cells in thymus, intestine, and lung (Witmer-Pack et al. 1995; and Inaba et al. 1995) and MMR is also expressed even more abundantly by macrophages (Stahl 1992). Other have also been found on DC surfaces, these include DCIR, MDL-1, NURPIA,Dectin-1, Dectin-2, CLEC-1, CLEC-2, Langerin; and DC-sign.

Allergies

Allergic responses, including those of allergic asthma and allergic rhinitis, are characterized by an early phase response, which occurs within seconds to minutes of allergen exposure and is characterized by infiltration of eosinophils into the site of allergen exposure. Specifically, during the early phase of the allergic response, activation of Th2-type lymphocytes stimulates the production of antigen-specific IgE antibodies which in turn triggers the release of histamine and other mediators of inflammation from mast cells and basophils.

During the late phase response, IL-4 and IL-5 production by CD4+ Th2 cells is elevated. These cytokines appear to play a significant role in recruiting eosinophils into the site of allergen exposure, where tissue damage and dysfunction result.

Currently, antigen immunotherapy for allergic disorders involves the subcutaneous injection of small, but gradually, increasing amounts, of antigen in a process called desensitization therapy. Antigen immunotherapy is merely palliative and, at present, not curative. Weber (1997) JAMA 278:1881-1887; Stevens (1998) Acta Clinica Beligica 53:66-72; and Canadian Society of Allergy and Clinical Immunology (1995) Can. Med. Assoc. J. 152:1413-1419.

Many patients who begin the therapy do not complete the regimen, and if injections are missed for over a week, the patient must begin the entire treatment regimen again. A variety of antigens have been identified and produced by recombinant means. For reviews, see Baldo et al. (1989) Allergy 44:81-97; Baldo (1991) Curr. Opin. Immunol. 3:841-850; Blaser (1994) Ther. Umsch 51:19-23; and Valenta et al. (1996) Adv. Exp. Med. Bio. 409:185-196.

Antigen immunotherapy treatments present the risk of inducing potentially lethal IgE-mediated anaphylaxis and do not address the cytokine-mediated events of the allergic late phase response. This therapy has been described as "having the potential for misadventure." Weber (1997). Another significant problem with antigen immunotherapy is that the risk of adverse reactions, especially anaphylaxis, significantly reduces the dosage of antigen both with respect to the amount given per administration and the amount given over a period of time. Thus, traditional allergy immunotherapy is protracted and thus time-consuming, inconvenient, and expensive.

An alternative approach for treatment of IgE-associated disorders such as allergies involves administration of compounds that inhibit histamine release. Many such drugs are available as over-the-counter remedies. Other drugs include an anti-IgE binding antibody. However, a drawback of this approach is that it merely masks the symptoms, while not-providing any kind of permanent cure or protection.

BRIEF DESCRIPTION OF THE INVENTION

The invention relates to methods of enriching for hematopoietic cell populations enriched in DCs and subsets thereof. Compositions enriched for the cells and populations of cells obtained therefrom are also provided by the invention. Methods of making genetically modified DCs are also provided. Compositions of genetically modified DCs are also provided. Methods of use of the cells are also included. Antigen-binding fragments specific for BDCA-2 and BDCA-3 and the antigens recognized thereby are also provided.

The invention encompasses antigen-binding fragments specific for a subset of DCs specifically recognized by an antibody designated AC144, AD5-1311, AD5-20E5, AD5-17F6, AD5-4B8, AD5-5E8, AD5-14H12 or AD5-8E7. The invention encompasses antigen-binding fragments specific for an epitope of an antigen designated BDCA-2 (SEQ ID NO:2). The invention encompasses antigen-binding fragments specific for an epitope of an antigen designated BDCA-3.

The invention encompasses a substantially isolated or concentrated DC population or subpopulation specifically recognized by an antigen-binding fragment of the invention. These antigen-binding fragments can be any one of AC144, AD5-1311, AD5-20E5, AD5-17F6, AD5-4B8, AD5-5E8, AD5-14H12 or AD5-8E7 or antigen-binding fragments specific for BDCA-1, BDCA-2, BDCA-3 or BDCA-4. Antigen-binding fragments recognizing neuropilin-1 also recognize BDCA-4 and are suitable for use herein.

The invention further encompasses populations or subpopulations of DCs wherein substantially all of the cells express or are isolated, concentrated or enumerated on the basis of expression of at least one of BDCA-1, BDCA-2, BDCA-3 and BDCA-4. These cells can be suspended in any physiologically acceptable excipient. Preferably, the excipient is pharmacologically acceptable.

The invention further encompasses methods for obtaining compositions of hematopoietic cells enriched for DCs by separating a mixture of human hematopoietic cells into a fraction wherein at least 80% of the cells in the fraction are BDCA-1$^+$.

The invention further encompasses methods for obtaining compositions of hematopoietic cells enriched for DCs by separating a mixture of human hematopoietic cells into a fraction wherein at least 80% of the cells in the fraction are BDCA-2$^+$.

The invention further encompasses methods for obtaining compositions of hematopoietic cells enriched for DCs by separating a mixture of human hematopoietic cells into a fraction wherein at least 80% of the cells in the fraction are BDCA-3$^+$.

The invention further encompasses methods for obtaining compositions of hematopoietic cells enriched for DCs by separating a mixture of human hematopoietic cells into a fraction wherein at least 80% of the cells in the fraction are BDCA-4$^+$.

The invention further encompasses methods for isolating a substantially pure subset of DCs by a) obtaining a mixture of human hematopoietic cells; and b) substantially isolating cells from the mixture specifically recognized by an antigen-binding fragment specific for the antigen designated BDCA-2.

The invention further encompasses methods for isolating a substantially pure subset of DCs by a) obtaining a mixture of human hematopoietic cells; and b) substantially isolating cells from the mixture specifically recognized by an antigen-binding fragment specific- for the antigen designated BDCA-3.

The invention further encompasses methods for isolating a substantially pure subset of DCs by a) obtaining a mixture of human hematopoietic cells; and b) substantially isolating cells from the mixture specifically recognized by an antigen-binding fragment specific for the antigen designated BDCA-4.

The invention further encompasses methods for enumerating DCs by: a) obtaining a mixture of cells; and b) labeling the cells with an antigen-binding fragment specific for any one or more of the antigens BDCA-1, BDCA-2, BDCA-3, and BDCA-4.

The invention further encompasses methods of modulating the immune capacity of DCs by: isolating a substantially pure population or subpopulation of DCs; and modulating the calcium mobilization of the DCs.

The invention further encompasses methods of screening for test agents for the presence of pharmaceutically effective agents by isolating a substantially pure population or subpopulation of DCs with an antigen-binding fragment specific for any one or more of the antigens BDCA-1, BDCA-2, BDCA-3, and BDCA-4; screening the isolated cells with test agents; monitoring the response of the cells to the agents; comparing the response of the cells-to the agents to cells exposed to a control agent; and determining whether the test agent modulated any one immunologic properties of the isolated cell.

The invention further encompasses methods of modulating an immunologic property of DCs by altering the ability of the DC to mobilize calcium.

The invention further encompasses immunogenic and immunomodulating compositions of DCs preferably in a physiologically acceptable excipient.

The invention further encompasses methods of treating a physiologic condition by administering to a subject in need thereof an effective amount of immunogenic or immunomodulating compositions of DCs.

The invention further encompasses methods of producing DC cytokines by isolating a substantially pure population or subpopulation of DCs with an antigen-binding fragment specific for any one or more of BDCA-1, BDCA-2, BDCA-3, and BDCA-4; and isolating cytokines from the cells or cellular products or supernatants.

The invention further encompasses methods of modulating DC cytokine production by isolating a substantially pure population or subpopulation of DCs with an antigen-binding fragment specific for any one or more of BDCA-1, BDCA-2, BDCA-3, and BDCA-4; and treating the cells with agents that modulate DC cytokine production.

The invention further encompasses methods of modulating in vivo DC cytokine production by administering to a subject in need thereof an effective amount of an agent that modulates DC cytokine production.

The invention further encompasses methods of generating antibodies specific for an antigen by administering to a subject in need thereof an effective amount of a substantially pure population or subpopulation of DCs loaded with the antigen and isolated with an antigen-binding fragment specific for any one or more of BDCA-1, BDCA-2, BDCA-3, and BDCA-4 wherein the DCs-are modulated to induce a Th2 response.

The invention further encompasses methods of generating a T cell or humoral immune response specific for an antigen by administering to a subject in need thereof an effective amount of a substantially pure population or subpopulation of DCs loaded with the antigen and isolated with an antigen-binding fragment specific for any one or more of BDCA-1, BDCA-2, BDCA-3, and BDCA-4 wherein the cells are modulated to induce a Th1 response.

The invention further encompasses polypeptides prepared by expressing, in a recombinant host cell, the polypeptides and purifying the expressed polypeptide away from total recombinant host cell components, wherein the polypeptide contains about 5 contiguous amino acid residues from SEQ ID NO:2.

The invention further encompasses of purified polypeptides and compositions thereof, wherein the polypeptide contains about 5 contiguous amino acid residues from SEQ ID NO:2.

The invention further encompasses fusion proteins of a polypeptide amino acid sequence linked to a polypeptide amino acid sequence that is not SEQ ID NO: 2, wherein the amino acid sequence contains about 5 contiguous amino acid residues from SEQ ID NO:2.

The invention further encompasses polypeptides containing at least one splice variant of BDCA-2.

The invention further encompasses a polynucleotide or a complement thereof encoding at least 5 contiguous amino acid residues of BDCA-2, a splice variant or a fragment thereof The invention further encompasses recombinant host cells containing a poly-nucleotide or a complement thereof encoding at least 5 contiguous amino acid residues of BDCA-2, a splice variant or a fragment thereof.

The invention further encompasses a method of inhibiting an interaction of a DC with a T cell by contacting a composition containing DC and T cells with an effective amount of an agent that inhibits the interaction of BDCA-2, BDCA-3, or BDCA-4 with the T cell.

The invention further encompasses a method of treating inflammation by administering to a subject in need thereof an amount of an agent that inhibits the interaction of BDCA-2, BDCA-3, or BDCA-4 with the T cell effective to reduce inflammation in the subject.

The invention further encompasses a method of suppressing the expression of BDCA-2 in a cell by expressing a BDCA-2 antisense polynucleotide in the cell.

The invention further encompasses a transgenic animal containing the polynucleotide or a complement thereof encoding at least 5 contiguous amino acid residues of BDCA-2, a splice variant or a fragment thereof.

BRIEF DESCRIPTION OF THE DRAWINGS

FIG. 1 shows dot plots from the flow cytometric analysis of peripheral blood mononuclear cells (PBMC) isolated by Ficoll-Paque density gradient centrifugation. In FIG. 1, expression of BDCA-2, BDCA-3 and CD1c (BDCA-1) on PBMC is shown.

FIG. 1A shows staining of PBMC with FITC-conjugated mAb against BDCA-2 (AC144), BDCA-3 (AD5-5E8) and CD1c (AD5-8E7), and PE-conjugated mAb against the TCRαβ heterodimer, CD14, CD19 and CD56, respectively. The numbers indicate the percentage of cells in the respective quadrant. Propidium iodide fluorescence and light scatter signals were used for gating of live cells.

FIG. 1B shows the scatter profile of (a) PBMC, (b) gated BDCA-$2^+$ cells, (c) gated BDCA-$3^+$ cells and (d)-gated CD1c$^+$ cells.

FIG. 12 depicts the cDNA sequence of BDCA-2 (SEQ ID NO: 1).

FIG. 13 shows intracellular $Ca^{2+}$ mobilization is induced in immunomagnetically purified BDCA-$2^+$ BDCA-$4^+$ blood DC (A, B) and BDCA-2-transfected U937 cells (1D), but not in non-transfected U937 cells (E) via anti-BDCA-2 mAb alone (A) and or anti-BDCA-2 plus crosslinking secondary mAb (B, D, E). Ligation of BDCA-4 on immunomagnetically purified BDCA-$2^+$ BDCA-$4^+$ BDC with anti-BDCA-4 mAb and cross-linking secondary mAb does not induce intracellular $Ca^{2+}$ mobilization. Shown is the $Ca^{2+}$-dependent 405 nm/525 nm ratio of Indo-1-fluorescence (Y-axis) against time (X-axis, a value of 1024 corresponds to 204,80 sec). A is BDCA-2+BDCA-4+ blood DC, anti-BDCA-2 (AC144, IgG1). B is BDCA-2+ BDCA-4+ blood DC, anti-BDCA-2 (AC144, IgG1) plus rat anti-mouse IgG1 (X56). C is BDCA-2+ BDCA-4+ blood DC, anti-BDCA-4 (AD5-17F6, IgG1) plus rat anti-mouse IgG1 (X56). D is BDCA-2 transfected U937 cells, anti-BDCA-2 (AC144, IgG1) plus rat anti-mouse IgG1 (X56). E is non-transfected U937 cells, anti-BDCA-2 (AC144, IgG1) plus rat anti-mouse IgG1 (X56).

FIG. 14 shows ligation of BDCA-2 but not of BDCA-4 with a specific mAb followed by a secondary cross-linking mAb inhibits secretion of type I interferon by plasmacytoid BDCA-2+BDCA-4+ DC from blood or tonsils in response to stimulation with influenza virus strain PR8. Plasmacytoid BDCA-2+BDCA-4+ DC from freshly isolated blood (A) or tonsils (B) were cultured for 24 hours in the presence of IL-3 alone (control); IL-3, anti-BDCA-2 mAb and rat anti-mouse IgG1 mAb (AC144+RamG1); IL-3; anti-BDCA-2 mAb, rat anti-mouse IgG1 mAb, and influenza virus strain PR8 (AC144+RamG1+FLU); IL-3 and influenza virus strain PR8 (FLU); IL-3, anti-cytokeratin mAb, rat anti-mouse IgG1 mAb, and influenza virus strain PR8 (CK3+RamG1+FLU); IL-3, anti-BDCA-4 mAb, rat anti-mouse IgG1 mAb, and influenza virus strain PR8 (17F6+RamG1+FLU). Secreted type I interferon (U/ml) in the culture supernatants was measured by a bioassay with reference to a standard type I interferon (U/ml) curve.

FIG. 22 shows an alignment of the mRNA sequences of BDCA-2 (SEQ ID NO: 1) and mouse Dectin-2 (SEQ ID NO:3) with the precise positions of the deduced introns indicated.

FIG. 23 shows the alignment of the amino acid sequences of human BDCA-2 (SEQ ID NO:2), human DCIR (SEQ ID NO:5) and mouse Dectin-2 (SEQ ID NO:4). In FIG. 23, * represents identical conserved residues in all the aligned sequences,: represents conserved substitutions, represents semi-conserved substitutions, shaded areas denote the conserved carbohydrate recognition domain (CRD), italics show putative transmembrane domains. The following symbols highlight residues strongly conserved between C-type lectins in the CRD:

| | |
|---|---|
| H | hydrophobic |
| A | Aliphatic |
| C | Cysteine |
| G | Glycine |
| E | glutamic acid |
| W | tryptophan |
| Δ | aromatic amino acid |
| + | residues involved in calcium-dependent binding of carbohydrates |
| +P++ | region determining carbohydrate-binding specificity |

Figure 24:
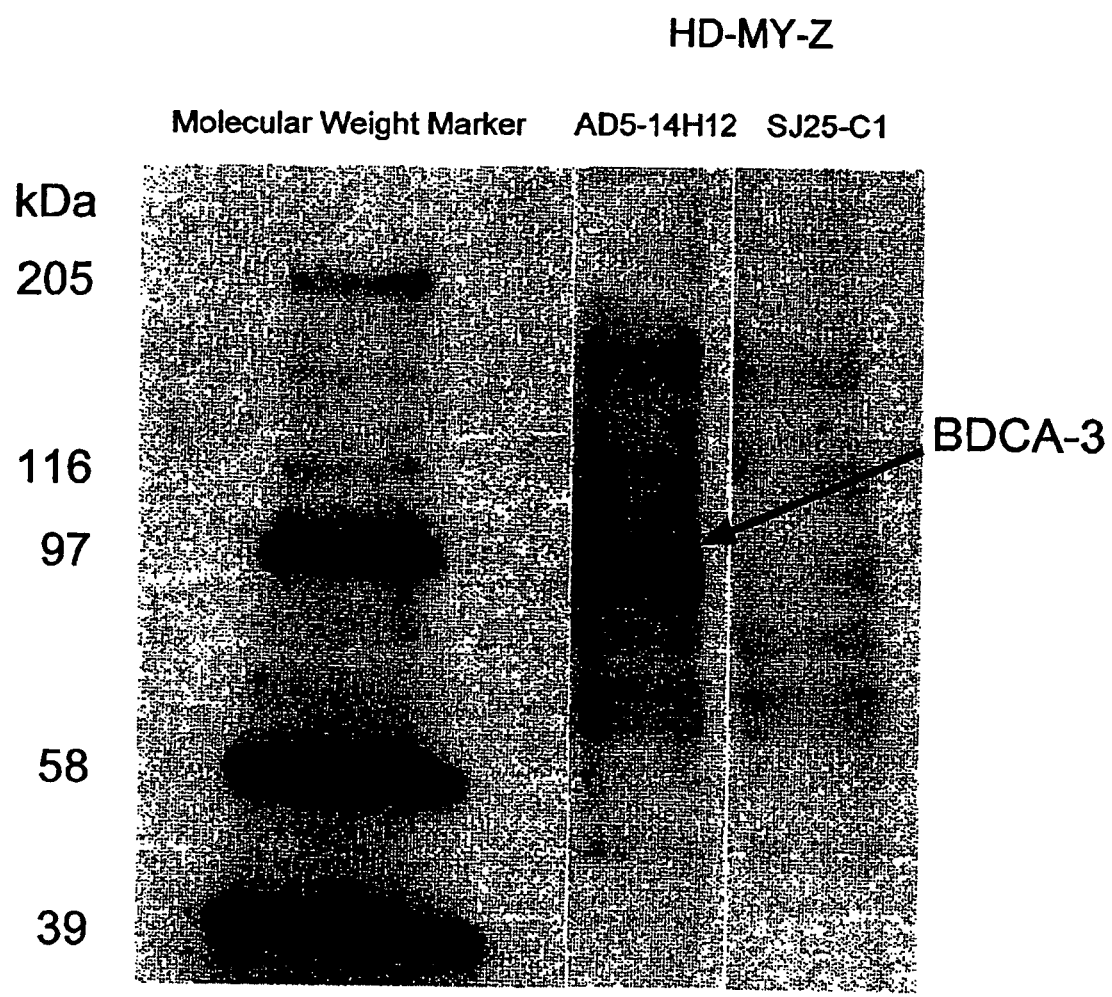

FIG. 24 shows BDCA-3 immunoprecipitated from cell lysates of surface biotinylated HD-MY-Z cells with the BDCA-3-specific mAb AD5-14H12 (IgG1). For control of specificity, the CD19-specific mAb SJ25-C1 (IgG1) was used. Precipitated proteins were analyzed by SDS-PAGE (4-12%) and Western blotting with streptavidin-peroxidase. Note that the BDCA-3-specific mAb AD5-14H12 specifically immunoprecipitates a cell surface protein of about 100 kD from HD-MY-Z cells. Thus, BDCA-3 has an apparent molecular weight of 100 kD.

Sequence identifiers are assigned as follows:
SEQ ID NO: 1 refers to human BDCA-2 cDNA sequence.
SEQ ID NO: 2 refers to mouse BDCA-2 amino acid sequence.
SEQ ID NO: 3 refers to mouse Dectin-2 cDNA sequence.
SEQ ID NO: 4 refers to mouse Dectin-2 cDNA sequence.
SEQ ID NO: 5 refers to human DCIR amino acid sequence.
SEQ ID NO: 6 refers to basic unit of a linking peptide (GGGGS).
SEQ ID NO: 7 refers to BDCA-2 forward primer (ttgaaagaac cacacccga aagt).
SEQ ID NO: 8 refers to BDCA-2 reverse primer (tagctttcta caacggtgga tgcc).
SEQ ID NO: 9 refers to BDCA-2 ASN glycosylation domain (NCSV).
SEQ ID NO: 10 refers to BDCA-2 ASN glycosylation domain (NSSY).
SEQ ID NO: 11 refers to BDCA-2 ASN glycosylation domain (NVTF).
SEQ ID NO: 12 refers to Dectin-2 ASN glycosylation domain (NESL).
SEQ ID NO: 13 refers to DCIR ASN glycosylation domain (NESS).
SEQ ID NO: 14 refers to BDCA-2 cAMP- and cGMP-dependent protein kinase phosphorylation site domain (KRLS).
SEQ ID NO: 15 refers to DCIR cAMP- and cGMP-dependent protein kinase phosphorylation site domain (KKTT).
SEQ ID NO: 16 refers to BDCA-2 Casein kinase II phosphorylation site domain (TREE).
SEQ ID NO: 17 refers to BDCA-2 Casein kinase II phosphorylation site domain (SSEE).
SEQ ID NO: 18 refers to Dectin Casein kinase II phosphorylation site domain (STKE).
SEQ ID NO: 19 refers to Dectin Casein kinase II phosphorylation site domain (STSE).
SEQ ID NO: 20 refers to Dectin Casein kinase II phosphorylation site domain (TEAE).
SEQ ID NO: 21 refers to Dectin Casein kinase II phosphorylation site domain (SICE).
SEQ ID NO: 22 refers to DCIR Casein kinase II phosphorylation site domain (TYAE).
SEQ ID NO: 23 refers to DCIR Casein kinase II phosphorylation site domain (TTKE).
SEQ ID NO: 24 refers to DCIR Casein kinase II phosphorylation site domain (TTLE).
SEQ ID NO: 25 refers to DCIR Casein kinase II phosphorylation site domain (SWQD).
SEQ ID NO: 26 refers to DCIR Casein kinase II phosphorylation site domain (SEKD).
SEQ ID NO: 27 refers to DCIR Casein kinase II phosphorylation site domain (TQEE).
SEQ ID NO: 28 refers to DCIR Casein kinase II phosphorylation site domain (SDPE).
SEQ ID NO: 29 refers to DCIR Casein kinase II phosphorylation site domain (SVCE).
SEQ ID NO: 30 refers to BDCA Tyrosine kinase phosphorylation site domain (KLREYQQY).
SEQ ID NO: 31 refers to mouse Dectin Tyrosine kinase phosphorylation site domain (RRLYELHTY).
SEQ ID NO: 32 refers to BDCA-2 Amidation site domain (GGRR).
SEQ ID NO: 33 refers to mouse Dectin N-myristylation site (GVCWTL).
SEQ ID NO: 34 refers to mouse Dectin N-myristylation site (GTMVSE).
SEQ ID NO: 35 refers to mouse Dectin N-myristylation site (GCCPNH).
SEQ ID NO: 36 refers to DCIR N-myristylation site (GINTAS).
SEQ ID NO: 37 refers to consensus immunoreceptor tyrosine-based inhibitory motif ITIM motif, (I/V) XYXX(L/V).
SEQ ID NO: 38 refers to the ITIM motif in DCIR (ITYAEV).

DETAILED DESCRIPTION OF THE INVENTION

The invention relates to methods of enriching for cell populations enriched in DCs and subsets thereof. Compositions enriched for the DCs and populations of cells obtained therefrom are also provided by the invention. Methods and compositions for modified cells are also provided. Compositions of modified cells, including genetically modified cells are also provided. Methods of use of the cells both modified and non-modified are provided. Antigen-binding fragments and the antigens recognized thereby are also provided.

Described herein is a panel of new mAb raised against immunomagnetically purified CD4$^+$lin$^-$ DC that identify three DC antigens: BDCA-2, BDCA-3 and BDCA-4. BDCA-2 and BDCA-3 are novel. In the case of BDCA-4, while not previously described as a DC-specific antigen, the antigen has been identified as neuropilin-1, a receptor for the collapsin/semaphorin family that mediates neuronal cell guidance. He et al. (1997) Cell 90:739-751.

In non-cultured human blood, expression of BDCA-2 and BDCA-4 is strictly confined to plasmacytoid CD123$^{bright}$CD11c$^-$DC, whereas expression of BDCA-3 is restricted to a small population of CD123$^-$CD11c$^{dim}$ DC. This BDCA-3$^+$ DC population shares many immunophenotypic features with classical CD123$^{dim}$CD11c$^{bright}$ DC, but, unlike CD123$^{dim}$CD11c$^{dim}$ DC, BDCA-3$^+$ DC lack expression of CD1c (BDCA-1), CD2 and several of the Fc receptors.

The unpurified source of DCs may be any known in the art, such as the bone marrow, fetal, neonate or adult or other hematopoietic cell source, e.g., fetal liver, peripheral blood or umbilical cord blood tonsil, lymph node, nasal membrane, spleen, skin, airway epithelia, lung, liver gut, Peyers patches, etc. DCs can also be isolated from cultured cells such as DCs derived from progenitor cells. Various techniques can be employed to separate the cells. For instance, negative selection methods can remove non-DCs initially. mAbs are particularly useful for identifying markers associated with particular cell lineages and/or stages of differentiation for both positive and negative selections.

If desired, a large proportion of terminally differentiated cells can be initially removed using a relatively crude negative separation. For example, magnetic bead separations can be used initially to remove large numbers of irrelevant cells. At least about 80%, usually at least 70% of the total cells will be removed prior to isolation of DCs. Preferably, the DC are directly isolated from the cell source by positive selection Procedures for separation include, but are not limited to, density gradient centrifugation; rosetting, coupling to particles that modify cell density; magnetic separation with antibody-coated magnetic beads or antibody-coated fero fluids (nonoporticles); affinity chromatography; cytotoxic agents joined to or used in conjunction with a mAb, including, but not limited to, complement and cytotoxins; and panning with antibody attached to a solid matrix, e.g. plate, elutriation or any other convenient technique.

Techniques providing accurate separation and analysis include, but are not limited to, magnetic bead separation and flow cytometry, which can have varying degrees of sophistication, e.g., a plurality of color channels, low angle and obtuse light scattering detecting channels, impedance channels, etc.

The cells can be selected against dead cells, by employing dyes associated with dead cells such as propidium iodide (PI). Preferably, the cells are collected in a medium comprising 2% serum, such as fetal calf serum (FCS) or, human serum albumin (HSA) or any other suitable, preferably sterile, isotonic medium. For physiologic indications, HAS is preferred. Genetic modification of the cells can be accomplished at any point during their maintenance by transducing a substantially homogeneous cell composition with a recombinant DNA construct, transfected with RNA, cell fusion, loading with antigens and various methods known in the and/or described herein.

For modification of the cells, a retroviral vector can be employed, however any other suitable vector, delivery system or cellular modification can be used. These include, e.g., adenovirus, adeno-associated virus, artificial chromosomes, derived from yeast and RNA derived from an antigen source such as a tumor. The genetic modification, if any, need not be permanent as mature DCs have a limited lifetime. Genetic approaches are used to express foreign (tumor, viral, parasitic, etc.) antigens or autoantigens in DCs in order to induce immunity or tolerance; The longevity of the modification can also be controlled by suicide genes to limit therapy (as with T cells).

Methods of transduction include any known in the art including, without limitation, direct co-culture of the cells with producer cells, e.g., by the method described by Bregni et al. (1992) Blood 80:1418-1422, or culturing with viral supernatant alone with or without appropriate growth factors and polycations, e.g., by the method described by Xu et al. (1994) Exp. Hemat. 22:223-230; and Hughes et al. (1992) J. Clin. Invest. 89:1817.

Upon reintroduction of the modified cells expressing or loaded with an antigen so as to present the antigen, into the host, T cells are activated, anergized or deleted and are specifically directed against the antigen. Generally, suitable antigens include those expressed by virally infected cells, or cancer cells, bacteria, yeast, protozoan, autoantigens (tolerogens) and allergens. More specifically, suitable antigens include, but are not limited to, viral proteins, proteins of cancer cells, tissue-specific proteins or tolerogenic proteins. "Induction" of T cells can include inactivation of antigen-specific T cells such as by deletion or anergy. Inactivation is particularly useful to establish or reestablish tolerance such as in organ transplantation and autoimmune disorders respectively. The modified DCs can be administered by any method known in the art including, but not limited to, intravenously, subcutaneously, intranodally and directly to the thymus. Preferably, administration is intravenous (IV).

Often, cell immunotherapy involves removal of bone marrow leukopheresis harvests or other source of cells from a human host, isolating the cells from the source. Meanwhile, the host may be treated to partially, substantially or completely ablate native hematopoietic capability if hematopoietic stem cell transplantation is to occur. The isolated cells can be modified during this period of time, so as to provide for cells having the desired modification. In the case of complete hematopoietic ablation, stem cell augmentation will also be required. The cells or modified cells can then be restored to the host to provide for the new capability. The methods of cell removal, host ablation and stem/progenitor cell repopulation are known in the art.

The modified cells can be administered in any physiologically acceptable vehicle, normally intravascularly, intranodal and subcutaneously. Usually, at least $1 \times 10^5$ cells will be administered, preferably $1 \times 10^6$ or more. The cells can be introduced by injection, catheter, or the like. If desired, factors can also be included, including, but not limited to, interleukins, e.g. IL-2, IL-3, IL-4, IL-12, and flt-Ligand, as well as the other interleukins, the colony stimulating factors, such as G-, M- and GM-CSF, interferons, e.g. γ-interferon.

The term "polypeptide", "peptide" and "protein" are used interchangeably herein to refer to polymers of amino acid residues of any length. The polymer can be linear or branched, it can comprise modified amino acid residues or amino acid analogs, and it can be interrupted by chemical moieties other than amino acid residues. The terms also encompass an amino acid polymer that has been modified naturally or by intervention; including, but not limited to, disulfide bond formation, glycosylation, lipidation, acetylation, phosphorylation, or any other manipulation or modification, such as conjugation with a labeling or bioactive component. Unless stated or implied otherwise, the term antigen-binding fragment includes any polypeptide monomer or polymer with immunologic specificity, including the intact antibody, and smaller and larger functionally equivalent polypeptides, as described herein.

1. Antigen-binding Fragments and Compositions Thereof

This invention encompasses antigen-binding fragments that specifically recognize DCs. That is, the antigen is found on DCs such that antigen-binding fragments that recognize the antigen preferentially recognize or bind to DCs or a subset thereof. Or, as with BDCA-4, the antigen may be found on other cell types; but within hematopoietic cells, the antigen is predominately present on DCs.

The invention further encompasses a composition of matter comprising an isolated antigen-binding fragment that binds specifically to at least one DC antigen. Preferably, the antigen-binding fragment is or is derived from a mAb designated AC144, AD5-13A11, A D5-20E5, AD5-17F6, AD5-4B8, AD5-5E8, AD5-14H12 and AD5-8E7. Table 1 shows the antigen and epitope recognized by each mAb and the isotype of the mAbs specific for DC.

TABLE 1

| Antigen | Antibody | Epitope | Isotype | CD11c$^{bright}$ CD123$^{low}$ DC | CD11c$^{low}$ CD123$^-$ DC | CD11c$^-$ CD123$^{bright}$ DC | Other leukocytes |
|---|---|---|---|---|---|---|---|
| CD1c | AD5-8E7 | 1A | IgG2a | + | − | − | B cell subset |
| BDCA-2 | AC144 | 2A | IgG1 | − | − | + | − |
| BDCA-2 | AD5-13A11 | 2A | IgG2a | − | − | + | − |
| BDCA-2 | AD5-5B8 | 2A | IgG1 | − | − | + | − |
| BDCA-3 | AD5-5E8 | 3A | IgG1 | − | + | − | − |
| BDCA-3 | AD5-14H12 | 3B | IgG1 | − | + | − | − |
| BDCA-4 | AD5-17F6 | 4A | IgG1 | − | − | + | − |

In non-cultured human blood, BDCA-2 and BDCA-4 are expressed by a CD123$^{bright}$CD11c$^-$DC population. This DC population is now commonly referred to as plasmacytoid DC. Using BDCA-2 or BDCA-4 as a surface marker for immunomagnetic isolation and/or flow cytometric identification of plasmacytoid DC, the results presented herein on frequency, immunophenotype, morphology, endocytic capacity, and maturation of these cells, were completely consistent with previous reports, where a large panel of leukocyte antigens was used. This clearly illustrates that both antigens are useful markers for plasmacytoid DC in non-cultured human blood. Stainings of tonsillar cells show (FIG. 16) that the T cell zone associated plasmacytoid DC in peripheral lymphoid organs can also be discriminated from other lymphoid tissue-associated DC populations, such as germinal center DC, interdigitating DC and follicular DC based on the expression of BDCA-2 and BDCA-4.

Unlike BDCA-2, BDCA-4 is also expressed on several in vitro differentiated DC populations: (1) in contrast to BDCA-2, BDCA-4 is expressed on both Mo-DC and CD34-DC; (2) whereas expression of BDCA-2 is completely down-regulated on plasmacytoid DC once they have undergone IL-3-mediated maturation in culture, expression of BDCA-4 is in fact up-regulated on cultured plasmacytoid DC; and (3) in contrast to BDCA-2, BDCA-4 becomes expressed within 12 h by a majority of cultured CD11c$^+$ DC, whereby it is unclear whether this is only true for the larger CD1c$^+$CD11c$^{bright}$ population or also true for the smaller CD1c$^-$CD11c$^{dim}$CD123$^-$ population. The finding that no other BDCA-4$^+$ cells than plasmacytoid DC are present in non-cultured human blood, in fact, indicates that no counterparts of the in vitro differentiated BDCA-4$^+$ DC populations mentioned above are present in blood.

Figure 15:
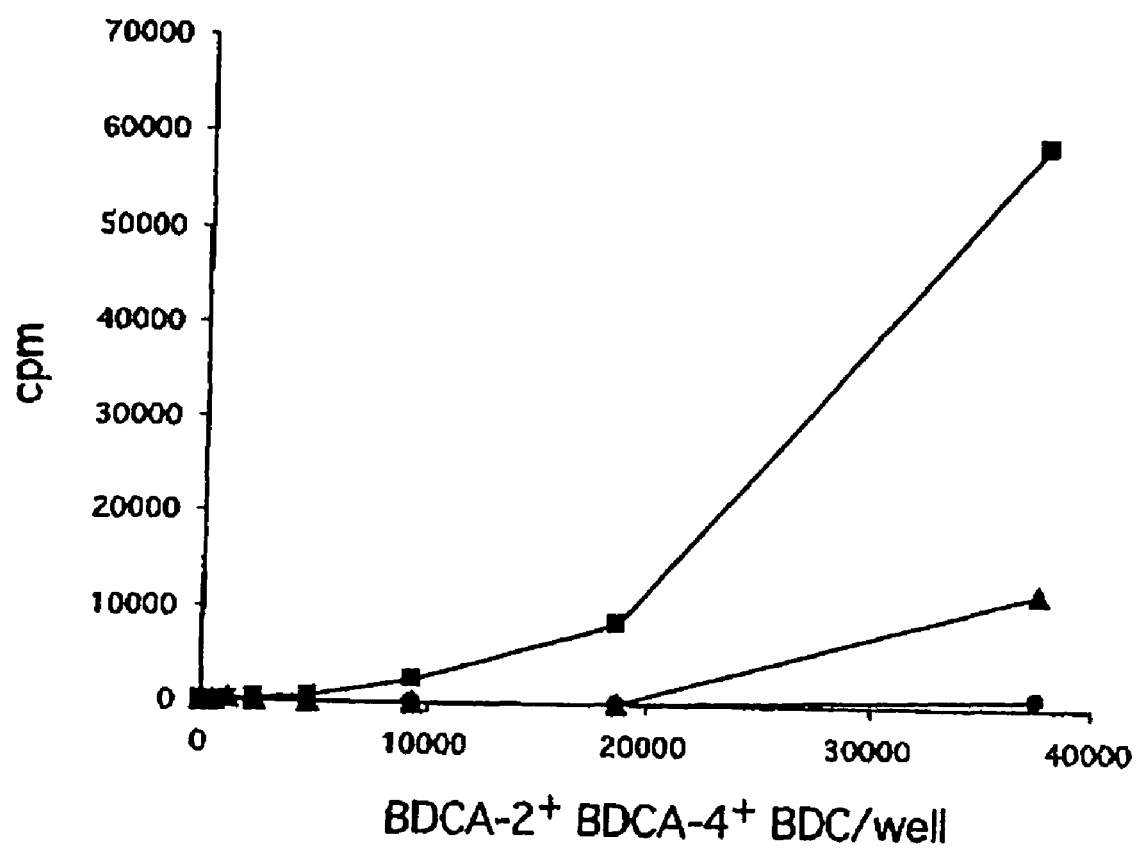
FIG. 15 shows presentation of anti-BDCA-2 mAb (AC144, IgG1) to a T cell clone specific for mouse IgG1 by isolated BDCA-2- and BDCA-4-expressing plasmacytoid DC. BDCA-2+BDCA-4+ plasmacytoid DC present anti-BDCA-2 mAb (AC144, IgG1, ■) to T cells much more efficiently than anti-ILT-3 mAb (ZM3.8, IgG1, ▲) and anti-cytokeratin mAb (CK3-11D5, IgG1, ●).

Cross-linking of BDCA-2 by means of anti-BDCA-2 mAb induces rapid internalization of the antigen-Ab complex. In analogy to other endocytic receptors on DC that are down-regulated upon maturation, like Langerin. Valladeau et al. (2000) Immunity 12:71-81. Therefore, BDCA-2 may be a receptor with antigen-capture function. BDCA-2 is a C-type lectin, is rapidly internalized after-ligation (FIG. 8), and BDCA-2 ligand(s) are processed and presented to T cells (FIG. 15). Thus, like DEC-205, BDCA-2 has an antigen uptake and presentation function for ligands to T cells.

Expression of BDCA-3 is restricted to a small population of CD1c$^-$ CD11c$^{dim}$CD123$^-$DC in non-cultured human blood. With respect to phenotype, morphology, endocytic capacity, and maturation requirements, this DC population is quite similar to the CD1c$^+$CD11c$^{bright}$CD123$^{dim}$ DC population. However, apart from BDCA-3 and CD1c expression themselves, the immunophenotypic analysis has revealed some striking differences: in contrast to CD1c$^+$ BDC, BDCA-3$^+$ BDC do not express the Fc receptors CD32, CD64 and EcoRI, and they do not express CD2. The lack of Fc receptor expression indicates that BDCA-3$^+$ BDC, unlike CD1c$^+$ BDC do not have the capability of Ig-mediated antigen uptake. Fanger et al. (1996) J. Immunol. 157:541-548; Fanger et al. (1997) J. Immunol. 158:3090-3098; and Maurer et al. (1996) J. Immunol. 157:607-616. As shown herein, BDCA-3 is a 100 kD protein.

There is evidence that CD1c$^+$CD11c$^{bright}$ DC, in contrast to CD1c$^-$ CD11c$^{dim}$ DC, have the capacity to acquire Langerhans cell characteristics (expression of Lag antigen, E-cadherin and Langerin, and presence of Birbeck granules) when cultured with GM-CSF, IL-4 and TGF-β1. If BDCA-3$^+$ DC and CD1c$^+$ DC represent maturational stages of the same cell type, this would indicate that BDCA-3$^+$ DC have either already lost or not yet acquired the capacity to differentiate into Langerhans cells.

In contradiction to the results presented herein, Ito et al. (1999) reported that CD1c$^+$CD11c$^{bright}$ DC, unlike CD1c$^-$CD11c$^{dim}$ DC, express CD1a. Two mAb BL-6 and B-B5 were used for staining of CD1a and that a difference in staining intensity was actually observed when the two mAb were compared (staining with B-B5 was probably brighter). As shown herein, staining of DC was clearly negative using optimal titers of the CD1a mAb BL-6 and HI149, but positive using B-B5. Moreover, B-B5, unlike BL-6 and HI149, stained a high proportion of CD19$^+$ B cells in blood. Thus, the staining pattern of B-B was quite reminiscent of a CD1c mAb rather than a CD1a mAb and, in fact, CD1c mAb AD5-8E7 inhibits binding of B-B5 to MOLT-4 cells. Therefore, we conclude that B-5 recognizes CD1c and that CD1c$^+$ DC do not express CD1a.

Staining of cD1c$^+$ DC for CD1c, CD2 and CD14 revealed that a minor proportion of DC expresses CD14 to a variable degree and that the level of CD1c as well as CD2 expression on these cells is inversely proportional to the level of CD14 expression. This observation is in accordance with a linear differentiation model, where CD1c$^+$CD2$^+$CD11c$^{bright}$CD14$^-$ DC are the progeny of CD14$^+$CD1c$^-$CD2$^-$ monocytes rather than the progeny of a common precursor of both cell types. This concept finds further support by the observation that a considerable proportion of CD14$^+$ monocytes already express very low levels of CD2 and have the capacity to rapidly differentiate into mature DC with typical dendritic morphology and potent T cell stimulatory function when cultured with GM-CSF and IL-4. Crawford et al. (1999) J. Immunol. 163:5920-5928.

The use of CD1c (BDCA-1), BDCA-2, BDCA-3 and BDCA-4 mAb provides a convenient and efficient way to rapidly detect, enumerate and isolate DC populations from PBMC, leukapheresis material, whole blood, tonsil, etc., without apparent functional perturbation. This is a valuable aid for their further functional and molecular characterization and can be useful in elucidating their interrelationships. Furthermore, the ability to easily isolate DC populations to homogeneity greatly facilitates their clinical use. The antigen-binding fragments are also useful in detecting, enumerating and/or isolating DCs from tissues, both non-hematopoietic tissues (including, without limitation, airway epithelia, skin, gut, lung, and liver) and hematopoietic tissues (including, without limitation, tonsil, spleen, lymph node and thymus).

Hybridomas secreting the antibodies are also encompassed by the invention as are other cells expressing antigen-binding fragments thereof. Also encompassed by the invention are any antigen-binding fragments that specifically recognize BDCA-2, or BDCA-3 or BDCA-4. As seen from Table 1 and the Examples provided herein, multiple types of mAbs can be produced which specifically recognize these antigens. As also seen from the results presented herein, the antigen-binding fragments need not recognize the same epitope on the same antigen. All such antigen-binding fragments and compositions thereof are encompassed by the invention.

The term "antigen-binding fragment" includes any moiety that binds preferentially to a DC or a sub-population thereof. Suitable moieties include, without limitation, oligonucleotides known as aptomers that bind to desired target molecules (Hermann and Pantel (2000) Science 289:820-825), carbohydrates, lectins, Ig fragments as Fab, $F(ab')_2$, Fab', scFv (both monomer and polymeric forms) and isolated H and L chains. An antigen-binding fragment retains specificity of the intact Ig, although avidity and/or affinity can be altered.

Certain compounds, compositions and methods described herein relate generally to antibodies and derivatives thereof which having provided the antigenic determinants herein, can be generated routinely by standard immunochemical techniques. These include, but are not limited to, antigen-binding fragments coupled to another compound, e.g. by chemical conjugation, or associated with by mixing with an excipient or an adjuvant. Specific conjugation partners and methods of making them are described herein and known in the art.

Antigen-binding fragments (also encompassing "derivatives" thereof) are typically generated by genetic engineering, although they can be obtained alternatively by other methods and combinations of methods. This classification includes, but is not limited to, engineered peptide fragments and fusion peptides. Preferred compounds include polypeptide fragments containing the anti-DC CDRS, antibody fusion proteins containing cytokine effector components, antibody fusion proteins containing adjuvants or drugs, antibody fusion proteins containing tumor cell-derived antigens, viral antigens, bacterial antigens, parasite antigens, yeast antigens, autoantigenis or antigenic peptides (T cell epitopes) derived therefrom, and, single chain V region proteins. Antigen-binding fragments are considered to be of human origin if they are isolated from a human source, and used directly or cloned and expressed in other cell types and derivatives thereof or whole human chromosomes or portions thereof (such as mice with human chromosomes encoding $V_H$, $D_H$, $J_H$, $V_L$, $JL_L$, $C_H$, $C_L$ gene segments).

A "fusion polypeptide" is a polypeptide comprising contiguous peptide regions in a different position than would be found in nature. The regions can normally exist in separate proteins and are brought together in the fusion polypeptide; they can normally exist in the same protein but are placed in a new arrangement in the fusion polypeptide; or they can be synthetically arranged. For instance, the invention encompasses recombinant proteins (and the polynucleotides encoding the proteins or complementary thereto) that are comprised of a functional portion of an antigen-binding fragment and another peptide such as a toxin. Methods of making these fusion proteins are known in the art and are described for instance in WO93/07286.

A "functionally equivalent fragment" of a polypeptide varies from the native sequence by any combination of additions, deletions, or substitutions while preserving at least one functional property of the fragment relevant to the context in which it is being used.

The antigen-binding fragments are useful in palliating the clinical conditions related to immunologic disorders. The invention further comprises polypeptide derivatives of the antigen-binding fragments and methods-for using these compositions in diagnosis, treatment, and manufacture of novel reagents.

The invention also encompasses antigen-binding fragments conjugated to a chemically functional moiety. Typically, the moiety is a label capable of producing a detectable signal. These conjugated antigen-binding fragments are useful, for example, in detection systems such as quantitation of DCs in various tissues, in various diseases, after stem cell transplantation, and after immunoablative therapy like chemotherapy and radiation, and imaging of DCs for instance in following chemotherapy or autoimmune therapy. Such labels are known in the art and include, but are not limited to, radioisotopes, enzymes, fluorescent compounds, chemiluminescent compounds, bioluminescent compounds, substrate cofactors and inhibitors and magnetic particles. For examples of patents teaching the use of such labels, see, for instance U.S. Pat. Nos. 3,817,837; 3,850,752; 3,939,350; 3,996,345; 4,277,437; 4,275,149; and 4,366,241. The moieties can be covalently linked, recombinantly linked, or conjugated (covalently or non-covalently) through a secondary reagent, such as a second antibody, protein A, or a biotin-avidin complex.

Other functional moieties include, without limitation, signal peptides, agents that enhance immunologic reactivity, agents that facilitate coupling to a solid support, vaccine carriers, bioresponse modifers, paramagnetic labels and drugs. Signal peptides include prokaryotic and eukaryotic forms. Agents that enhance immunologic reactivity include, but are not limited to, bacterial superantigens and adjuvants. Agents that facilitate coupling to a solid support include, but are not limited to, biotin, avidin or derivatives thereof. Immunogen carriers include, but are not limited to, any physiologically acceptable buffer. Bioresponse modifiers include, but are not limited to, cytokines, particularly tumor necrosis factor (TNF), IL-2, interleukin-4 (IL-4), GM-CSF; IL-10, IL-12, TGF-β and certain interferons, and chemokines (MIP-3β, SDF-1, Lymphotactin, DC-CK1, Eotaxins, IP-10, TARC, Rantes, MIP-1×, MIP-1B, SLC, 1-TAC, MIG, MDC, MCP-1, TCA-3, MCP-2, -3, -1. See also, U.S. Pat. No. 5,750,119; and WO patent publications: 96/10411; 98/34641; 98/23735; 98/34642; 97/10000; 97/10001; and 97/06821. Such, chemokines may be useful to attract other cells such as T cells.

A "signal peptide" or "leader sequence" is a short amino acid sequence that directs a newly synthesized protein through a cellular membrane, usually the endoplasmic reticulum (ER) in eukaryotic cells, and either the inner membrane or both inner and outer membranes of bacteria. Signal peptides are typically at the N-terminus of a polypeptide and are removed enzymatically between biosynthesis and secretion of the polypeptide from the cell or through the membrane of the ER. Thus, the signal peptide is not present in the secreted protein but is present only during protein production.

Immunotoxins, including single chain conjugates, can be produced by recombinant means. Production of various immunotoxins is well known in the art, and methods can be found, for example, in "Monoclonal Antibody-toxin Conjugates: Aiming the Magic Bullet," Thorpe et al. (1982) Monoclonal Antibodies in Clinical Medicine, Academic Press, pp. 168-190; Vitatta (1987) Science 238:1098-1104; and Winter and Milstein (1991) Nature 349:293-299. Suitable toxins include, but are not limited to, ricin, radionuclides, pokeweed antiviral protein, Pseudomonas exotoxin A, diphtheria toxin, ricin A chain, fungal toxins such as fungal ribosome inactivating proteins such as gelonin, restrictocin and phospholipase enzymes. See, generally, "Chimeric Toxins," Olsnes and Pihl, Pharmac. Ther. 15:355-381 (1981); and "Monoclonal Antibodies for Cancer Detection and Therapy," eds. Baldwin and Byers, pp. 159-179, 224-266, Academic Press (1985).

The chemically functional moieties can be made recombinantly for instance by creating a fusion gene encoding the antigen-binding fragment and functional regions from other genes (e.g. enzymes). In the case of gene fusions, the two components are present within the same gene. Alternatively, antigen-binding fragments can be chemically bonded to the moiety by any of a variety of well known chemical procedures. For example, when the moiety is a protein, the linkage can be by way of homo- or hetero-bifunctional cross linkers, e.g., SPDP, SMCC, carbodiimide glutaraldehyde, or the like. The moieties can be covalently linked, or conjugated, through a secondary reagent, including, but not limited to, a second antibody, protein A, or a biotin-avidin complex. Paramagnetic moieties and the conjugation thereof to antibodies are well-known in the art. See, e.g., Miltenyi et al. (1990) Cytometry 11:231-238.

Here, we overcame problems described in the art (O'Doherty et al. (1993); and Yamaguchi et al. (1995)) with a recently described contralateral footpad immunization procedure. Yin et al. (1997) Blood 90:5002-5012. This system utilizes naive antigen-specific T and B cells which continuously recirculate among peripheral lymphoid organs as long as they do not encounter antigen, but become immediately retained within a peripheral lymphoid organ for several days, if not weeks, once they are activated by antigen. Picker et al. (1992) Annu. Rev. Immunol. 10:561-591; Butcher et al. (1996) Science 272:60-66; Bradley et al. (1996) Curr. Opin. Immunol. 8:312:320; Watson et al. (1998) Cell. Adhes. Commun. 6:105-110; Kearney et al. (1994) Immunity 1:327-339; Jacob.et al. (1992) J. Exp. Med. 176:679-687; Ridderstaad et al. (1998) J. Immunol. 160:4688-4695; and Tarlinton (1998) Curr. Opin. Immunol. 10:245-251. In the examples provided herein, the left footpads of mice were injected on days −3, 0, 4, 7, 11, and 14 with Bristol-8 B lymphoblastoma cells, while the right footpads were injected with DC on days 0, 4, 7, 11, and 14. Naïve B an T cells with specificity for shared antigens, e.g. HLA class II molecules, should become activated by Bristol-8 cells between d −3 and 0 in the left popliteal lymph node and thereupon be retained there, while all lymphocytes with specificity for antigens unique to DC should remain available for activation after d 0 in the right popliteal lymph node.

This immunization technique was combined with a powerful procedure for rapid isolation of large numbers of DC and permitted production a panel of mAb that recognize three novel DC antigens: BDCA-2, BDCA-3 and BDCA-4. The use of antigens in producing additional DC-specific antibodies allows more traditional methods of antibody production to be used with a greater chance of success.

Methods of antibody production and isolation are well known-in the art. See, for example, Harlow and Lane (1988) Antibodies: A Laboratory Manual, Cold Spring Harbor Laboratory, N.Y. General antibody purification methods include, but are not limited to, salt precipitation (for example, with ammonium sulfate); ion exchange chromatography (for example, on a cationic or anionic exchange column run at neutral pH and eluted with step gradients of increasing ionic strength); gel filtration chromatography (including gel filtration HPLC); and chromatography on affinity resins such as protein A, protein G, hydroxyapatite, or anti-Ig. Antigen-binding fragments can also be purified on affinity columns comprising DCs or an antigenic portion thereof. Preferably fragments are purified using Protein-A-CL-Sepharose™ 4B chromatography followed by chromatography on a DEAE-Sepharose™ 4B ion exchange column.

The invention also encompasses hybrid antibodies, in which one pair of H and L chains is obtained from a first antibody, while the other pair of H and L chains is obtained from a different second antibody, For purposes of this invention, one pair of L and H chains is from anti-DC antibody. In one example, each L-H chain pair binds different epitopes of a DC-specific antigen. Such hybrids can also be formed using humanized H or L chains. The invention also encompasses other bispecific antibodies such as those containing two separate antibodies covalently linked through their constant regions.

Other antigen-binding fragments encompassed by this invention are antibodies in which the H or L chain has been modified to provide additional properties. For instance, a change in amino acid sequence can result in reduced immunogenicity of the resultant polypeptide. The changes range from changing one or more amino acid residues to the complete redesign of a region such as a C region domain. Typical changes include, but are not limited to, those related to complement fixation, interaction with membrane receptors, and other effector functions. A recombinant antibody can also be designed to aid the specific delivery of a substance (such as a cytokine) to a cell. Also encompassed by the invention are peptides in which various Ig domains have been placed in an order other than that which occurs in nature.

The size of the antigen-binding fragments can be only the minimum size required to provide a desired function. It can optionally comprise additional amino acid sequence, either native to the antigen-binding fragment, or from a heterologous source, as desired. Anti-DC antigen-binding fragments can contain only 5 consecutive amino acid residues from an antibody V region sequence. Polypeptides comprising 7 amino acid residues, more preferably about 10 amino acid residues, more preferably about 15 amino acid residues, more preferably about 25 amino acid residues, more preferably about 50 amino acid residues, more preferably about 75 amino acid residues from the antibody L or H chain V region are also included. Even more preferred are polypeptides, comprising the entire antibody L or H chain V region.

Substitutions can range from changing or modifying one or more amino acid residue to complete redesign of a region, such as the V region. Amino acid residue substitutions, if present, are preferably conservative substitutions that do not deleteriously affect folding or functional properties of the peptide. Groups of functionally related amino acid residues within which conservative substitutions can be made are glycine/alanine; valine/isoleucine/leucine; asparagine/glutamine; aspartic acid/glutamic acid; serine/threonine/methionine; lysine/arginine; and phenylalanine/tyrosine/tryptophan. Antigen-binding fragments can be glycosylated or unglycosylated, can be modified post-translationally (e.g., acetylation, and phosphorylation) or can be modified synthetically (e.g., the attachment of a labeling group).

Polypeptide derivatives comprising both an L chain and an H chain can be formed as separate L and H chains and then assembled, or assembled in situ by an expression system for both chains. Such expression systems can be created by transfecting with a plasmid comprising separate transcribable regions for the L and H chain, or by co-transfecting the same cell with plasmids for each chain. In a third method, a suitable plasmid with an H chain encoding region is transfected into an H chain loss mutant.

H chain loss mutants can be obtained by treating anti-DC antibody producing cells with fluorescein-labeled rabbit anti-mouse IgG (H chain specific, DAKO Corporation, Carpinteria, Calif.) according to the supplier's instruction. The stained and unstained cell populations are analyzed by flow cytometry. Unstained cells are collected in a sterilized tube and placed in 96-well plates at 1 cell/well by limiting dilution. Culture supernatants are then assayed by ELISA using goat anti-mouse IgG (H chain specific) and goat anti-mouse kappa. Clones having a kappa-positive, IgG-negative phenotype are subcloned at least 3 times to obtain stable anti-DC$^{(-H)}$ mutants. mRNA from putative H chain loss mutants can be isolated and the sequence of the L chain V region cDNA determined. Reverse PCR of the mRNA for the $V_H$ is performed with 2 sets of 5'- and 3'-primers, and used for cloning of anti-DC$^{(-H)}$ cDNA. An H chain loss mutant yields no detectable DNA band with these primers. Transfection of the cells proceeds with a suitable H chain plasmid.

Another antigen-binding fragment derivative encompassed by this invention is an antibody in which the constant region of the H or L chain has been modified to provide additional properties. For instance, a change in amino acid sequence can result in altered immunogenicity of the resultant polypeptide. The changes range from one or more amino acid residues to the complete redesign of constant region domain. Changes contemplated affect complement fixation, interaction with membrane receptors, and other effector functions. A recombinant antibody can also be designed to aid the specific delivery of a substance (such as a lymphokine or an antigen or an antigenic peptide derived from a tumor, virus, parasite or bacteria, or tolerogen (autoantigen)) to a cell. Also encompassed by the invention are proteins in which various Ig domains have been placed in an order other than that which occurs in nature.

The invention also encompasses single chain V region fragments ("scFv") of anti-DC antibodies. Single chain V region fragments are made by linking L and/or H chain V regions by using a short linking peptide. Bird et al. (1988) Science 242:423-426. Any peptide having sufficient flexibility and length can be used as a linker in a scFv. Usually the linker is selected to have little to no immunogenicity. An example of a linking peptide is (GGGGS)$_3$ (SEQ ID NO:6), which bridges approximately 3.5 nm between the carboxy terminus of one V region and the amino terminus of another V region. Other linker sequences can also be used, and can provide additional functions, such as a for attaching to a drug or solid support or specific delivery of a substance (such as a lymphokine or an antigen or an antigenic peptide derived from a tumor, virus, parasite or bacteria, or tolerogen (autoantigen)) to a cell.

All or any portion of the H or L chain can be used in any combination. Typically, the entire V regions are included in the scFv. For instance, the L chain V region can be linked to the H chain V region. Alternatively, a portion of the L chain V region can be linked to the H chain V region, or portion thereof. Also contemplated are scFvs in which the H chain V region is from an antibody described herein, and the L chain V region is from another Ig. A biphasic, scFv can be made in which one component is an antigen-binding fragment and another component is a different polypeptide, such as a T cell epitope.

The scFvs can be assembled in any order, for example, $V_H$-(linker)-$V_L$ or $V_L$-(linker)-$V_H$. There can be a difference in the level of expression of these two configurations in particular expression systems, in which case one of these forms can be preferred. Tandem scFvs can also be made, such as (X)-(linker)-(X)-(linker)-(X), in which X are scFvs, or combinations thereof with other polypeptides. In another embodiment, single chain antibody polypeptides have no linker polypeptide, or just a short, inflexible linker. Possible configurations are $V_L$-$V_H$ and $V_H$-$V_L$. The linkage is too short to permit interaction between $V_L$ and $V_H$ within the chain, and the chains form homodimers with a $V_L/V_H$ antigen-binding site at each end. Such molecules are referred to as "diabodies."

ScFvs can be produced recombinantly or synthetically. For synthetic production of scFv, an automated synthesizer can be used. For recombinant production of scFv, a suitable plasmid-containing polynucleotide that encodes the scFv can be introduced into a suitable host cell, either eukaryotic, such as yeast, plant, insect or mammalian cells, or prokaryotic, such as *Escherichia coli*, and the expressed protein can be isolated using standard protein purification techniques. ScFvs can also be obtained from a phage display library.

A particularly useful system for the production of scFvs is plasmid pET-22b(+) (Novagen, Madison, Wis.). *Escherichia coli* pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.).

Conditions of gene expression preferably ensure that the scFv assumes optimal tertiary structure. Depending on the plasmid used (especially promoter activity), and the host cell, it can be necessary to modulate production rate. For instance, use of a weaker promoter, or expression at lower temperatures, can be necessary to optimize production of properly folded scFv in prokaryotic systems; or, it can be used to express scFv in eukaryotic cells.

The invention also encompasses polymeric forms of antigen-binding fragments, containing a plurality of DC-specific antigen-binding fragments. One embodiment is a linear polymer of antigen-binding fragments, optionally conjugated to carrier. These linear polymers can comprise multiple copies of a single antigen-binding fragment polypeptide, or combinations of different polypeptides, and can have tandem polypeptides, or polypeptides separated by other amino acid sequences.

Another embodiment is multiple antigen peptides (MAPs). MAPs have a small immunologically inert core having radially branching-lysine dendrites, onto which a number of antigen-binding fragment polypeptides are covalently attached. See for instance, Posnett et al. (1988) J. Biol. Chem. 263: 1719-1725; and Tam (1989) Met. Enz. 168:7-15. The result is a large macromolecule having a high molar ratio of antigen-binding fragment polypeptides to core. MAPs are efficient immunogens and useful antigens for immunoassays. The core for creating MAPs can be made by standard peptide synthesis techniques, or obtained commercially (Quality Controlled Biochemicals, Inc., Hopkinton, Mass.). A typical core matrix is made up of three levels of lysine and eight amino acid residues.

The invention further includes anti-idiotypic antigen-binding fragments to the DC-specific antigen-binding fragments of the invention. Such anti-idiotypes can be made by any method known in the art.

Cancer patients are often immunosuppressed and tolerant to some tumor-associated antigens (TAA). Triggering an active immune response to such TAA represents an important challenge in cancer therapy. Immunization with a given antigen generates an immune response including a CTL response, preferably a strong CTL response. The production of antibodies against the antigen can be helpful if the tumor cells are killed by ADCC (antibody-dependent cellular cytotoxicity). The invention encompasses the use of DCs identified and isolated by use of the antigen-binding fragments of the invention in inducing specific immune responses by methods known in the art. The immune responses can be specific to any antigen including, without limitation, those associated with cancer, infectious viruses, infectious bacteria, infectious parasites, infectious yeast, and autoimmune diseases (the induce tolerance). The ability to isolate subpopulations that are uniquely suited to inducing such a response results in preparations of DCs that are more effective than mixtures of subpopulations. Hybrid cells (e.g. DC/tumor cell) could also be used as cancer-specific therapy. Modified cells (including, without limitation, activated, in vitro matured, modulated with respect to their T helper cell polarizing capacity (Th1 v Th2 v Th3/Th-R), and modulated with respect to their T cell stimulating or anergizing or deleting capacity) are likewise encompassed by the invention and include, but are not limited to, genetically modified or transfected cells and cells that have been incubated with peptides or proteins suitable for antigen presentation or for internalization. Subpopulations include, without limitation, a particular differentiation stage within one lineage and a separate lineage of differention.

The invention further provides DCs, subpopulations thereof and mixtures thereof. The cells are selected using the antigen-binding fragments provided herein by any separation method known in the art. Compositions comprising the isolated cells are also encompassed by the invention. These include pharmaceutical and therapeutic compositions and any other composition containing the isolated cells. The DCs subpopulations isolated by the methods described herein are preferably substantially homogeneous. That is, cells isolated by a BDCA-specific antigen-binding fragments are preferably more than about 80% BDCA$^+$, more preferably more than about 90% BDCA$^+$ and most preferably more than about 95% BDCA$^+$. Of course, subsequent combinations of the cells with other DCs, or other hematopoietic cells can decrease the percentage of BDCA$^+$ cells, such combinations are also encompassed by the invention.

Likewise, the DCs obtained by the methods described herein are suitable for use in any method of treatment known in the art include references here. DCs altered to achieve these methods are also encompassed by the invention. These methods include, but are not limited to:

a) therapy with isolated DCs to induce specific T cell tolerance (killing or anergy instead of stimulation) in autoimmune diseases, allergies, graft versus host disease (GvHD), allograft rejection. For instance, DCs specific for such T cells can be modified to contain lysis, inactivating or death-inducing moieties so as to specifically target the T cells involved in the unwanted immune response for instance by antigen labeling or genetic modification such as by CD95L transfection. DC specificity for T cells is primarily caused by presentation of the appropriate T cell epitopes (peptides) via MHC I and II. The particular subsets of DCs with tolerance-inducing functions can be administered directly to the patient. Peripheral tolerance can be mediated by DCs modified to induce deletion (killing), anergy and suppression/regulation of T cells;

b) immunomodulation therapy with isolated DCs to induce particular cytokine expression profiles in specific T cells. This is particularly useful to influence production of Th1 (cytokines for specific inflammatory immune responses), Th2 (cytokines for specific humoral immune responses) or Th3 (cytokines for specific immunosuppression) cytokines. In the case of allergies and asthma for instance, induction of a Th1 response may reduce or eliminate the symptom-producing Th2 response;

c) therapy with DCs presenting antigens including, but not limited to, tumor antigens, viral antigens and cellular antigens;

d) therapy with DCs (with or without presenting antigens) and various cofactors including, but not limited to cytokines, costimulatory molecules and effector molecules in amounts and under conditions sufficient to modulate the immune response; and e) stimulating T cells in vitro to obtain antigen-specific T cells.

The antigen-binding fragments described herein are also suitable for a number of methods of treatment. These include, but are not limited to:

a) antibodies mimicking the ligand- or ligand-mediated immunotherapy for instance of DCs involved in autoimmunity or in vivo targeting of antigens or nucleic acids (viruses, plasmid DNA, RNA etc) to DCs for optimal and selective uptake/transfection. BDCA-2 may be particularly useful in this context as it appears to be a molecule with antigen uptake and processing function; and b) immunomonitoring: e.g. enumeration and characterization of BDCA-2$^+$, BDCA-3$^+$ and BDCA-4$^+$ DCs in various diseases and upon mobilization e.g. with a proliferation inducing ligand, e.g. flt3-Ligand or G-CSF.

Any carrier not harmful to the host can be used for the DCs. Suitable carriers are typically large, slowly metabolized macromolecules such as proteins; polysaccharides (such as latex functionalized Sepharose, agarose, cellulose, cellulose beads and the like); polymeric amino acid residues (such as polyglutamic acid, polylysine, and the like); amino acid copolymers; and inactive virus particles or attenuated bacteria, such as Salmonella.

2. Methods of Obtaining Additional DC-specific Antigen-binding Fragments

The invention encompasses methods of obtaining DC-specific antigen-binding fragments.

Methods of generating new DC-specific antigen-binding fragments, as detailed below, include, but are not limited to: 1) employing phage display techniques by which cDNA encoding antibody repertoires are preferably amplified from lymphocyte or spleen RNA using PCR and oligonucleotide primers specific for species-specific V regions; 2) immunizing mammals with the antigen and generating polyclonal or mAbs; and 3) employing phage display to make antibodies without prior immunization by displaying on phage, very large and diverse V gene repertoires. See, generally Hoogenboom et al. (1998) Immunotechnol. 4:1-20. Preferably, for therapeutic purposes, if non-human antigen binding fragments are to be used, these can be humanized by any method known in the art.

The method described by Medez et al. (1997) Nature Genetics 18:410 can be used. Briefly, purified antigen, is used to immunize transgenic mice lacking the native murine antibody repertoire and instead having most of the human antibody V-genes in the germ line configuration. Human antibodies are subsequently produced by the murine B cells. The antibody genes are recovered from the B cells by PCR library selection or classic hybridoma technology.

Alternatively, antibodies can be obtained from mice (such as BALB/c) after injection with purified DC-specific antigen. mAbs are generated using standard hybridoma technology. Maiti et al. (1997) Biotechnol. Int. 1:85-93 (human hybridomas); and Kohler and Milstein (1975) Nature 256;495-497 (mouse hybridomas). Murine antibodies can be subsequently humanized for instance by the methods described by Rosok et al. (1996) J. Biol. Chem. 271:22611-22618; Baca et al. (1997) J. Biol. Chem. 272:10678-10684; Rader et al. Proc. Natl. Acad. Sci. USA 95:8910-8915; and Winter and Milstein (1991) Nature 349:293-299.

A phage display approach can also be used to rapidly generate human antibodies against DCs. This approach can employ the method described-by Henderikx et al. (1998) Cancer Res. 58:4324-32. Antibody fragments displayed on phage are selected from a large naive phage antibody/fragment library containing different single chain antibodies by separating those that bind to immobilized antigen or DCs. Human antibody fragments are selected from naive repertoires constructed either from germline V-domains or synthesized with many mutations (mutations are targeted either by homologous gene re-assortments or error prone PCR) in both the framework and CDR regions. Antigen-binding fragments specifically reactive with DCs can be identified by screening against tumor and normal cells as described herein in order to identify DC-specific antigen-binding fragments.

The invention also encompasses methods of identifying antigen-binding fragments specific for a DCs by generating a suitable phage display library; isolating DC-specific antigens; screening the phage display library with the antigens according to standard immunochemical techniques to obtain phage that display an antigen-binding fragment that binds specifically to DCs; or screening the-phage display library obtained for DC specific antigen-binding fragments, by screening against DCs and other, related cells such as APCs and selecting the phage that bind preferentially to DCs. Methods of generating antigen-binding fragments by phage display are well known in the art. Hoogenboom et al. (1998).

Lymphocyte (PBL) or spleen RNA is typically used to make antibody fragment repertoires. Mutagenesis using homologous reassortment or error prone PCR increases the diversity. Any method known in the art can be used.

Repertoires of antibody genes can be amplified from immunized mice or humans using PCR and scFv or Fab antibody fragments obtained thereby can be cloned and expressed on the surface of bacteriophage. The antibody gene repertoires are amplified from lymphocyte or spleen RNA using PCR and oligonucleotide primers specific for host animal-specific V regions. Phage display can also be used to make antibodies without prior immunization by displaying very large and diverse V gene repertoires on phage. The natural V gene repertoires present in PBL are isolated by PCR amplification and the VH and VL regions are spliced together at random using PCR. Mutations can be targeted to the V-domain genes by homologous gene reassortments or error-prone PCR. Zhao et al. (1998) Nat. Biotechnol. 15:258; and Hoogenboom et al. (1998). Totally synthetic human libraries can also be created and used to screen for DC-specific antibody fragments. Regardless of the method used to operate the phage display library, each resulting phage has a functional antibody fragment displayed on its surface and contains the gene encoding the antibody fragment in the phage genome. See, e.g. WO97/02342.

Affinity chromatography in which binding antibodies can be subtracted from non-binding antibodies has been established for some time. Nissim et al. (1994) EMBO J. 13:692-698; and Vaughan et al. (1996) Nat. Biotechnol. 14:309-314. Critical parameters affecting success are the number and affinity of antibody fragments generated against a particular antigen. Until recently, the production of large, diverse libraries remained somewhat difficult. Historically, scFv repertoires have been assembled directly from VH and VL RT-PCR products. RNA availability and the efficiency of RT-PCR were limiting factors of the number of V genes available. Also, assembly required ligating three fragments, namely VH and VL and the linker regions. Marks et al. (1991) J. Mol. Biol. 222:581-597.

An improved library construction method uses cloned VH and VL gene repertoires in separate plasmid vectors to provide a stable and limitless supply of material for scFv assembly. Sheets et al. (1998) Proc. Natl. Acad. Sci. USA 95:6175-6162. Also, the efficiency is increased by having DNA encoding the linker region at the 5' end of the VL library. Therefore there are only two fragments to be ligated instead of three.

Anti-DC-antigen-binding fragments cari also be derived or manipulated. For example, the immunogenic activity of the V regions of the L and H chains can be screened by preparing a series of short polypeptides that together span the entire V region amino acid sequence. Using a series of polypeptides of 20 or 50 amino acid residues in length, each V region can be surveyed for useful functional properties. It is also possible to carry out a computer analysis of a protein sequence to identify potentially immunogenic polypeptides. Such peptides can then be synthesized and tested.

The invention further encompasses various adaptations of antigen-binding fragments described herein combined in various fashions to yield other anti-DC antigen-binding fragments with desirable properties. For instance, antigen-binding fragments with modified residues can be comprised in MAPs. In another example, an scFv is fused to a cytokine, such as IL-2. All such combinations are encompassed by this invention.

The antigen-binding fragments can be made by any suitable procedure, including proteolysis, recombinant methods or chemical syntheses. These methods are known in the art and need not be described in detail. Examples of proteolytic enzymes include, but are not limited to, trypsin, chymotrypsin, pepsin, papain, V8 protease, subtilisin, plasmin, and thrombin. Intact antigen-binding fragments can be incubated with one or more proteases simultaneously or sequentially. Alternatively, or in addition, intact antibody can be treated with disulfide reducing agents. Peptides can then be separated from each other by techniques known in the art, including but not limited to, gel filtration chromatography, gel electrophoresis, and reverse-phase HPLC.

Anti-DC antigen-binding fragments can also be made by expression from a polynucleotide encoding the peptide, in a suitable expression system by any method known in the art. Typically, polynucleotides encoding a suitable polypeptide are ligated into an expression vector under control of a suitable promoter and used to genetically alter the intended host cell. Both eukaryotic and prokaryotic host systems can be used. The polypeptide is then isolated from lysed cells or from the culture medium and purified to the extent needed for its intended use. Examples of prokaryotic host cells appropriate for use with this invention include *E. coli, Bacillus subtilis* and any other suitable host cell. Examples of eukaryotic host cells include, but are not limited to yeast, avian, insect, plant, and animal cells such as COS7, HeLa, and CHO cells.

Optionally, matrix-coated channels or beads and cell co-cultures can be included to enhance growth of antigen-binding fragment producing cells. For the production of large amounts of mAbs, it is generally more convenient to obtain ascitic fluid. The method of raising ascites generally comprises injecting hybridoma cells into an immunologically naive, histocompatible or immunotolerant mammal, especially a mouse. The mammal can be primed for ascites production by prior administration of a suitable composition; e.g., Pristane. The ascitic fluid is removed from the animal and processed to isolate antibodies.

Alternatively, antigen-binding fragments can be chemically synthesized using amino acid sequence data and other information provided in this disclosure, in conjunction with standard methods of protein synthesis. A suitable method is the solid phase Merrifield technique. Automated peptide synthesizers are commercially available, such as those manufactured by Applied Biosystems, Inc. (Foster City, Calif.).

Another method of obtaining anti-DC antigen-binding fragments is to immunize suitable host animals with BDCA-2, BDCA-3 and/or BDCA-4 and follow standard methods for polyclonal or mAb production and isolation. mAbs thus produced can be "humanized" by methods known in the art. The invention thus encompasses humanized mAbs.

In "humanized" antibodies at least part of the sequence has been altered from its initial form to render it more like human Igs. In one version, the H chain and L chain C regions are replaced with human sequence. This is a fusion polypeptide comprising an anti-DC V region and a heterologous Ig (C) region. In another version, the CDR regions comprise anti-DC amino acid sequences, while the V framework regions have also been converted human sequences. See, for example, EP 0329400. In a third version, V regions are humanized by designing consensus sequences of human and mouse V regions, and converting residues outside the CDRs that are different between the consensus sequences.

In making humanized antibodies, the choice of framework residues can aid in retaining high binding affinity. In principle, a framework sequence from any human antibody can serve as the template for CDR grafting; however, it has been demonstrated that straight CDR replacement into such a framework can lead to significant loss of antigen binding affinity. Glaser et al. (1992) J. Immunol. 149:2606; Tempest et al. (1992) Biotechnol. 9:266; and Shalaby et al. (1992) J. Exp. Med. 17:217. The more homologous a human antibody is to the original murine antibody, the less likely that the human framework will introduce distortions into the murine CDRs that could reduce affinity. Based on a sequence homology search against an antibody sequence database, the human antibody IC4 provides good framework homology to muM4TS.22, although other highly homologous human antibodies are suitable as well, especially κ L chains from human subgroup I or H chains from human subgroup III. Kabat et al. (1987). Various computer programs such as ENCAD predict the ideal sequence for the V region. Levitt et al. (1983) J. Mol. Biol. 168:595. The invention thus encompasses human antibodies with different V regions. It is within the skill of one in the art to determine suitable V region sequences and to optimize these sequences. Methods for obtaining antibodies with reduced immunogenicity are also described in U.S. Pat. No. 5,270,202 and EP 699,755.

In certain applications, such as when an antigen-binding fragment or DCA is expressed in a suitable storage medium such as a plant seed, the antigen-binding fragment can be stored without purification. Fiedler et al. (1995) Biotechnol. 13:1090-1093. For most applications, it is generally preferable that the polypeptide is at least partially purified from other cellular constituents. Preferably, the peptide is at least about 50% pure as a weight percent of total protein. More preferably, the peptide is at least about 50-75% pure. For clinical use, the peptide is preferably at least about 80% pure.

If the peptides are to be administered to an individual, preferably it is at least 80% pure, more preferably at least 90% pure, even more preferably at least 95% pure and free of pyrogens and other contaminants. In this context, the percent purity is calculated as a weight percent of the total protein content of the preparation, and does not include constituents which are deliberately added to the composition purification.

The invention also encompasses methods of detecting, enumerating and/or identifying DCs and subsets thereof, in a biological sample and measuring antigens such as soluble BDCA-2, BDCA-3 or BDCA-4 and/or DCs in body fluids. The methods include obtaining a biological sample, contacting the sample with an antigen-binding fragment described herein under conditions that allow antibody-antigen-binding and detecting binding, if any, of the antibody to the sample as compared to a control, biological sample.

After a biological sample is suitably prepared, for instance by enriching for DC concentration or antigen concentration, it is mixed with excess antigen-binding fragments under conditions that permit formation of a complex between DCs or antigen and the antibody. The amount of complex formed or the number of complex bearing DCs then determined, and eventually compared with complexes formed with standard samples containing known amounts of target antigen in the range expected or known DC concentrations. Complex formation can be observed by immunoprecipitation or nephelometry, but it is generally more sensitive to employ a reagent labeled with such labels as radioisotopes like $^{125}$I, enzymes like peroxidase and β-galactosidase, or fluorochromes like fluorescein. Methods of detecting cells and antigens are well known in the art. For cell detection, flow cytometry is particularly useful, with antigen, ELISA is preferred.

The specific recognition of an anti-DC antigen-binding fragment to an antigen can be tested by any immunoassay known in the art. Any form of direct binding assay is suitable. In one such assay, one of the binding partners, the antigen or the putative antigen-binding fragment, is labeled. Suitable labels include, but are not limited to, radioisotopes such as $^{125}$I, enzymes such as peroxidase, fluorescent labels such as fluorescein, and chemiluminescent labels. Typically, the other binding partner is insolubilized (for example, by coating onto a solid phase such as a microtiter plate) to facilitate removal of unbound soluble binding partner. After combining the labeled binding partner with the unlabeled binding partner, the solid phase is washed and the amount of bound label is determined.

When used for immunotherapy, the antigen-binding fragments described herein can be unlabeled or labeled with a therapeutic agent as described herein and as known in the art. These agents can be coupled either directly or indirectly to the antigen-binding fragments of the invention. One example of indirect coupling is by use of a spacer moiety. These spacer moieties, in turn, can be either insoluble or soluble (Diener et al. (1986) Science 231:148) and can be selected to enable drug release at the target site. Examples of therapeutic agents that can be coupled to antigen-binding fragments for immunotherapy include, but are not limited to, antigens, including tumor antigens, viral antigens, bacterial antigens, parasite-derived antigens and autoantigens, bioresponse modifiers, drugs, radioisotopes, lectins, and toxins. Bioresponse modifiers include cytokines and chemokines which include, but are not limited to, IL-2, IL-3, IL-4, G-CSF, GM-CSF, IL-10, IL-12, TGF-β, MTP-AB, SDF-1, Lymphotactin, DC-CK1, Eotoxins, IP-10, TARC; Rantes, MIP-1α, MIP-1β, SLC, ITAC, MIE, MDC, MCP-1, TCA-3, MCP-2, -3, -4 and interferons. Interferons with which antigen-binding fragments can be labeled include IFN-α, IFN-β, and IFN-γ and their subtypes.

In using radioisotopically conjugated antigen-binding fragments for immunotherapy, certain isotypes can be more preferable than others depending on such factors as isotype stability and emission. If desired, cell population recognition by the antigen-binding fragment can be evaluated by the in vivo diagnostic techniques described below. In general, α and β particle-emitting radioisotopes are preferred in immunotherapy. For example, a high energy β emitter capable of penetrating several millimeters of tissue, such as $^{90}$Y, can be preferable. On the other hand, a short range, high energy α emitter, such as $^{212}$Bi, can be preferable. Examples of radioisotopes which can be bound to the antigen-binding fragments of the invention for therapeutic purposes include, but are not limited to, $^{125}$I, $^{131}$I, $^{90}$Y, $^{67}$Cu, $^{212}$Bi, $^{211}$At, $^{212}$Pb, $^{47}$Sc, $^{109}$Pd, and $^{188}$Re.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is preferably accomplished by binding the α peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by *Corynebacterium diphtheria* which can be used therapeutically. This toxin consists of an α and β subunit which under proper conditions can be separated. The toxic A chain component can be bound to an antigen-binding fragment described herein and used for site specific delivery to a specific subset of DCs.

Recombinant methods are well known in the art. The practice of the invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (Gait, ed., 1984); "Animal Cell Culture" (Freshney, ed., 1987); "Methods in Enzymology" (Academic Press, Inc.); "Handbook of Experimental Immunology" (Wei & Blackwell, eds.); "Gene Transfer Vectors for Mammalian Cells" (Miller & Calos, eds., 1987); "Current Protocols in Molecular Biology" (Ausubel et al., eds., 1987); "PCR: The Polymerase Chain Reaction", (Mullis et al., eds., 1994); and "Current Protocols in Immunology" (Coligan et al., eds., 1991). These techniques are applicable to the production of the polynucleotides and polypeptides, and, as such, can be considered in making and practicing the invention. Particularly useful techniques are discussed in the sections that follow.

The invention provides various polynucleotides encoding BDCA antigens. The invention also encompasses polynucleotides encoding for functionally equivalent variants and derivatives of these antigens and functionally equivalent fragments thereof that can enhance, decrease or not significantly affect properties of the polypeptides encoded thereby. These functionally equivalent variants, derivatives, and fragments may display the ability to specifically bind to their respective antibodies. For instance, changes that will not significantly affect properties of the encoded poly eptide include, but are not limited to changes in a DNA sequence that do not change the encoded amino acid sequence, as well as those that result in conservative substitutions of amino acid residues, one or a few amino acid residue deletions or additions, and substitution of amino acid residues by amino acid analogs. Conservative substitutions are those which conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

The polynucleotides of the invention can comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as can be desirable to provide embodiments of this invention.

The invention encompasses a polynucleotide of at least about 15 consecutive nucleotides, preferably at least about 20 nucleotides, more preferably at least about 25 consecutive nucleotides, more preferably at least about 35 consecutive nucleotides, more preferably at least about 50 consecutive nucleotides, even more preferably at least about 75 nucleotides, still more preferably at least about 100 nucleotides, still more preferably at least about 200 nucleotides, and even more preferably at least about 300 nucleotides that forms a stable hybrid with a polynucleotide encoding BDCA-2 and BDCA-3, preferably the cDNA sequence found in FIG. 12. Any set of conditions can be used for this test, provided at least one set exists where the test polynucleotide demonstrates the required specificity.

Hybridization reactions can be performed under conditions of different "stringency". Conditions that increase stringency of a hybridization reaction are published. See, for example, Sambrook and Maniatis. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

The invention also provides polynucleotides encoding the BDCA polypeptides. Preferably, the polypeptides are or are derived from those in. FIG. 12.

The invention also provides polynucleotides covalently linked with a detectable label. Such polynucleotides are useful, for example, as probes for detection of related nucleotide sequences.

The polynucleotides of this invention can be obtained using chemical synthesis, recombinant cloning methods, PCR, or any combination thereof. Methods of chemical polynucleotide synthesis are well known in the art and need not be described in detail herein. One of skill in the art can use the sequence data provided herein to obtain a desired polynucleotide by employing a DNA synthesizer or ordering from a commercial service.

Alternatively, nucleotides encoding BDCAs and the peptides encoded thereby can be obtained from a producing cell line, cloning vector, or expression vector. RNA or DNA encoding the desired sequence can be isolated, amplified, and processed by standard recombinant techniques. Such techniques include digestion with restriction nucleases, and amplification by polymerase chain reaction (PCR), or a suitable combination thereof. PCR technology is described in U.S. Pat. Nos. 4,683,195; 4,800,159; 4,754,065; and 4,683,202, as well as PCR: The Polymerase Chain Reaction, Mullis et al. eds., Birkauswer Press, Boston (1994). Isolation and purification of the peptides encoded thereby can be by any method known in the art.

Polynucleotides comprising a desired sequence can be inserted into a suitable vector, the vector in turn can be introduced into a suitable host cell for replication and amplification. Polynucleotides can be inserted into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. Amplified DNA can be isolated from the host cell by standard methods. See, e.g., Sambrook et al. (1989). RNA can also be obtained from transformed host cell, it can be obtained by using a DNA-dependent RNA polymerase.

The present invention further includes a variety of vectors comprising a polynucleotide encoding BDCA-2 and/or BDCA-3. These vectors can be used for expression of recombinant polypeptides as well as a source of BDCA-encoding polynucleotides. Cloning vectors can be used to obtain replicate copies of the polynucleotides, or for storing the polynucleotides in a depository for future recovery. Expression vectors (and host cells containing these expression vectors) can be used to obtain polypeptides produced from the polynucleotides they contain. They can also be used where it is desirable to express BDCA-2 and/or BDCA-3 in an individual and thus have intact cells capable of synthesizing the polypeptide, such as in gene therapy. Suitable cloning and expression vectors include any known in the art e.g., those for use in bacterial, mammalian, yeast and insect expression systems. Specific vectors and suitable host cells are known in the art and are not described in detail herein See e.g. Gacesa and Ramji, Vectors, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. Typical selection genes either: (a), confer resistance to antibiotics or other toxic substances, e.g., ampicillin, neomycin, methotrexate; (b) complement auxotrophic deficiencies; or (c) supply critical nutrients not available from complex media. The choice of the proper marker gene will depend on the host cell, and appropriate genes for different hosts are known in the art. Vectors also typically contain a replication system recognized by the host.

Suitable cloning vectors can be constructed according to standard techniques, or can be selected from a large number of cloning vectors available in the art. While the cloning vector selected can vary according to the host cell intended to be used, useful cloning vectors will generally have the ability to self-replicate, can possess a single target for a particular restriction endonuclease, or can carry genes for a marker that can be used in selecting clones containing the vector. Suitable examples include plasmids and bacterial viruses, e.g., pUC18, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide encoding a BDCA of interest. The polynucleotide encoding BDCA is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) can be derived from a gene encoding a BDCA, or they can be heterologous (i.e., derived from other genes or other organisms). A polynucleotide sequence encoding a signal peptide can also be included to allow a BDCA to cross or lodge in cell membranes or be secreted from the cell. A number of expression vectors suitable for expression in eukaryotic cells including yeast, avian, and mammalian cells are known in the art. One example of an expression vector is pcDNA3 (Invitrogen, San Diego, Calif.), in which transcription is driven by the cytomegalovirus (CMV) early promoter/enhancer. This vector also contains recognition sites for multiple restriction enzymes for insertion of the polynucleotide of interest. Another example of an expression vector (system) is the baculovirus/insect system. Other suitable for use in antibody-targeted gene therapy comprising a polynucleotide encoding a BDCA. Suitable systems are described for instance by Brown et al. (1994) Virol. 198:477-488; and Miyamura et al. (1994) Proc. Natl. Acad. Sci. USA 91:8507-8511.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection. The choice of means of introducing vectors or polynucleotides encoding BDCAs will often depend on features of the on the host cell.

Once introduced into a suitable host cell, expression of a BDCA can be determined using any assay known in the art. For example, the presence thereof can be detected by RIA or ELISA of the culture supernatant (if the polypeptide is secreted) or cell lysates.

A vector of this invention can contain one or more polynucleotides encoding a BDCA. It can also contain polynucleotide sequences encoding other polypeptides that enhance, facilitate, or modulate the desired result, such as cytokines, including, but not limited to, IL-2, IL-4, GM-CSF, TNF-α and IFN-γ. Also embodied in this invention are vaccinia vectors encoding for recombinant BDCAs.

Other embodiments of this invention are host cells transformed with polynucleotides encoding BDCAs and vectors comprising the polynucleotide sequences, as described above. Both prokaryotic and eukaryotic host cells can be used. Prokaryotic hosts include, but are not limited to, bacterial cells, for example *E. coli* and *mycobacteria*. Eukaryotic hosts include, but are not limited to, yeast, insect, avian, plant and mammalian cells. Host systems are known in the art and need not be described in detail herein. Examples of a mammalian host cells include, but are not limited to, CHO and NSO, obtainable from the European Collection of Cell Cultures (England). Transfection of NSO cells with a plasmid, for example, which is driven by a CMV promoter, followed by amplification of this plasmid in using glutamine synthetase provides a useful system for protein production. Cockett et al. (1990) Bio/Technology 8:662-667.

The host cells of this invention can be used, inter alia, as repositories of polynucleotides encoding BDCAs, or as vehicles for production thereof. They can be used also as vehicles for in vivo expression of BDCAs.

The polynucleotides of this invention have several uses. They are useful, for example, in expression systems for the production of BDCA. They are also useful as hybridization probes to assay for the presence of polynucleotides encoding BDCAs or related sequences in a sample using methods well known to those in the art. Further, the polynucleotides are also useful as primers to effect amplification of desired polynucleotides. The polynucleotides of this invention are also useful in pharmaceutical compositions including vaccines and for gene therapy.

The polynucleotides can also be used as hybridization probes for detection of BDCA-encoding sequences. Suitable hybridization samples include cells transformed ex vivo for use in gene therapy. In one illustration, DNA or RNA is extracted from a sample, and optionally run on a gel and/or digested with restriction nucleases. The processed sample polynucleotide is typically transferred to a medium suitable for washing. The sample polynucleotide is then contacted with the BDCA-encoding polynucleotide probe under conditions that permit a stable duplex to form if the sample contains a complementary polynucleotide sequence. Any stable duplexes formed are detected by any suitable means. For example, the polynucleotide probe can be supplied in labeled form, and label remaining with the sample after washing will directly reflect the amount of stable duplex formed. In a second illustration, hybridization is performed in situ. A suitably prepared tissue sample is overlaid with a labeled probe to indicate the location of BDCA-encoding sequences.

A short polynucleotide can also be used as a primer for a PCR reaction, particularly to amplify a longer sequence comprising a region hybridizing with the primer. This can be conducted preparatively, in order to produce polynucleotide for further genetic manipulation. It can also be conducted analytically, to determine whether a BDCA-encoding polynucleotide is present, for example, in a sample of diagnostic interest.

Another use of the polynucleotides is in vaccines and gene therapy. The general principle is to administer the polynucleotide so that it either promotes or attenuates the expression of the polypeptide encoded thereby. Thus, the present invention includes methods of inducing an immune response and methods of treatment comprising administration of an effective amount of polynucleotides encoding BDCAs to an individual. In these methods, a polynucleotide encoding BDCA is administered to an individual, either directly or via cells transfected with the polynucleotide. Preferably, the polynucleotide is in the form of a circular plasmid, preferably in a supercoiled configuration. Preferably, the polynucleotide is replicated inside a cell. Thus, the polynucleotide is operatively linked to a suitable promoter, such as a heterologous promoter that is intrinsically active in cells of the target tissue type. Preferably, once in cell nuclei, plasmids persist as circular non-replicating episomal molecules. In vitro mutation can be carried out with plasmid constructs to encode, for example, molecules with greater affinity and/or avidity.

To determine whether plasmids containing BDCA polynucleotides are capable of expression in eukaryotic cells, cells such as COS-7, CHO, or HeLa can be transfected with the plasmids. Expression is then determined by immunoassay; for example, by Western blot. Smaller BDCAs can be detected, for example, by constructing the plasmid so that the resultant polypeptide is fused with a tag, such as a target epitope or enzyme label. Further characterization of the expressed polypeptide can be achieved by purifying the peptide and then conducting one of the functional assays described herein.

In one mode of gene therapy, the polynucleotides of this invention are used for genetically altering cells ex vivo. In this strategy, cells removed from a donor or obtained from a cell line are transfected or transduced with BDCA vectors, and then administered to a recipient. Suitable cells for transfection include peripheral blood mononuclear cells.

In another mode of gene therapy, the polynucleotides of this invention are used for genetically altering cells in vivo. The purpose can include, but is not limited to, treating various types of cancer.

The polynucleotides can also be used to produce cells that do not express BDCA-2, and transgenic animals expressing BDCA-2.

Also obtained from the invention are cells engineered not to express or to express at significantly reduced levels BDCA-2. Such cells may be produced by selecting a cell, preferably a DC, and providing to the cell an expression construct comprising a polynucleotide encoding a BDCA-2 gene wherein the polynucleotide is positioned antisense to and operatively linked to a promoter. The expression of such a polynucleotide effectively produces a cell deficient in BDCA-2.

In other embodiments the present invention provides a method for the preparation of recombinant host cells that produce significantly reduced amounts or even "knockout" the production of BDCA-2. These recombinant host cells can be prepared by using one or more means that are well known to those of skill in the art. For example, gene expression can be inhibited by the incorporation of constructs for antisense DNA or RNA into the genome. Deletions or mutations of the endogenous BDCA-2 genes can render them nonfunctional. Nucleic acids encoding ribozymes—RNA-cleaving enzymes—that specifically cleave BDCA-2 mRNA can be introduced into the recombinant host cells.

The term "knockout" refers to partial or complete suppression of the expression of at least a portion of a protein encoded by an endogenous DNA sequence, e.g. BDCA-2, in a cell. The term "knockout construct" refers to a nucleic acid sequence that is designed to decrease or suppress expression of a protein encoded by endogenous DNA sequences in a cell.

These recombinant constructs can be incorporated into knockout mammals such that the production of BDCA-2 is suppressed in DCs. The preparation of knock out and transgenic animals is well known to those of skill in the art and is described in U.S. Pat. Nos. 5,434,340, 5,530,179 and 5,557,032.

The invention further provides methods for producing animals and the animals-so produced that over-express BDCA-2. These methods generally comprise introducing animal cells into an animal, the animal cells having been treated in vitro to insert therein a DNA segment encoding a BDCA-2 polypeptide, the animal cells expressing in vivo in the animal BDCA-2.

D. Kits

The invention encompasses kits containing anti-DC-specific antigen-binding fragments, for measuring BDCA-2 including soluble BDCA-2, including isoforms thereof, in serum and other sources. Diagnostic procedures using the kits can be performed by diagnostic laboratories, experimental laboratories, practitioners, or private individuals. The clinical sample is optionally pre-treated for enrichment of the target being tested for. The user then applies a reagent contained in the kit in order to detect the changed level or alteration in the diagnostic component.

Optionally, the reagent can be conjugated with a label to permit detection of any complex formed with the target in the sample. In another option, a second reagent is provided that is capable of combining with the first reagent after it has found its target and thereby supplying the detectable label. For example, labeled anti-murine IgG can be provided as a secondary reagent. Labeled avidin is a secondary reagent when the primary reagent has been conjugated to biotin.

The kits can be employed on a variety of biological samples including, both liquid samples, cell suspensions and tissue samples. Suitable assays that can be supplied in kit form include those described herein.

Each reagent is supplied in a solid form or dissolved/suspended in a liquid buffer suitable for inventory storage and later for exchange or addition into the reaction medium when the test is performed. Suitable packaging is provided. The kit can optionally provide additional components that are useful in the procedure. These optional components include, but are not limited to, buffers, capture reagents, developing reagents, labels, reacting surfaces, means for detection, control samples, instructions, and interpretive information.

E. Therapeutic Compositions

1. Compositions of Matter

The preparation of pharmaceutical compositions described herein is conducted in accordance with generally accepted procedures for the preparation of pharmaceutical preparations. See, for example, Remington's Pharmaceutical Sciences 18th Edition (1990), E. W. Martin ed., Mack Publishing Co., PA. Depending on the intended use and mode of administration, it can be desirable to process the active. ingredient further in the preparation of pharmaceutical compositions. Appropriate processing can include sterilizing, mixing with appropriate non-toxic and non-interfering components, dividing into dose units, and enclosing in a delivery device. In one embodiment, the therapeutic compositions contain DCs, subpopulations thereof or mixtures thereof. In another embodiment, the compositions contain the antigen-binding fragments described herein. Preferably, the antigen-binding fragments are, or are derived from, the mAbs listed in Table 1. Preferably the DC compositions contain DCs isolated with one of these antigen-binding fragments.

(a) General Modes of Administration

Pharmaceutical compositions of the invention are administered by a mode appropriate for the form of composition. Typical routes include intravenous, subcutaneous, intramuscular, intraperitoneal, intradermal, oral, intranasal, intradermal, and intrapulmonary (i.e., by aerosol). Pharmaceutical compositions for human use are typically administered by a parenteral route, most typically intravenous, subcutaneous, intramuscular. Although not required, pharmaceutical compositions are preferably supplied in unit dosage form suitable for administration of a precise amount. Also contemplated by this invention are slow release or sustained release forms, whereby a relatively consistent level of the active compound are provided over an extended period:

(b) Liquid Formulations

Liquid pharmaceutically acceptable compositions can, for example, be prepared by dissolving or dispersing a polypeptide or polynucleotide embodied herein in a liquid excipient, such as water, saline, aqueous dextrose, glycerol, or ethanol. The composition can optionally also contain other medicinal agents, pharmaceutical agents, carriers, and auxiliary substances such as wetting or emulsifying agents, and pH buffering agents. Compositions for injection can be supplied as liquid solutions or suspensions, as emulsions, or as solid forms suitable for dissolution or suspension in liquid prior to injection.

Pharmaceutical compositions for oral, intranasal, or topical administration can be supplied in solid, semi-solid or liquid forms, including tablets, capsules, powders, liquids, and suspensions. For administration via the respiratory tract, a preferred composition is one that provides a solid, powder, or liquid aerosol when used with an appropriate aerosolizer device.

The invention also encompasses:compositions comprising liposomes with membrane bound peptide to specifically deliver the liposome to the area of the tumor or neoplastic cells or to the immune system. These liposomes can be produced such that they contain, in addition to peptide, immunotherapeutic agents such as those described above which would then be released at the recognition site. Wolff et al. (1984) Biochem. Biophys. Acta 802:259. Another such delivery system utilizes chimeric parvovirus B19 capsids for presentation of the antigen-binding fragments. Brown et al. (1994) Virol. 198:477-488; and Miyamura et al. (1994) Proc. Natl. Acad. Sci. USA 91:8507-8511. Such chimeric systems are encompassed for use herein.

Compositions embodied in this invention can be assessed for their efficacy in a number of ways. Accordingly, test compounds are prepared as a suitable pharmaceutical composition and administered to test subjects. Initial studies are preferably done in small animals such as mice or rabbits, optionally next in non-human primates and then ultimately in humans. Immunogenicity is preferably tested in individuals without a previous antibody response. A test composition in an appropriate test dose is administered on an appropriate treatment schedule. It can be appropriate to compare different doses and schedules within the predicted range. The dosage ranges for the administration of antigen-binding fragments are large enough to produce the desired effect in which the symptoms of the disease are ameliorated without causing undue side effects such as unwanted cross-reactions and anaphylactic reactions. Generally, the dosage will vary with the age, condition, sex and extent of the disease in the patient and can be determined by one of skill in the art. The dosage can be adjusted by the individual physician in the event of any complication. Generally, when the compositions are administered conjugated with therapeutic agents, lower dosages, comparable to those used for in vivo immunodiagnostic imaging, can be used.

2. Antigen-binding Fragments

The invention encompasses pharmaceutical compositions containing the antigen-binding fragments described herein. Such pharmaceutical compositions are useful for inducing or aiding an immune response and treating neoplastic diseases, or including tolerance and treating autoimmune diseases, (GvHD, allograft rejection, allergen, etc.) either alone or in conjunction with other forms of therapy, such as chemotherapy, radiotherapy or immune therapies described in WO98/23735; WO98/34642; WO97/10000; WO97/10001; and WO97/06821. Other methods of treatment are described herein and/or known in the art. Suitable diseases include, without limitation, viral, parasitic, bacterial, fungal, neoplastic and autoimmune.

In a murine breast cancer model, Flt3-Ligand (Flt3-L), a stimulatory cytokine for a variety of hematopoietic lineages, including DCs and B cells, has been used in conjunction with murine breast cancer cells as a vaccine. Chen et al. (1997) Cancer Res. 57:3511-6. DCs can also be loaded with or transduced to express tumor antigens; these cells are then used as adjuvants to tumor vaccination. DCs present tumor-associated antigens endogenously to the afferent lymphatic system in the appropriate MHC-restricted context. Wan et al. (1997) Hum. Gene Ther. 8:1355-63; Peiper et al. (1997) Surgery 122:235-41; and Smith et al. (1997) Int. Immunol. 9:1085-93. Current melanoma vaccines manipulate antigen presentation networks and combine the best cellular and antibody antitumor immune response effective in mediating tumor protective immunity. These therapies have caused regression, delayed disease progression or an improvement in survival in some cases, with a paucity of side effects. Kuhn et al. (1997) Dermatol. Surg. 23:649-54. Melanoma vaccines are also reviewed in Conforti et al. (1997) J. Surg. Oncol. 66:55-64.

Vaccines can be packaged in pharmaceutically acceptable carriers, admixed with adjuvants or other components (such as cytokines) as known in the art. Vaccines for veterinarian use are substantially similar to that in humans with the exception that adjuvants containing bacteria and bacterial components such as Freund's complete or incomplete adjuvants, are allowed in the formulations.

F. Methods of Treatment

Also included in this invention are methods for treating a variety of disorders as described herein and/or known in the art. The methods comprise administering an amount of a pharmaceutical composition containing a composition of the invention in an amount effective to achieve the desired effect, be it palliation of an existing condition or prevention of recurrence. For treatment of cancer, the amount of a pharmaceutical composition administered is an amount effective in producing the desired effect. An effective amount can be provided in one or a series of administrations. An effective amount can be provided in a bolus or by continuous perfusion. Suitable active agents include the anti-neoplastic drugs, bioresponse modifiers and effector cells such as those described by Douillard et al. (1986) Hybridomas (Supp. 1:5139).

Pharmaceutical compositions and treatment modalities are suitable for treating a patient by either directly or indirectly eliciting an immune response against neoplasia. An "individual," "patient" or "subject" is a vertebrate, preferably a mammal, more preferably a human. Mammals include, but are not limited to: humans, wild animals, feral animals, farm animals, sport animals, and pets. A "cancer subject" is a mammal, preferably a human, diagnosed as having a malignancy or neoplasia or at risk thereof.

As used herein, "treatment" refers to clinical intervention in an attempt to alter the disease course of the individual or cell being treated, and can be performed either for prophylaxis or during the course of clinical pathology. Therapeutic effects of treatment include without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis.

The "pathology" associated with a disease condition is any condition that compromises the well-being, normal physiology, or quality of life of the affected individual. This can involve, but is not limited to, destructive invasion of affected tissues into previously unaffected areas, growth at the expense of normal tissue function, irregular or suppressed biological activity, aggravation or suppression of an inflammatory-or immunologic response, increased susceptibility to other pathogenic organisms or agents, and undesirable clinical symptoms such as pain, fever, nausea, fatigue, mood alterations, and such other disease-related features as can be determined by an attending physician.

An "effective amount" is an amount sufficient to effect a beneficial or desired clinical result upon treatment. An effective amount can be administered to a patient in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition and the form and effective concentration of the antigen-binding fragment administered.

The term "immunomodulatory" or "modulating an immune response" as used herein includes immunostimulatory as well as immunosuppressive effects. Immunostimulatory effects include, but are not limited to, those that directly or indirectly enhance cellular or humoral immune responses. Examples of immunostimulatory effects include, but are not limited to, increased antigen-specific antibody production; activation or proliferation of a lymphocyte population such as NK cells, $CD4^+$ cells, $CD8^+$ cells, macrophages and the like; increased synthesis of cytokines or chemokines including, but not limited to, IL-1, IL-2, IL-4, IL-5, IL-6, IL-12, interferons, TNF-$\alpha$, IL-10, TGF-$\beta$ and the like. Immunosuppressive effects include those that directly or indirectly decrease cellular or humoral immune responses. Examples of immunosuppressive effects include, but are not limited to, a reduction in antigen-specific antibody production such as reduced IgE production; activation of lymphocyte or other cell populations that have immunosuppressive activities such as those that result in immune tolerance; and increased synthesis of cytokines that have suppressive effects toward certain cellular functions including, but not limited to IL-10 and TGF-$\beta$. One example of this is IFN-$\gamma$, which appears to block IL-4 induced class switch to IgE and IgG1, thereby reducing the levels of these antibody subclasses.

Suitable human subjects for cancer therapy further comprise two treatment groups, which can be distinguished by clinical criteria. Patients with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in this invention is administered to these patients to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group." These are individuals who have had a history of cancer, but have been responsive to another mode of therapy. The prior therapy can have included (but is not restricted to, surgical resection, radiotherapy, and traditional chemotherapy. As a result, these individuals have no clinically measurable tumor. However, they are suspected of being at risk for progression of the disease, either near the original tumor site, or by metastases.

"Adjuvant" as used herein has several meanings, all of which will be clear depending on the context in which the term is used. In the context of a pharmaceutical preparation, an adjuvant is a chemical or biological agent given in combination (whether simultaneously or otherwise) with, or recombinantly fused to, an antigen to enhance immunogenicity of the antigen. For review see, Singh et al. (1999) Nature Biotech. 17:1075-1081. Isolated DCs have also been suggested for use as adjuvants. Compositions for use therein are included in this invention. In the context of cancer diagnosis or treatment, adjuvant refers to a class of cancer patients with no clinically detectable tumor mass, but who are suspected of risk of recurrence.

This group can be further subdivided into high-risk and low-risk individuals. The subdivision is made on the basis of features observed before or after the initial treatment. These features are known in the clinical arts, and are suitably defined for each different cancer. Features typical of high-risk subgroups are those in which the tumor has invaded neighboring tissues, or who show involvement of lymph nodes.

Another suitable group is those with a genetic predisposition to cancer but who have not yet evidenced clinical signs of cancer. For instance, women testing positive for a genetic mutation associated with breast cancer, but still of childbearing age, can wish to receive one or more of the antigen-binding fragments described herein in treatment prophylactically to prevent the occurrence of cancer until it is suitable to perform preventive surgery.

Human cancer patients, including, but not limited to, glioblastoma, melanoma, neuroblastoma; adenocarcinoma, glioma, soft tissue sarcoma, and various carcinomas (including small cell lung cancer) are especially appropriate subjects. Suitable carcinomas further include any known in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolarcarcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bileduct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy chain disease, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas.

The patients can have an advanced form of disease, in which case the treatment objective can include mitigation or reversal of disease progression, and/or amelioration of side effects. The patients can have a history of the condition, for which they have been treated, in which case the therapeutic objective will typically include a decrease or delay in the risk of recurrence.

Autoimmune disorders are the caused by a misdirected immune response resulting in self-destruction of a variety of cells, tissues and organs. The cause of these disorders is unknown. Recognition of self through the MHC is known to be of importance in an immune response. However, prevention of an autoimmune response and the cells responsible for autoimmunity are not well understood.

Autoimmunity results from a combination of factors, including genetic, hormonal, and environmental influences. Many autoimmune disorders are characterized by B cell hyperactivity, marked by proliferation of B cells and autoantibodies and by hypergammaglobulinemia. B cell hyperactivity is probably related to T cell abnormalities. Hormonal and genetic factors strongly influence the incidence of autoimmune disorders; for example, lupus erythematosus predominantly affects women of child-bearing age, and certain HLA haplotypes are associated with an increased risk of specific autoimmune disorders.

Common autoimmune disorders include, but are not limited to, rheumatoid arthritis, juvenile rheumatoid arthritis, psoriatic arthritis, ankylosing spondylitis, Sjögren's syndrome, lupus erythematosus, Goodpasture's syndrome, Reiter's syndrome, scleroderma, vasculitis, polymyositis and dermatomyositis. Many of these conditions include aberrant inflammatory reactions related to the immunologic disorders. The DCs described herein are suitable for use in treatment of these disorders particularly when used to inactivate or induce tolerogenization in T cells involved in the disorder. Methods of treatment are known in the art. As discussed herein, one or more of the subsets of DCs obtained by the methods described herein are suitable for use in treatment of autoimmunity.

"Immunologic activity" of an antigen-binding fragment refers to specifically binding the antigen which the intact antibody-recognizes. Such binding can or can not elicit an immune response. A specific immune response can elicit antibody, B cell responses, T cell responses, any combination thereof, and effector functions resulting therefrom. Included, without limitation, are the antibody-mediated functions ADCC and complement-mediated cytolysis (CDC). The T cell response includes, without limitation, T helper cell function, cytotoxic T cell function, inflammation/inducer T cell function, and T cell mediated immune suppression. A compound (either alone or in combination with a carrier or adjuvant) able to elicit either directly or indirectly, a specific immune response according to any of these criteria is referred to as "immunogenic." Antigen-binding fragment "activity" or "function" refers to any of the immunologic activities of an antibody, including detection, amelioration or palliation of cancer.

An "immune response" refers to induction or enhancement of an immunologic response to malignant or diseased tissue, disease-causing agents and other foreign agents to which the body is exposed. Immune responses can be humoral, as evidenced by antibody production; and/or cell-mediated, as evidenced by cytolytic responses demonstrated by such cells as natural killer cells or cytotoxic T lymphocytes (CTLs) and the cytokines produced thereby. Immune responses can be monitored by a mononuclear cell infiltrate at the site of infection or malignancy. Typically, such monitoring is by histopathology. A "cancer-specific immune response" is one that occurs against the malignancy but not against non-cancerous cells. The treatments described herein typically induce or augment a cell-mediated immune response but can also induce or augment an antibody-mediated immune response. The treatments can also influence the type of immune response to the antigen.

The compositions according to the invention are also suitable for use in inducing an antigen-specific Th1 immune response. Stimulating a Th1-type immune response can be measured in a host treated in accordance with the invention and can be determined by any method known in the art including, but not limited to, a reduction in levels of IL-4 measured before and after antigen challenge; or detection of lower (or even absent) levels of IL-4 in a treated host as compared to an antigen-primed, or primed and challenged, control treated without the compositions of the invention; an increase in levels of IL-12, IL-18 and/or IFN ($\alpha$, $\beta$ or $\gamma$, preferably IFN-$\gamma$ in a treated host as compared to an antigen-primed or-primed and challenged control; IgG2a antibody production in a treated host as compared to an untreated control; a reduction in levels of antigen-specific IgE as measured before and after antigen challenge or detection of lower (or even absent) levels of antigen-specific IgE in a treated host as compared to an antigen primed or primed and challenged untreated host. A variety of these determinations can be made by measuring cytokines made by APCs and/or lymphocytes, preferably DCsand/or T cells, in vitro or ex vivo using methods described herein and known in the art. Methods to determine antibody production include any known in the art.

The Th1 biased cytokine induction produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

The invention further includes down-regulation of type I interferon production via ligation of BDCA-2, down-regulation of Th1 immune responses via ligation of BDCA-2, and polarization of an immune response to Th2 via ligation of BDCA-2. These indications can be reversed by interfering with ligation of BDCA-2. The invention further encompasses screening for suitable moieties for interfering with ligation of BDCA-2 and compositions of these moieties.

When antigen-binding fragments are used in combination with various therapeutic agents, the administration of both usually occurs substantially contemporaneously. The term "substantially contemporaneously" means that they are administered reasonably close together with respect to time. The administration of the therapeutic agent can be daily, or at any other suitable interval, depending upon such factors, for example, as the nature of the ailment, the condition of the patient and half-life of the agent.

Therapeutic compositions can be administered by injection or by gradual perfusion over time. The antigen-binding fragments can be administered intravenously, intraperitoneally, intra-muscularly, subcutaneously, intracavity, intranodal, intrathecally or transdermally, alone or in combination with other therapeutic agents.

Another method of administration is intralesionally, for instance by injection directly into the tumor. Intralesional administration of various forms of immunotherapy to cancer patients does not cause the toxicity seen with systemic administration of immunologic agents. Fletcher et al. (1987) Lymphokine Res. 6:45; Rabinowich et al. (1987) Cancer Res. 47:173; Rosenberg et al. (1989) Science 233:1318; and Pizz et al. (1984) J. Int. Cancer 34:359.

Further, it can be desirable to administer the compositions locally to the area in need of treatment; this can be achieved by, for example, local infusion during surgery, by injection, by means of a catheter, or by means of an implant, the implant being of a porous, non-porous, or gelatinous material, including membranes, such as silastic membranes, or fibers. A suitable such membrane is Gliadel® provided by Guilford sciences.

The fact that ligation of BDCA-2 with anti-BDCA-2 monoclonal antibody (AC144) induces intracellular $Ca_2^+$ mobilization indicates that plasmacytoid DC (and all other cells which express BDCA-2) can be functionally modulated by triggering of BDCA-2 signaling or inhibition of triggering of BDCA-2 signaling. Regarding functional modulation of DC, the following aspects are encompassed by the claims:

A) Induction and down-regulation of $CD4^+$ and $CD8^+$ T cells responses.

B) Polarization of the immune response towards tolerance or immunity

C) Polarization of CD4+ T cell responses towards Th1 cell development, Th2 cells development or Th3/T-regulatory-1 CD4+ T cell development. The latter down-regulate immune responses, possibly via secretion of TGF-$\beta$ and/or IL-10.

D) DC are usually thought of as antigen-presenting cells for T cells. However, recent studies from several laboratories have shown that they have important roles in B-cell activation and regulation of antibody synthesis. B cell responses can therefore be modulated via BDCA-2 on DCs. The same can also be true for NK cell responses.

As type I interferon can induce Th1 type immune responses in humans (Parronchi et al. (1996) Eur. J. Immunol. 26:697-703), triggering of BDCA-2 polarizes $CD4^+$ T cell responses towards Th2 cell development, whereas inhibition of BDCA-2 signaling polarizes $CD4^+$ T cell responses towards Th1 cell development. The invention thus encompasses the polarization of $CD4^+$ T cell responses towards Th2 or Th1 cell development by triggering of BDCA-2 signaling or inhibition of triggering of BDCA-2 signaling, respectively.

All publications cited herein are hereby incorporated herein by reference in their entirety. The following examples are provided to illustrate, but not limit, the invention.

EXAMPLE 1

Generation of DC-specific mAb

Five 6-8 week old female Balb/c mice (Simonsen Laboratories, Gilroy, Calif.) were inoculated with approximately $5\times10^5$ to $1\times10^6$ purified HLA-DR$^+$lin$^-$ blood DC under anesthesia on d 0, 4, 7, 11, and 14 in the right hand footpad, and approximately $1\times10^6$ HLA-A2$^+$ Bristol-8 B lymphoblastoma cells in the left hand footpad on d −3, 0, 4, 7, 11, and 14. Both cell types-were incubated with 1:100 PHA (Gibco/BRL, Gaithersburg, Md.) for 10 min at room temperature and washed with PBS before injection. This treatment provides non-specific adjuvant effects and obviates the need for adjuvants such as Freund's adjuvant.

On d 15, one day after the fifth injection of HLA-DR$^+$lin$^-$ DC, the mouse right hand popliteal lymph nodes were removed. A lymphocyte suspension was prepared and the cells were fused to SP2/0 Ag14 myeloma cells using a modification of the method described by Kohler and Milstein (1975) Nature 256:495. Fused cells were plated on 96-well plates in DMEM supplemented with 20% FCS (HyClone, Logan, Utah), 2 mmol/L Lglutamine, 15 mmol/L Hepes, 10 mmol/L hypoxanthine (Gibco/BRL), and placed in a 37° C. incubator with 9% $CO_2$.

When visible hybridoma colonies were apparent, supernatants from these wells were screened by flow cytometry for antibody secretion and for non-reactivity (<1% positive cells) to PBMC. Briefly, a mixture of rat anti-mouse kappa mAb-conjugated polystyrene beads (2.5 µm in diameter, Interfacial Dynamics Corp., Portland, Oreg.) and PBMC was incubated with 50 µL hybridoma supernatant for 20 min at room temperature. The bead/cell mixture was then washed twice with PBS, pH 7.4, containing 5 mmol/L EDTA and 0.5% BSA (PBS/EDTA/BSA), and binding of mouse IgM, IgG1, IgG2a and IgG2b from the supernatants to the beads and the test cells was detected by staining with PE conjugated rat anti-mouse IgM mAb (clone X54, BD Biosciences, San Jose, Calif.), rat anti-mouse IgG1 mAb (clone X56, BD Biosciences) and rat anti-mouse IgG2 mAb (clone X57, BD Biosciences). PBMC and polystyrene beads can easily be discriminated in the flow cytometric analysis by scatter signals.

Culture supernatants which fulfilled the screening criteria of the first round were then screened by flow cytometric analysis for reactivity to a significant proportion of blood DC. Briefly, a mixture of rat anti-mouse mAb-conjugated polystyrene beads and enriched blood DC (PBMC depleted of B cells, T cells and monocytes) was incubated with 50 µl hybridoma supernatant for 20 min at room temperature. The mixture was then washed twice with PBS/EDTA/BSA, and stained with PE-conjugated rat anti-mouse IgM mAb, rat anti-mouse IgG1 mAb, and rat anti-mouse IgG2 mAb to detect binding of mouse IgM, IgG1, IgG2a and IgG2b from the supernatants to the beads and the enriched blood DC. For discrimination of $HLA-DR^+$ DC from $HLA-DR^-$ cells in the flow cytometric analysis, the bead/cell mixture was washed once, free binding sites of the PE-conjugated rat anti-mouse IgG2 mAb and the bead-conjugated rat anti-mouse κ mAb were saturated by incubation with 100 µg/ml mouse IgG2a for 5 min at room temperature, and the mixture was counterstained with anti-HLA-DR-FITC (cloneAC122, IgG2a).

Selected hybridoma cells were expanded in culture, stocks were frozen in liquid nitrogen, subclones were established by limiting dilution, and series of positive subclones were also frozen in liquid nitrogen. The isotype of the mAb was determined by the ISOTYPE Ab-STAT Kit (SangStat Medical Corp., Palo Alto, Calif.).

For mAb production, hybridoma cells were either grown as an ascites tumor in Balb/c mice, with collection of mAb-rich ascites fluid, or in cell culture (roller culture or hollow-fiber culture), with collection of mAb-rich culture supernatant. Pure IgG mAb was prepared from ascites fluid or cell culture supernatant by Protein A affinity chromatography followed in some cases by hydrophobic interaction chromatography and stored in PBS with 5 mmol/L EDTA and 0.05% sodium azide at 4° C. Purified mAb were conjugated to FITC (Sigma, St. Louis, Mo.), PE (Cyanotech Corp., Kailua Kona, Hi.), Cy5 (Amersham Life Science Inc., Arlington, Heights, Ill.), APC (Europa Bioproducts Ltd., Cambridge, UK), biotin (Pierce, Rockford, Ill.) and colloidal super-paramagnetic beads (approximately 50 nm in diameter, Miltenyi Biotec GmbH, Bergisch Gladbach, Germany) according to standard techniques. Hermanson (1996) Bioconjugate Techniques. Academic Press Inc., San Diego, 785 pp.; Aslam et al. (1998) Bioconjugation: protein coupling techniques for the biomedical sciences. Macmillan Reference Ltd., London, 833 pp.; and Kantor et al. (1997) Magnetic cell sorting with colloidal superparamagnetic particles. In, Cell Separation Methods and Applications. Recktenwald et al. Eds. Marcel Dekker Inc. New York, pp. 153-173.

Cell Preparations

Buffy coats from normal healthy volunteers were obtained from the Institute for Transfusionmedicine, Hospital Merheim, Cologne, Germany. PBMC were prepared from buffy coats by standard Ficoll-Paque (Pharmacia, Uppsala, Sweden) density gradient centrifugation.

Peripheral blood leukocytes were prepared from buffy coats by lysis of erythrocytes in isotonic ammonium chloride buffer (155 mmol/L $NH_4Cl$, 10 mmol/L $KHCO_3$ and 0.1 mM EDTA). Hansel et al. (1991) J. Immunol. Met. 145:105-110. $CD4^+lin^-$ blood DC were isolated from PBMC by two-step immunomagnetic cell sorting using MACS® as described in detail elsewhere. Robert et al. (1999); and Miltenyi et al. (1999) High gradient magnetic cell sorting. In, Flow cytometry and cell sorting. Ed., Radbruch. Springer-Verlag, Berlin. pp. 218-247. Briefly, monocytes, T cells, and NK cells were depleted using mAb against CD3 (Clone BW264/56), CD11b (clone M1/70.15.11.5), CD16 (Clone VEP-13) and in a few experiments a poorly defined antigen expressed on B cells and monocytes (clone L179). From the depleted cell fraction, blood DC were then enriched to high purity using an antibody against CD4 (M-T321). To screen hybridoma culture supernatants (see above), blood DC were merely partially enriched by immunomagnetic depletion of T cells, B cells and monocytes based on CD3 and L179 antigen expression.

$CD1c^-$, $BDCA-2^-$, and BDCA-3-expressing cells were isolated from PBMC or tonsils by indirect magnetic labeling with PE- or FITC-conjugated mAb (AD5-8E7, AC144 and AD6-5E8, respectively) as primary reagent and anti-PE or anti-FITC mAb-conjugated microbeads (Miltenyi Biotec GmbH) as secondary reagent, and enrichment of labeled cells by magnetic cell separation using MACS® (Miltenyi Biotec). In some experiments, $BDCA-3^+$ cells were isolated based on direct magnetic labeling with anti-BDCA-3 mAb (AD5-5E8)-onjugated microbeads. Highly pure $CD1c^+$ blood DC without contaminating $CD1c^+$ B cells were obtained by immunomagnetic depletion of CD18+ B cells using CD19 mAb-conjugated microbeads (Miltenyi Biotec GmbH) followed by immunomagnetic enrichment of $CD1c^+$ cells. Basophils were purified from PBMC by immunomagnetic depletion of non-basophils based on indirect magnetic labeling of CD3-, CD7-, CD14-, CD15-, CD36-, CD45RA-, and HLA-DR-expressing cells with a magnetic labeling kit (Miltenyi Biotec). $CD14^+$ monocytes, $CD34^+$ hematopoietic progenitor cells and $CD3^+$ T cells were immunomagnetic purified based on direct magnetic labeling with CD14, CD34 and CD3 mAb-conjugated microbeads (Miltenyi Biotec GmbH), respectively.

Cell Culturing

For generation of "immature" monocyte-derived DC (Mo-DC), purified $CD14^+$ monocytes were cultured at a cell density of $5\times10^5$ to $1\times10^6$ cells/ml in medium [RPMI 1640 (Gibco/BRL) supplemented with 2 mmol/L L-glutamine, 10% FCS (Sigma), 100 mmol/L sodium pyruvate (Gibco/BRL), 100 U/ml penicillin (Gibco/BRL), and 100 µg/ml streptomycin (Gibco/BRL)] at 37° C. in a humidified 5% $CO_2$-containing atmosphere in the presence of 500-1000 U/ml rIL-4 (PeproTech, Rocky Hill, N.J.) and 100 ng/ml rGM-CSF (PeproTech) for 7 d. For generation of "mature" Mo-DC, "immature" Mo-DC were washed once and cultured in medium in the presence of 20 ng/ml TNF-α (PeproTech) for another 3 d. For generation of $CD34^+$ hematopoietic progenitor cell-derived DC (CD34-DC), purified CD34+ cells were cultured at a cell density of $5\times10^4$ cells/ml in medium in the presence of 100 ng/ml rFlt3-Ligand (PeproTech), 0.5 ng/mL rTGF-β1 (PeproTech), 10 ng/ml rTNF-α, 20 ng/ml rSCF (PeproTech) and 100 ng/ml rGM-CSF for 11 d. Freshly isolated $CD4^+lin^-$ blood DC were cultured at a cell density of $5\times10^5$ to $1\times10^6$ cells/ml in medium in the presence of 10 ng/ml rIL-3 (PeproTech) for up to 48 h. Isolated CD1c-, BDCA-2-, and BDCA-3-expressing DC were cultured at a cell density of $5\times10^5$ to $1\times10^6$ cells/ml in medium without any cytokines or in the presence of 10 ng/ml rIL-3, 20 ng/ml IL-4 (PeproTech) and 100 ng/ml GM-CSF for up to 48 h.

EXAMPLE 2

Flow Cytometric Analysis of Blood DCs

A FACScalibur (BD Biosciences) was used for one-, two-, three- or four-color flow cytometry. Data of $5\times10^3$ to $2\times10^5$ cells per sample were acquired in list mode and analyzed using CellQuest software (BD Biosciences).

The following mAb (clone names) were used in this study for flow cytometry: CD1a (HI149), CD10 (HI10a), CD11a (G43-25B), CD11c (B-ly6), CD25 (M-A261), CD27 (M-T271), CD32 (FL18.26), CD38 (HIT2), CD40 (5C3), CD43 (IG10), CD54 (HA58), CD62L (Dreg 56), CD64 (10.1), CD69 (FN50), CD98 (UM7F8), anti-HLA-DQ (TU169), and anti-TCRαβ T1OB9.1A-31 from PharMingen, San Diego, Calif.; CD2 (S5.2), CD8 (SK1), CD13 (L138), CD14 (MFP9), CD19 (SJ25-C1), CD33 (P67.6), CD34 (8G12), CD45RO (UCHL-1), CD56 (NCAM16.2), CD71 (L01.1), CD123 (9F5), anti-IgD (TA4.1), anti-mouse IgG1 (X56), anti-mouse IgG2 (X57), and anti-mouse IgM (X54) from BD Biosciences; CD5 (CLB-T 11/11, 6G4), CD7 (CLB-T-3A1/1, 7F3), CD16 (CLB-FcR gran/1, 5D2), CD45RA (F8-11-13), CD80 (CLB-DALI) from CLB, Amsterdam, Netherlands; CD18 (7E4), CD23 (9P25); CD58 (AICD58), CD77 (38.13), CD83 (HB15A), CD86 (HA5.2B7), CD116 (SC06) from Coulter Immunotech, Marseilles, France; CD4 (M-T321), CD11b (MI/70.15.11.5), CD14 (TÜK4), CD15 (VIMC6), anti-HLA-DR (910/D7), anti-AC133 (AC133/1), and anti-TCRαβ (BW242/412) from Miltenyi Biotec GmbH, CD36 (AC106), CD123 (AC145), anti-HLA-DR (AC122 and AC123) and anti-GPA (AC107) from Amcell, Sunnyvale, Calif.; CD1c (M241) from Ancell, Bayport, Minn.; polyclonal anti-IgG, anti-IgM (SA-DA4), polyclonal anti-kappa, and polyclonal anti-lambda from Southern Biotechnology Associates, Birmingham, Ala.; CD61 (VIPL2) from W. Knapp, Institute of Immunology, University of Vienna, Vienna, Austria; CD44 (IM7) from J. Moll, Forschungszentrum Karlsruhe, Karlsruhe, Germany; CD20 (H147) from Caltag Laboratories, Burlingame, Calif.; anti-CLA (HECA-452) from E. Butcher, Department of Pathology, Stanford University, Stanford, Calif.; anti-$Fc_\epsilon RI$ (15-1) from J. P. Kinet, Molecular Allergy and Immunology Section, National Institute of Allergy and Infectious Diseases, National Institutes of Health, Rockville, Md.; CD11c (Ki-M1) from M. R. Parwaresch, Department of Pathology, Christian Albrechts University, Kiel, Germany; CMRF-44 and CMRF-56 from D. N. Hart, Mater Medical Research Institute, Mater Misericordiae Hospitals, South Brisbane, Queensland, Australia; and anti-HLA-A, -B, -C (W6/32) from Sigma.

All antibodies were used as FITC-, PE-, biotin- or Cy5-conjugated mAb. For indirect immunofluorescent staining with biotinylated mAb, streptavidin-APC (BD Biosciences) was used. To exclude dead cells in the flow cytometric analysis, cells were stained with propidium iodide. To minimize Fc receptor-mediated mAb binding, cells were stained in most experiments in the presence of FcR-blocking reagent (Miltenyi Biotec GmbH) containing human IgG.

Microscopic Analysis

Cells were spun down on slides in a cytocentrifuge (Cytospin 3, Shandon, Pittsburgh, Pa.). For fluorescence microscopy, slides were air dried overnight after cytocentrifugation and mounted with Fluoromount G (Southern Biotechnology Associates). For May Grunwald/Giemsa staining, slides were air dried for at least 2 h after cytocentrifugation, stained in May Grunwald/Giemsa solution (Merck, Darmstadt, Germany) for 2 min at room temperature, rinsed thoroughly in distilled water, stained in Giemsa solution (Merck) for 15 min at room temperature, washed repeatedly in distilled water, and air dried for at least 2 h. A Zeiss Axioscop, microscope (Zeiss, Oberkochen, Germany) was used for analysis. Digital pictures Were made using the Xillix Micro-Imager MI1400-12X (Xillix, Vancouver, Canada).

EXAMPLE 3

Cross-inhibition, Co-capping and Co-internalization Analysis

To analyze whether two different mAb clones recognize the same (or a closely related) antigen epitope, cross-inhibition binding assays were performed. Between $1\times10^6$ and $2\times10^6$ cells were pre-incubated with one of the two mAb clones at a concentration of about 100 µg/ml for 10 min at 4° C., and then stained With a PE-conjugate of the other mAb clone at its optimal titer for another 5 min at 4° C. PBMC were used to analyze cross-inhibition of BDCA-2-, BDCA-3-, and BDCA-4-specific mAb clones and MOLT-4 cells were used to analyze cross-inhibition of CD1c-specific mAb clones. Cell staining was analyzed by flow cytometry.

To ascertain whether AD5-5E8 and AD5-14H12 recognize the same antigen (or the same antigen-complex) a co-capping assay was performed. Briefly, BDCA-3-expressing cells were isolated from PBMC by indirect magnetic labeling with PE-conjugated AD5-14H12 mAb and anti-PE mAb-conjugated microbeads, and isolated cells were incubated for 30 min at 37° C. to induce capping of the mAb-antigen complex. Afterwards, cells were washed with ice cold PBS/EDTA/BSA supplemented with 0.1% sodium azide (PBS/EDTA/BSA/azide), and stained with FITC-conjugated AD5-5E8 mAb in PBS/EDTA/BSA/azide for 10 min at 4° C. Cell staining was analyzed by fluorescence microscopy.

A co-internalization assay was used to investigate whether AC144 and AD5-17F6 recognize the same antigen (or the same antigen-complex). Briefly, $1\times10^6$ PBMC were incubated with 50 µg/ml AC144 mAb for 15 min at room temperature in PBS/BSA, washed twice in PBS/BSA, and then incubated in cell culture medium at 37° C. for 30 min. To analyze whether AC144 mAb is internalized upon culturing, aliquots of the cells were stained before and after the culture period with rat anti-mouse IgG1-PE. To determine whether all AC144 mAb-binding sites were saturated with unconjugated AC144 mAb before culturing and whether any free binding sites reappear after culturing, aliquots of the cells were stained before and after the culture period with AC144-PE. To analyze whether AD5-17F6 antigen is co-internalized, aliquots were stained before and after the culture period with AD5-17F6-PE. All cells were counter stained with CD123-FITC and HLA-DR-Cy5 to be able to gate on $CD123^{bright}HLA-DR^+$ plasmacytoid DC in the flow cytometric analysis.

EXAMPLE 4

Endocytosis Assay

To assess endocytosis of blood DC subsets, purified $CD1c^+$, $BDCA-2^+$ and $BDCA-3^+$ blood DC, and (as control) purified $CD3^+$ T cells were incubated at 37° C. in medium with 1 mg/ml Lucifer yellow (LY) for 0, 15, 45, and 75 min. Afterwards, cells were washed three times in ice cold PBS/EDTA/BSA and analyzed by flow cytometry.

EXAMPLE 5

Reactivity of Isolated Blood DCs with Non-cultured Blood Cells

According to their reactivity with blood cells, the mAb listed in Table 1 could be divided into four groups: (1) AC144, AD5-13A11 and ADB-4B8; (2) AD5-17F6; (3) AD5-5E8 and AD5-14H12; and (4) AD5-8E7.

The mAb of the first group, AC144, AD5-13A11 and ADB-4B8, stain approximately 0.41±0.17% (n=10) of all PBMC (FIG. 1A). In a dot plot of forward and side scatter signals, these rare cells constitute a homogeneous cell population that is located between small resting lymphocytes and monocytes (FIG. 1B). Accordingly, these rare cells do not express the αβ T cell receptor (TCRαβ), CD14, CD19 and CD56 (FIG. 1A), lineage markers which are expressed on T cells, monocytes, B cells and NK cells, respectively. Staining of highly purified blood DC (>95% HLA-DR$^+$, TCRαβ$^-$, CD14$^-$, CD19$^-$ and CD56$^-$) reveals that the mAb of the first group are reactive with CD11c$^-$CD123$^{bright}$ blood DC (FIG. 2) but not reactive with CD11c$^+$ blood DC. To analyze whether all of them react with a single antigen, we performed two-color stainings and cross-inhibition studies. The results show that all mAb of this group recognize a single epitope of the same antigen. This antigen was named BDCA-2.

Figure 3:
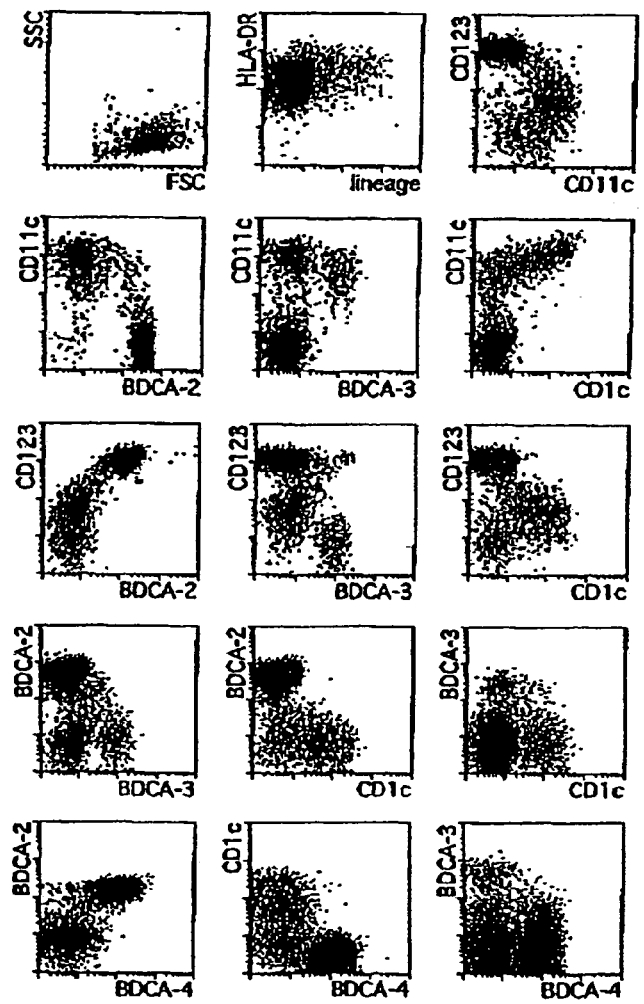
FIG. 3 depicts expression of BDCA-4 on PBMC. Shown is a two-color staining of PBMC with FITC-conjugated MAB against BDCA-2 (AC144) and PE-conjugated mAB against BDCA-4 (AD5-17F6). Note that a few single positive (BDCA-2+BDCA-4− and BDCA-2−BDCA-4+) PBMC are detected
Figures 4, 5:
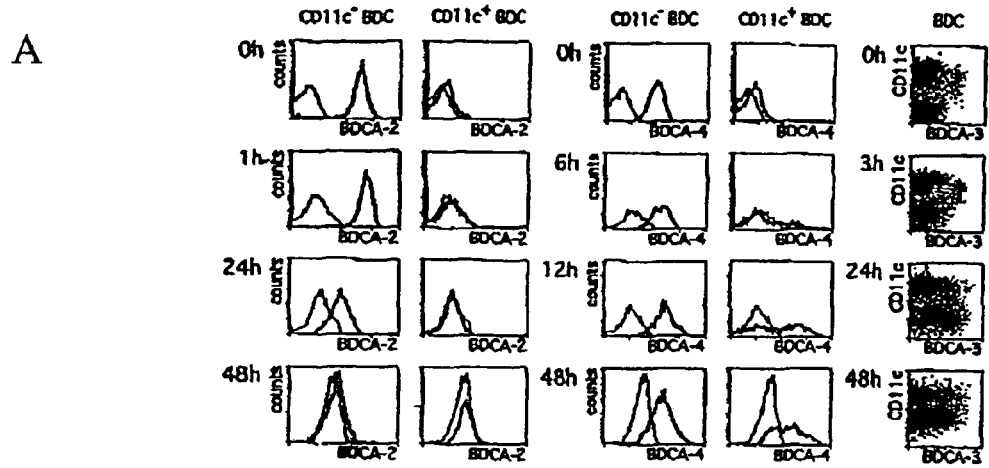
FIG. 4 shows the expressino of BDCA-2, BDCA-3 and BDCA-4 on purified blood DC after various periods of culture in the presence of IL-3. Purified blood DC were cultured for 0 h, 1 h, 3 h, 6 h, 9 h, 12 h, 18 h, 24 h, 36 h, and 48 h in the presence of rIL-3 and then flow cytometrically analyzed for the expression of CD11c, BDCAj-3, BDCA-2 and BDCA-4. (A) Histograms show staining of gated CD11c$^-$ and CD11c$^+$ blood DC with PE-conjugated anti BDCA-2 mAB (AC144) and anti-BDCA-4 mAB (AD5-17F6) (bold lines), and PE-conjugated isotype-matched control mAB (faint lines), respectively. Dot plots show staining of blood DC with CD11c-PE vs. anti BDCA-3 (AD5-5E8) biotin/streptavidin-APC. (B) Diagrams show mean fluroescence intensity (MFI) values for anti-BDCA-2-PE, anti BDCA-4-PE, and anti-BDCA-3 biotin/streptavidin-APC staining of CD11c$^-$ (▲) and CD11c$^+$ (■) DC, respectively. For BDCA-2 and BDCA-4, MFI values were calculated by subtracting the values obtained with isotype control mAb from the values obtained with the AC144 and AD5-17F6, respectively. For BDCA-3, MFI values are calculated by subtracting the values obtained without any staining mAb (autofluorescence) from the values obtained with AD5-5E8.
FIG. 5 shows the amino acid sequence of one isoform of BDCA-2 with all six exons-being expressed (SEQ ID NO:2).

As shown in FIG. 3, the mAb of the second group, AD5-17F6, recognizes the same cells among PBMC as AC144, one of the BDCA-2-specific mAb of the first group. Nevertheless, AD5-17F6 stains an antigen which is different from BDCA-2. This was unequivocally demonstrated by co-internalization experiments, where AD5-17F6 showed surface staining with equal intensity before and after anti-BDCA-2 mAb-mediated internalization of BDCA-2, and by staining of DC after culture, where AC144 mAb and AD5-17F6 mAb showed entirely different staining patterns (FIG. 4). The antigen recognized by ADS-17F6 was named BDCA-4 and is identical to neuropilin-1. He et al. (1997).

Figure 2:
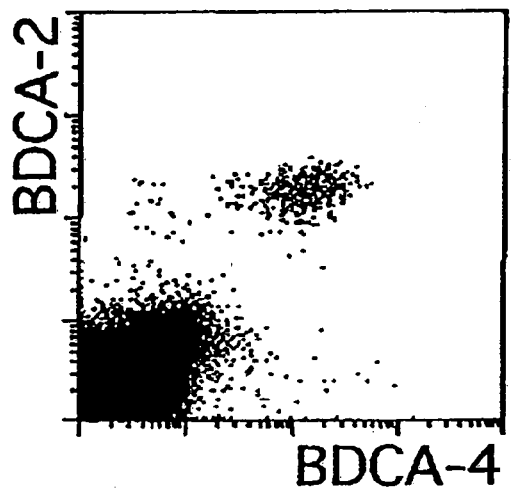
FIG. 2 shows that BDCA-2, BDCA-3, BDCA-4 and CD1c (BDCA-1) are expressed on three distinct blood DC subsets. Blood DC were isolated from PBMC by depletion of CD3, CD11b and CD16 positive cells followed by enrichment of CD4 positive cells. The purity of blood DC is demonstrated by light-scatter properties (upper-left dotplot) and anti-HLA-DR-Cy5 vs. anti-Lin-FITC (anti-TCRαβ, CD14, CD19 and CD56) staining (upper-middle dotplot). Note that only few lin$^+$ cells are present. Expression of BDCA-2, BDCA-3, BDCA-4 and CD1c on blood DC is characterized in a series of two-color stainings with PE- and FITC-conjugated mAb against CD11c, CD123 and the antigens themselves. Note that BDCA-2, BDCA-3, BDCA-4 and CD1c are exclusively expressed on only one of three distinct blood DC subsets each. The subsets are defined according to staining of blood DC with CD123-PE vs. CD11c-FITC (upper-left dotplot): CD11c$^-$CD123$^{bright}$ blood DC; CD11c$^{bright}$CD123$^{dim}$ blood DC; and CD11c$^{dim}$CD123$^-$ blood DC.

The mAb of the third group, AD5-5E8 and AD5-14H12, stain approximately 0.04±0.01% (n=10) of all PBMC (FIG. 1A). According to scatter signals (FIG. 1B) and counterstaining with mAb against the TCRαβ, CD14, CD19 and CD56 (FIG. 1A), these cells are distinct from lymphocytes and monocytes and slightly larger than the cells recognized by the antibodies of the first group. Accordingly, staining of blood DC shows that a different subset is recognized by AD5-5E8 and AD5-14H12, namely CD11c$^{dim}$CD123$^-$ blood DC (FIG. 2). According to two-color stainings, cross-blocking studies and co-capping experiments both mAb appear to recognize two spatially unrelated epitopes of the same antigen. We named this antigen BDCA-3.

Figure 6:
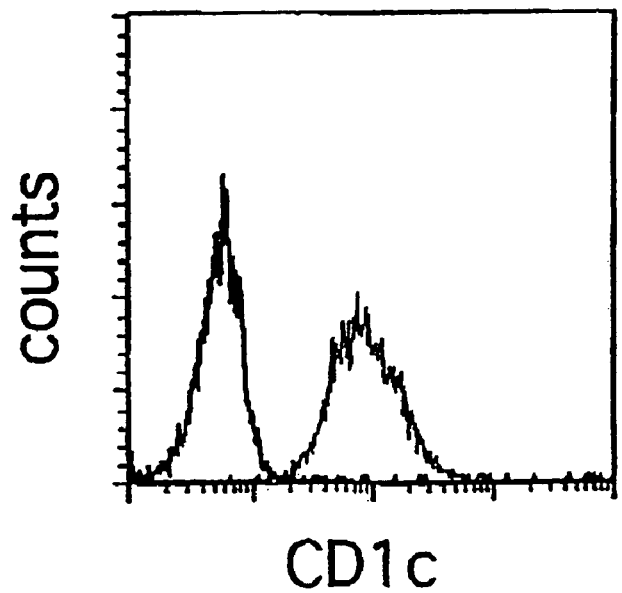
FIG. 6 shows that BDCA-1-specific mAb AD5-8E7 blocks binding of the CD1c mAb M241 to MOLT-4 cells. MOLT-4 cells were pre-incubated with saturating amounts of AD5-8E7 mAb (bold line) or an isotope control mAb (faint line) and then stained with PE-conjugated CD1c mAb (M241).

The fourth group, mAb AD5-8E7, reacts with up to 2.39±0.96% (n=10) of unfractionated PBMC (FIG. 1A). Light-scatter analysis (FIG. 1B) and counter-staining of the lineage markers TCRαβ, CD14, and CD19 reveal that the mAb is not reactive to T cells and monocytes, but is reactive to a major subset of small resting CD19$^+$ B cells. Staining of purified DC shows that AD5-8E7, in addition to B cells, stains a third subset of blood DC distinct from those subsets recognized by the mAb of the first and the second group, namely CD11c$^{bright}$CD123$^{dim}$ blood DC. A significant proportion of the CD11C$^{bright}$CD123$^{dim}$ blood DC expresses CD56 (see below). For this reason, some AD5-8E7-reactive PBMC stain for CD56 (FIG. 1A). AD5-8E7 is not reactive to purified NK cells. The antigen recognized by AD5-8E7 was initially named BDCA-1 as it appeared to be a new antigen. However, it later transpired that AD5-8E7 completely blocks binding of the CD1c mAb M241 to MOLT-4 cells (FIG. 6). Thus, the antigen recognized by AD5-8E7 is CD1c.

None of the mAb listed in Table 1 is reactive with granulocytes, platelets, erythrocytes, purified basophils and purified CD34$^+$ hematopoietic progenitor cells.

EXAMPLE 6

Expression of BDCA-2, BDCA-3 and BDCA-4 on Cultured Blood DC, Mo-DC and CD34-DC

Figure 7:
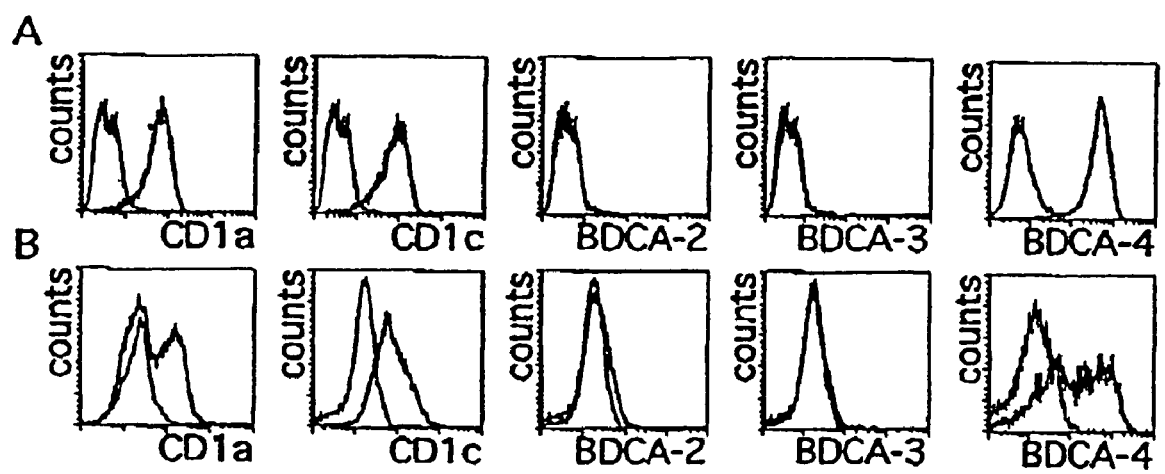
FIG. 7 shows the expression of BDCA-2, BDCA-3 and BDCA-4 on Mo-DC and CD34$^+$ cell-derived DC (CD34-DC). CD14$^+$ monocytes and CD34$^+$ hematopoietic progenitor cells were immunomagnetically purified via direct magnetic labeling with CD14 and CD34 mAb-conjugated microbeads, respectively. Purified monocytes were cultured for 7 d in the presence of rGM-CSF and rIL-4, and purified CD34-DC were cultured for 11 d in the presence of rflt3-ligand, rTGF-β1, rTNF-α, rSCF and RGM-CSF. After the culture period, cells were stained with CD1a-FITC, CD1c-PE (AD5-8E7), anti-BDCA-2-PE (AC114), anti-BDCA-3-PE (AD5-5E8) and anti-BDCA-4-PE (AD5-17F6). Histograms show staining of (A) Mo-DC and (B) CD34-DC (bold lines), respectively. The faint lines show staining with isotype control mAb. Except for the left-most histogram (CD1a staining), gated CD1a$^+$ cells are shown in (B).

Freshly isolated plasmacytoid CD11c$^-$ blood DC depend on IL-3 for survival and maturation, whereas survival and maturation of CD11c$^+$ blood DC is far less cytokine-dependent. Expression of BDCA-2, BDCA-3 and BDCA-4 on CD11c$^-$ and CD11c$^+$ blood DC was analyzed after 0 h, 1 h, 3 h, 6 h, 9 h, 12 h, 18 h, 24 h, 36 h, and 48 h of culture of total blood DC in the presence of rIL-3. The results are shown in FIG. 4. Expression of BDCA-2 is completely down-regulated within 48 h on CD11c$^-$ blood DC. In contrast, BDCA-4 is even further up-regulated on CD11c$^-$ blood DC and, unlike BDCA-2, is also expressed to a high level on most, if not all, CD11c$^+$ DC. Expression of BDCA-3 is rapidly induced on CD11c$^-$ blood DC, reaching the highest expression level after 24 h. Thereafter, BDCA-3 expression appears to be down-regulated again. Analyzing the expression of BDCA-3 on CD11c$^+$ blood DC is complicated by the fact that BDCA-3$^-$CD11c$^{bright}$ and BDCA-3$^+$CD11c$^{dim}$ subsets are present at the onset of the culture. Expression of BDCA-3 remains unchanged at least until 6 h of culture on the BDCA-3$^+$CDllc$^{dim}$ blood DC population, and is induced within 3 h on at least some cells of the BDCA-3$^-$CD11c$^{bright}$ blood DC subset. Expression of BDCA-2, BDCA-3 and BDCA-4 on Mo-DC and CD34$^-$ DC Functional CD1a$^+$ DC were generated ex vivo from monocytes and from CD34$^+$ hematopoietic progenitor cells. Bender et al. (1996); Pickl et al. (1996; Romani et al. (1994); Sallusto et al. (1994); Caux et al. (1992); Mackensen et al. (1995); Szabolcs et al. (1995); Herbst et al. (1996); de Wynter et al. (1998); and Strunk et al. (1996). FIG. 7 shows that Mo-DC, which were generated by culturing monocytes for 7 d in the presence of rGM-CSF and IL-4 and CD34-DC, generated by culturing CD34+ hematopoietic progenitor cells for 11 d in the presence of rFlt3-Ligand, rTGF-β1, rTNF-α, rSCF and rGM-CSF, express CD1a, CD1c and BDCA-4, but neither BDCA-2 nor BDCA-3.

EXAMPLE 7

Internalization of BDCA-2 Upon Anti-BDCA-2 mAb-mediated Cross-linking

Figure 8:
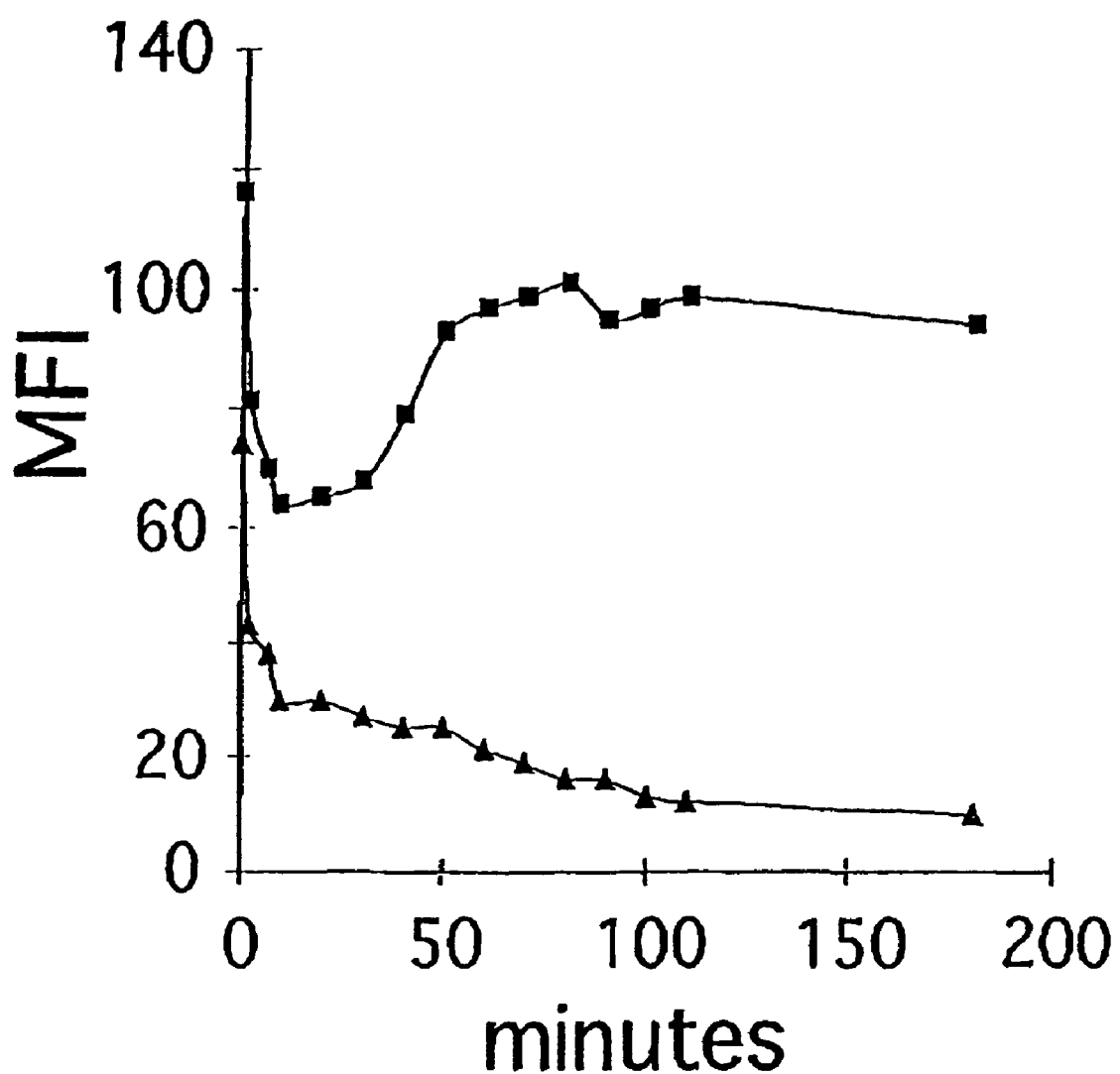
FIG. 8 shows that culturing of anti-BDCA-2 mAb-labeled BDCA-2$^+$ cells results in rapid mAb internalization. PBMC were labeled at 4° C. with FITC-conjugated anti-BDCA-2 mAb (AC144, IgG1), incubated at 37° C. for the time periods indicated, and were then stained at 4° C. with PE-conjugated rat anti-mouse IgG1 mAb (X56) and Cy5-conjugated CD123 mAb (AC145, IgG2a). Shown are MFI values of anti-BDCA-2-FITC (■) and rat anti-mouse IgG1 mAb-PE (▲) staining of gated BDCA-2$^+$CD123$^+$ cells.

The possibility that 37° C. incubation of anti-DCA-2 mAb-labeled BDCA-2$^+$ cells results in mAb internalization was addressed by staining of PBMC with FITC-conjugated AC144 mAb (IgG1). Then, following incubation at 37° C., remaining cell surface associated mAb was detected by staining with PE-conjugated rat anti-mouse IgG1 mAb. As shown in FIG. 8, when cells were incubated at 37° C., the intensity of the rat anti-mouse IgG1-PE staining decreases extremely rapidly to background levels. In contrast, the intensity of the AC144-FITC staining decreases only temporarily to a level of approximately 50%, but thereafter nearly returns to the pre-incubation level. This demonstrates that BDCA-2 is internalized upon anti-BDCA-2 mAb cross-linking, with kinetics similar to receptor-mediated endocytosis. The transient decrease in AC144-FITC staining intensity is probably due to patching and capping of the BDCA-2/anti-BDCA-2 mAb complex before endocytosis.

EXAMPLE 8

Morphology of Isolated CD1c$^+$, BDCA-2$^+$ and BDCA-3$^+$ Blood DC

Figure 9:
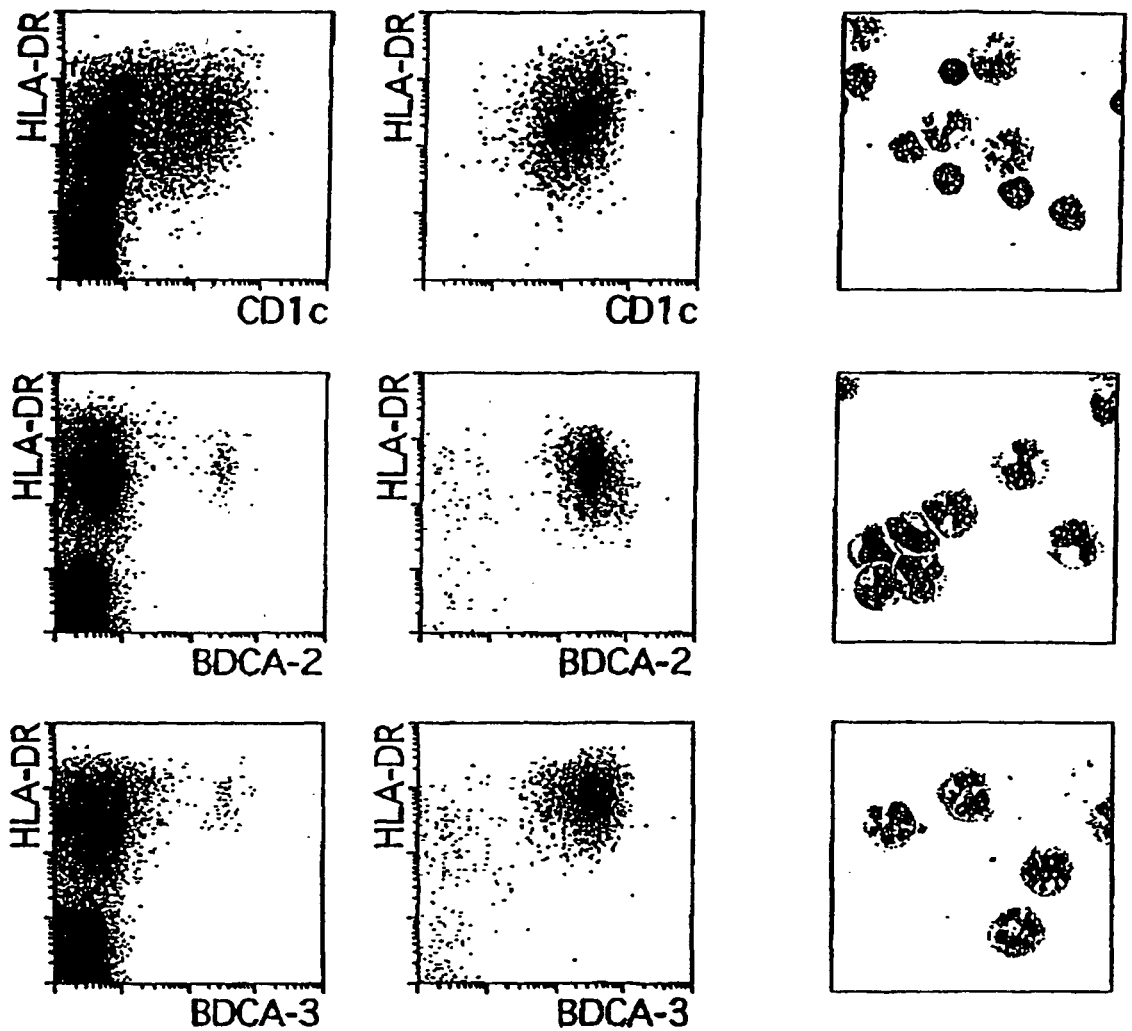
FIG. 9 shows the morphology of immunomagnetically purified CD1c$^+$, BDCA-2$^+$ and BDCA-3$^+$ blood DC. CD1c$^+$, BDCA-2$^+$ and BDCA-3$^+$ cells were isolated from PBMC by indirect magnetic labeling with PE-conjugated primary mAb (AD5-8E7, AC144 and AD5-5E8) and anti-PE mAb-conjugated microbeads followed by enrichment of labeled cells by magnetic cell separation using MACS® (Miltenyi Biotec). The dotplots show staining of PBMC with HLA-DR-FITC and the PE-conjugated mAb before (left dotplots) and after (right dotplots) magnetic enrichment of CD1c$^+$ (upper dotplots) BDCA-2$^+$ (middle dotplots) and BDCA-3$^+$ (lower dotplots) cells, respectively. The three pictures on the right side show May Grunwald/Giemsa staining of isolated CD1c$^+$ (upper picture), BDCA-2$^+$ (middle picture) and BDCA-3$^+$ cells after cytocentrifugation. Note that small lymphocytes can be seen in the picture of the enriched CD1c$^+$ cells. These are CD1c$^+$ B cells.

CD1c$^+$, BDCA-2$^+$ and BDCA-3$^+$ cells were isolated from PBMC by indirect magnetic labeling with PE-conjugated primary mAb and anti-PE Ab-conjugated microbeads and enrichment of labeled cells by magnetic cell separation using MACS® (Miltenyi Biotec) (FIG. 9). On May Grunwald/Giemsa staining of cytocentrifuge slides (FIG. 9), freshly isolated BDCA-2-expressing cells display the typical lymphoplasmacytoid morphology of CD11c− CD4+lin−DC from blood and tonsils: that is, medium-sized round cells with oval or indented nuclei. In contrast, both freshly isolated CD1c+ blood DC as well as freshly isolated BDCA-3+ blood DC display the typical morphological characteristics of CD11c+ CD4+lin−DC from blood or tonsils: that is, less rounded cells with short cell processes and more hyperlobulated nuclei. In addition to CD1c+ BDC, CD1c+ B cells with the typical morphology of small resting lymphocytes can be seen on the cytocentrifuge slides of isolated CD1c+ PBMC. Highly pure CD1c+ BDC are obtained if, prior to the enrichment of CD1c+ cells, CD19+ B cells are magnetically depleted from PBMC.

EXAMPLE 9

Surface Phenotype of CD1c+, BDCA-2+ and BDCA-3+ Blood DC

The phenotype of BDCA-2+ and BDCA-3+ blood DC was analyzed by two-color immunofluorescence with PE- and FITC-conjugated mAb. For analysis of CD1c+ blood DC, three-color stainings were performed using CD19-Cy5 for exclusion of B cells. The results of the phenotypic analysis are shown in Table 2 and can be summarized as follows: none of the blood DC subsets express CD1a, CD8, CD15, CD16, CD19, CD20, CD23, CD25, CD27, CD34, CD61, CD69, CD7.1, CD77, CD80, CD83, glycophorin A (GPA), TCRαβ, AC133, IgD, IgM and the CMRF-56 antigen. All blood DC subsets express CD43, CD44, CD54 and MHC class I molecules at a similar level. BDCA-2+ blood DC differ from the other two subsets in that they do not express CD13, CD40, CD45RO, CD56, but CD45RA and little amounts of CD10, and in that they express lower levels of CD18, CD38, CD58, CD98, CD116 and CLA, but higher levels of CD4. CD1c+ blood DC differ from the other two subsets in that they express CD2, higher levels of MHC class11 molecules, but lower levels of CD62L, and in that they express the Fc receptors CD32, CD64 and Fc$_\epsilon$R1. Probably due to the Fc receptor-expression, CD1c+ blood DC are also positive for IgG, kappa and lambda. Furthermore, some CD1c+ DC are positive for CD14 and CD11b, whereby the level of expression inversely correlates with the level of both CD1c and CD2 expression. BDCA-3+ blood DC differ from the other two subsets in that they express CD36 at a much lower level and in that they appear to express low levels of CD5. Finally, apart from CD11c and CD123, at least one additional antigen, CD33, is useful for discrimination of all three subsets: CD33 is expressed at low levels on BDCA-2+ DC, at intermediate levels on BDCA-3+ DC and at high levels on CD1c+ DC.

TABLE 2

| Antigen | Clone | BDCA-2+ | BDCA-3+ | CD1c+ |
| --- | --- | --- | --- | --- |
| CD1a | HI149 | − | − | − |
| CD1c | M241 | − | − | + |
| CD2 | S5.2 | −/minor subset+ | − | + |
| CD4 | M-T321 | ++ | + | + |
| CD5 | CLB-T1/1, 6G4 | − | −/+ | − |
| CD7 | CLB-T3A1, 7F3 | −/minor subset+ | − | + |

TABLE 2-continued

| Antigen | Clone | BDCA-2+ | BDCA-3+ | CD1c+ |
| --- | --- | --- | --- | --- |
| CD8 | SK1 | − | − | − |
| CD10 | HI10a | −/+ | − | − |
| CD11a | G43-25B | + | ++ | + |
| CD11b | M1/7O.15.11.5 | − | − | −/+ |
| CD11c | Ki-M1 | − | + | ++ |
| CD13 | L138 | − | + | + |
| CD14 | TUK4 | − | − | −/+ |
| CD15 | VIMC6 | − | − | − |
| CD16 | CLB-FcR Gran/1 | − | − | − |
| CD18 | 7E4 | + | ++ | ++ |
| CD19 | SJ25-C1 | − | − | − |
| CD20 | HI47 | − | − | − |
| CD23 | 9P25 | − | − | − |
| CD25 | M-A251 | − | − | − |
| CD27 | M-T271 | − | − | − |
| CD32 | FL18.26 (2003) | − | − | + |
| CD33 | P67.6 | −/+ | + | ++ |
| CD34 | 8G12 | − | − | − |
| CD36 | AC106 | + | −/+ | + |
| CD38 | HIT2 | + | ++ | ++ |
| CD40 | FC3 | − | −/+ | −/+ |
| CD43 | 1G10 | + | + | + |
| CD44 | IM7 | + | + | + |
| CD45RA | F8-11-13 | + | − | − |
| CD45RO | UCHL-1 | − | + | + |
| CD54 | HA58 | + | + | + |
| CD56 | NCAM16.2 | − | −/subset+ | −/subset+ |
| CD58 | AICD58 | + | ++ | ++ |
| CD61 | VIPL2 | − | − | − |
| CD62L | DREG56 | − | + | + |
| CD64 | 10.1 | ++ | ++ | + |
| CD69 | FN50 | − | − | − |
| CD71 | LO1.1 | − | − | − |
| CD77 | 38.13 | − | − | − |
| CD80 | DAL-1 | − | − | − |
| CD83 | HB15A | − | − | − |
| CD86 | HA5.2B7 | + | ++ | +++ |
| CD98 | HIM6 | ++ | +++ | +++ |
| CD116 | SC06 | + | ++ | ++ |
| CD123 | AC145 | ++ | − | + |
| HLA-DR | AC122 | + | + | ++ |
| HLA-DQ | TU169 | + | + | ++ |
| HLA-A, B, C | W6/32 | + | + | + |
| GPA | AC107 | − | − | − |
| TCRαβ | T10B9.1A-31 | − | − | − |
| AC133 | AC133 | − | − | − |
| Fc$_\epsilon$R I | 15-1 | − | − | + |
| IgD | TA4.1 | − | − | − |
| IgG | Polyclonal | − | − | + |
| IgM | SA-DA4 | − | − | − |
| Kappa | Polyclonal | − | − | + |
| Lambda | Polyclonal | − | − | + |
| CLA | HECA-452 | ++ | +++ | +++ |
| CMRF44 | CMRF44 | − | − | −/minor subset+ |
| CMRF56 | CMRF56 | − | − | − |

EXAMPLE 10

Figure 10:
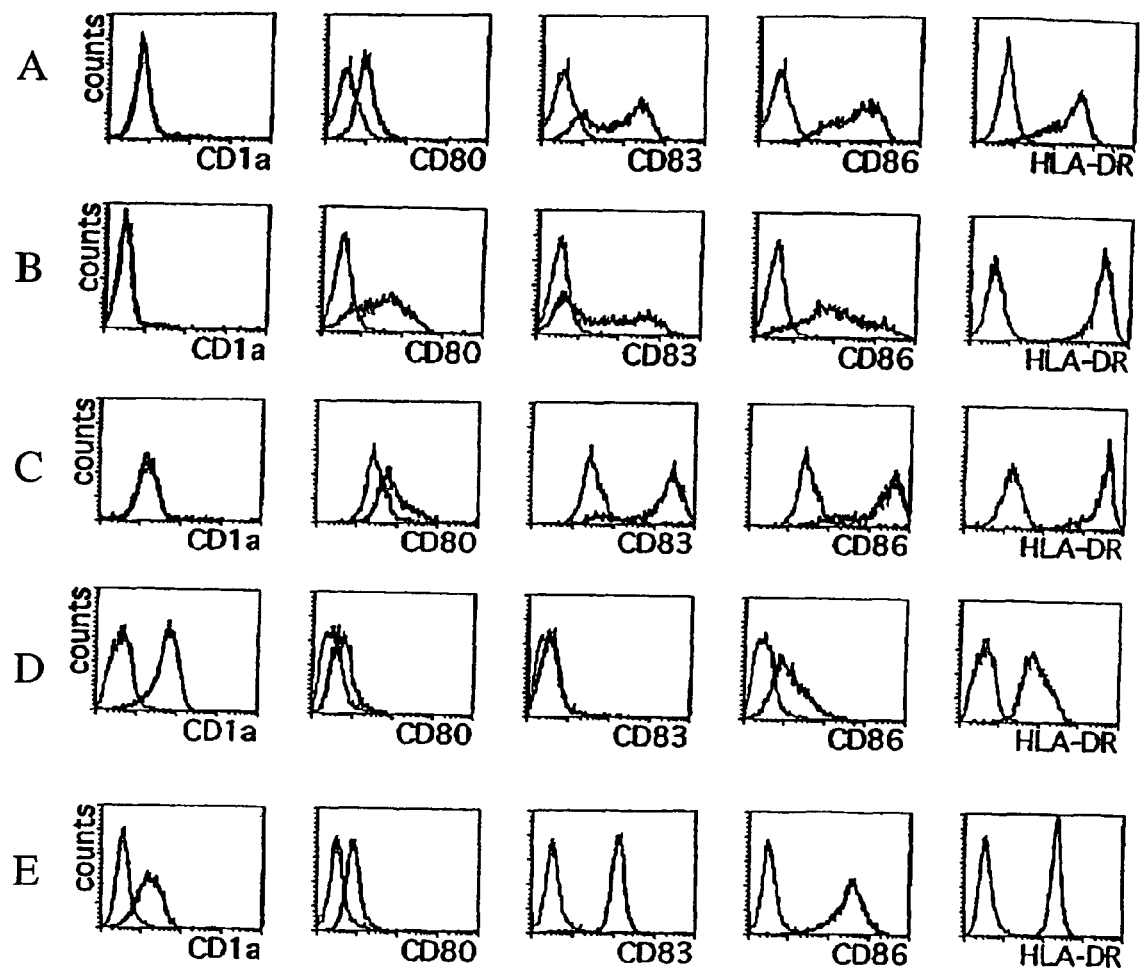
FIG. 10 shows up-regulation of MHC class II, CD83 and co-stimulatory molecules on CD1c+, BDCA-2+ and BDCA-3+ blood DC upon culturing. Purified CD1c+ (A), BDCA-2+ (C) and BDCA-3+ (B) were cultured for 1 day in medium (CD1c+ and BDCA-3+ BDC) or for 2 days in medium with rIL-3 and anti-CD40 mAb on CD32-transfected L cells (BDCA-2+ DC), respectively. "Immature" Mo-DC (D) were generated by culturing of monocytes for 7 days in medium in the presence of rGM-CSF and rIL-4. "Mature" Mo-DC (E) were generated by culturing of immature Mo-DC for another 3 days in medium in the presence of TNFα. The histograms show cell staining with CD1a-FITC, CD80-PE, CD83-PE, CD86-PE and HLA-DR-PE, respectively (bold lines). The faint lines show cell staining with isotype and fluorochrome-matched control mAb.

Expression of MHC class II, CD83 and Co-stimulatory Molecules on CD1c+, BDCA-2+ and BDCA-3+ Blood DC After Culture Freshly isolated CD1c+ blood DC and BDCA-3+ blood DC were cultured for 1 d in medium without any supplemented cytokines and freshly isolated BDCA-2+ blood DC were cultured for 2 d in medium supplemented with IL-3 and CD40 mAb on CD32-transfected fibroblasts. After the culture period, cells were analyzed for the expression of CD1a, CD80, CD83, CD86 and HLA-DR. For comparison, so-called "immature" Mo-DC, generated by culturing of monocytes for 7 d in the presence of GM-CSF and IL-4, and so-called "mature" Mo-DC, generated by culturing of "immature" Mo-DC for 3 d in the presence of TNF-α, were also included. Sallusto et al. (1995) J. Exp. Med. 182:389-400; and Sallusto et al. (1998) J. Immunol. 28:2760-2769. As shown in FIG. 10, in contrast to "immature" Mo-DC and "mature" Mo-DC, none of the blood DC subsets expresses CD1a after the culture period. However, the costimulatory molecules CD80 and CD86, the DC activation antigen CD83 (Zhou et al. (1995); Zhou et al. (1992) J. Immunol. 149:735-742; and Zhou et al. (1996) Proc. Natl. Acad. Sci. USA 93:2588-2592), and HLA-DR molecules are up-regulated upon culturing on all three blood DC subsets to a similar level as compared to mature Mo-DC. The results were not significantly different in another experiment in which all three blood DC subsets were cultured for 2 d in- medium supplemented with IL-3, IL-4 and GM-CSF. As has been previously shown for CD11c$^-$CD4$^+$lin$^-$ DC from blood and tonsils, BDCA-2$^+$ blood DC rapidly die when cultured in medium without IL-3.

EXAMPLE 11

Figure 11:
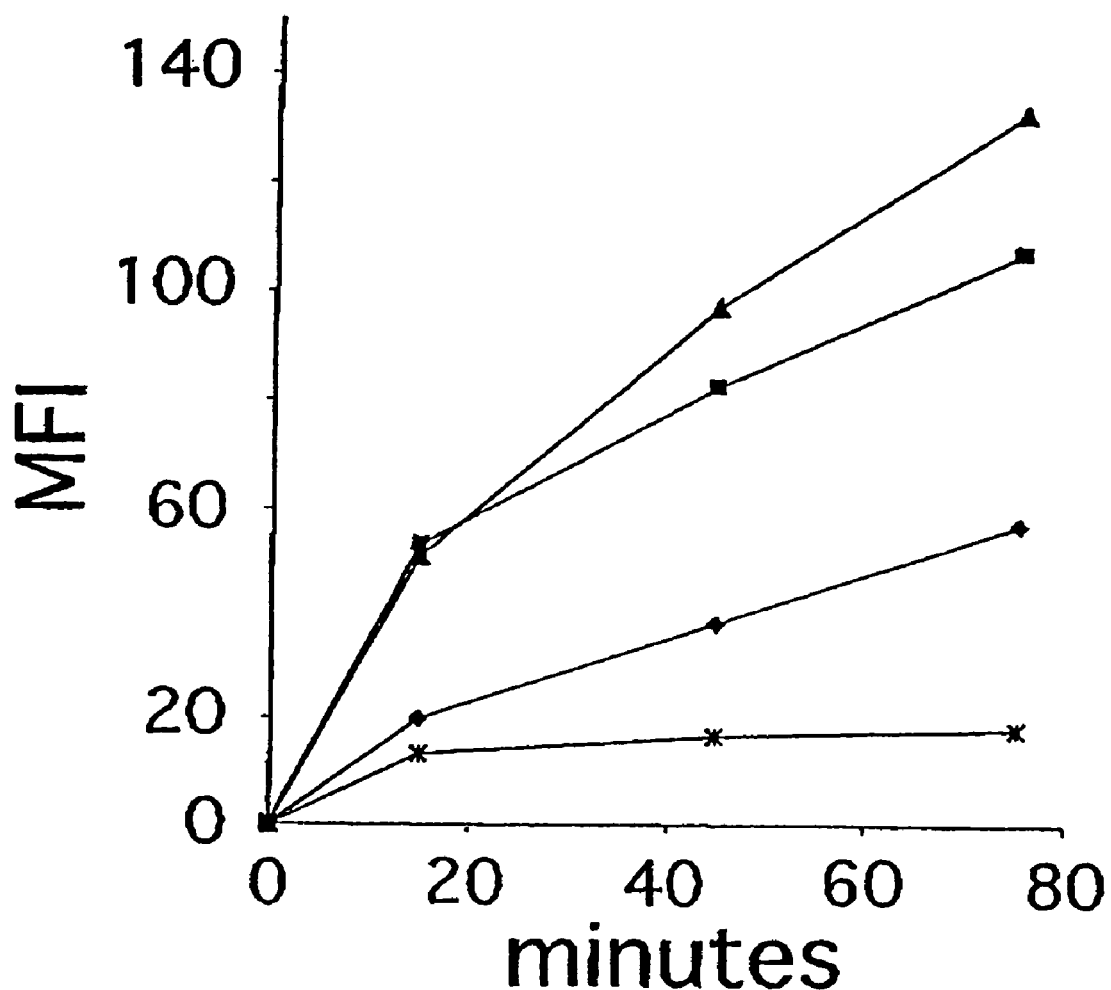
FIG. 11 shows endocytic capacity of freshly isolated CD1c+, BDCA-2+ and BDCA-3+ blood DC in comparison with purified CD3+ T cells. Isolated CD1c+ DC (♦), BDCA-2+ BDC (▲), BDCA-3+ DC (■) and CD3+ T cells (*) were incubated at 37° C. in medium with 1 mg/ml Lucifer Yellow (LY) for 0, 5, 45 and 75 min, washed three times in ice cold PBS/EDTA/BSA and were then analyzed by flow cytometry. Shown are the MFI values for LY fluorescence after subtracting the MFI values, which are obtained upon incubation at 4° C. in the absence of LY.

Endocytic Capacity of Freshly Isolated CD1c$^+$, BDCA-2$^+$ and BDCA-3$^+$ Blood DC The endocytic capacity of purified CD1c$^+$, BDCA-2$^+$ and BDCA-3$^+$ blood DC, and, as a control, of purified CD3$^+$ T cells was examined by culturing the cells at 37° C. in the presence of LY and analyzing the uptake of LY after various periods of time by flow cytometry. As shown in FIG. 11, unlike purified CD3$^+$ T cells, purified CD1c$^+$ blood DC, BDCA-3$^+$ blood DC, and to some extent also BDCA-2$^+$ blood DC have the ability to endocytose LY. Similar results were obtained using FITC-Dextran. The endocytic capacities of all blood DC populations are much lower if compared with Mo-DC.

The amino acid sequence of BDCA-4 was obtained by purifying the antigen with AD5-17F6 mAb (AD5-17F6 affinity column) and analyzing the purified antigen by MALDI TOF mass spectrometry. BDCA-4 is identical to neuropilin-1. He et al. (1997).

EXAMPLE 12

Ligation of BDCA-2 with Anti-BDCA-2 Monoclonal Antibody (AC144) Induces Intracellular Ca$^{2+}$ Mobilization, whereas Ligation of BDCA-4 (neuropilin-1) with Anti-BDCA-4 does not Induce Ca$^{2+}$ Mobilization Materials and Methods:
Measurement of cytosolic calcium in BDCA-2$^+$ BDCA-4$^+$ BDC and BDCA-2-transfected or non-transfected U937 cells. BDCA-2$^+$ BDCA-4$^+$ blood DC and BDCA-2-transfected or non-transfected U937 cells were loaded with Indo-1 AM (Sigma, St. Louis, Mo.) as described by Valitutti et al. (1993) Eur. J. Immunol. 23:790-795. Anti-BDCA-2 (AC144, IgG1) or anti-BDCA-4 (AD5-17F6, IgG1) mAb were added to freshly isolated BDCA-2$^+$BDCA-4$^+$ BDC and BDCA-2-transfected or non-transfected U937 cells, respectively, followed or not followed by rat anti-mouse IgG1 mAb (X56) as cross-linker. Cells were analyzed on a flow cytofluorimeter to detect Ca$^{2+}$ fluxes. Only live (based on scatter criteria) and Indo-1-labeled cells (based on 405 nm versus 525 nm emission spectra) were included in the analysis.

FIG. 13 shows intracellular mobilization is induced in immunomagnetically purified BDCA-2$^+$BDCA-4$^+$ BDC (A, B) and BDCA-2-transfected U937 cells (D), but not in non-transfected U937 cells (E) via anti-BDCA-2 mAb alone (A) and or anti-BDCA-2 plus crosslinking secondary mAb (B, D, E).

Ligation of BDCA-4 on immunomagnetically purified BDCA-2$^+$BDCA-4$^+$ BDC with anti-BDCA4 mAb and cross-linking secondary mAb does not induce cytosolic Ca$^{2+}$-mobilization. Shown is the Ca$^{2+}$-dependent 405 nm/525 nm ratio of Indo-1-fluorescence (Y-axis) against time (X-axis, a value of 1024 corresponds to 204,80 sec).

As shown in FIG. 13, ligation of surface BDCA-2 on plasmacytoid BDC (FIG. 13A and B) and BDCA-2-transfected U937 cells (FIG. 13D) with a specific mAb (AC144, IgG1) followed (FIG. 13B and D) or not followed (FIG. 13A) by a secondary cross-linking mAb (rat anti-mouse IgG1, X56) elicited a rapid and transient rise in cytosolic calcium concentration. On the contrary, incubation of plasmacytoid DC with anti-BDCA-4 mAb (AD5-17F6) followed by a secondary cross-linking mAb (rat anti-mouse IgG1, X56) (FIG. 14C), or of non-transfected U937 cells with anti-BDCA-2 mAb (AC144, IgG1) followed by a secondary cross-linking mAb (rat anti-mouse IgG1, X56) (FIG. 13E) did not induce a rapid and transient rise in cytosolic calcium concentration.

EXAMPLE 13

Production of Type I Interferon by Purified BDCA-2$^+$ BDCA-4$^+$ BDC in Response to Viral Stimulation (Influenza Virus Strain PR8) is Inhibited by Triggering of BDCA-2 with Anti-BDCA-2 mAb CD4$^+$CD123$^{bright}$CD11c$^-$ plasmacytoid DC were shown to be the chief type I interferon producers in response to enveloped viruses, bacteria, and tumor cells. Fitgerald-Bocarsly et al. (1993) Pharmacol. Ther. 60:39-62; Siegal et al. (1999) Science 284:1835-1837; Cella et al. (1999) Nature Med. 5:919-923. For this reason, they have also been called natural type I interferon producing cells (NIPC). Plasmacytoid DC express BDCA-2 and BDCA-4. As shown in FIG. 14, ligation of surface BDCA-2 on plasmacytoid DC with a specific mAb followed by a secondary cross-linking mAb (rat anti-mouse IgG1, X56), inhibits secretion of type I interferon by immunomagnetically purified plasmacytoid BDCA-2$^+$ BDCA-4$^+$ DC from blood or tonsils in response to stimulation with influenza virus strain PR8 (5 HAU/ml). The level of type I interferon production in cultures with anti-BDCA-2, influenza virus and cross-linking mAb (FIG. 14, AC144+RamG1+ FLU) is much lower as in cultures with influenza virus alone (FIG. 14, FLU), or with an isotype control mAb (anti-cytokeratin mAb CK3-11D5, IgG1), influenza virus and cross-linking mAb (FIG. 14, CK3+RamG1+FLU).

Conversely, ligation of surface BDCA-4 on plasmacytoid DC with a specific mAb followed by a secondary cross-linking mAb (rat anti-mouse IgG1, X56), does not inhibit secretion of type I interferon by immunomagnetically purified plasmacytoid BDCA-2$^+$BDCA-4$^+$ DC from blood or tonsils in response to stimulation with influenza virus strain PR8 (5 HAU/ml). The level of type I interferon production in cultures with anti-BDCA-4, influenza virus and cross-linking mAb (FIG. 14, 17F6+RamG1+FLU) is the same as in cultures with an isotype control mAb (anti-cytokeratin mAb CK3-11D5, IgG1), influenza virus and cross-linking mAb (FIG. 14,. CK3+RamG1+FLU).

Materials and Methods:
BDCA-2- and BDCA-4-expressing plasmacytoid DC were isolated from PBMC (FIG. 14A) or tonsillar cells (FIG. 14B) by direct magnetic labeling with anti-BDCA-4 (AD5-17F6)-conjugated microbeads and enrichment of labeled cells by magnetic cell separation using MACS® (Miltenyi Biotec). Isolated BDCA-2- and BDCA-4-expressing plasmacytoid DC were cultured for 24 hours in medium in the presence of: a) IL-3 alone (FIG. 14, Control); b) IL-3, anti-BDCA-2 mAb (AC144, IgG1) and rat anti-mouse IgG1 mAb (FIG. 14, AC144+RamG1); c) IL-3, anti-BDCA-2 mAb (AC144, IgG1), rat anti-mouse IgG1 mAb, and influenza virus strain PR8 (FIG. 14, AC144+RamG1+FLU); d) IL-3 and influenza virus strain PR8 (FIG. 14, FLU); e) IL-3, anti-cytokeratin mAb (CK3-11D5, IgG1), rat anti-mouse IgG1 mAb, and influenza virus strain PR8 (FIG. 14, CK3+RamG1+FLU); and f) IL-3, anti-BDCA-4 mAb (AD5-17F6), rat anti-mouse IgG1 mAb, and influenza virus strain PR8 (FIG. 14 17F6+RamG1+FLU).

Secreted type I interferon in the culture supernatants was measured by evaluating inhibition of Daudi cell proliferation (Nederman et al. (1990) Biologicals 18:29-34) with reference to a standard IFN-α curve.

Regarding the inhibition of type I interferon production by BDCA-2$^+$BDCA-4$^+$ plasmacytoid DC, increased levels of circulating type I interferon and of type I interferon inducing factor (something like a complex of anti-DNA antibody and DNA) are found in SLE patients and correlate to disease activity. Furthermore, patients with non-autoimmune disorders treated with type I interferon frequently develop autoantibodies and occasionally SLE. Several papers from Ronnblom et al. (1999) Clin. Exp. Immunol. 115: 196-202; (1999) J. Immunol. 163: 6306-6313; and (2000) J. Immunol. 165: 3519-3526) show that type I interferon inducing factors derived from patients induce secretion of type I interferon in PBMC from healthy donors and they selectively activate natural type I interferon producing cells (NIPC=plasmacytoid DC).

The findings presented herein that ligation of BDCA-2 suppresses the production of type I interferon induced by viral stimulation show that binding to BDCA-2 can be applied to treat the disease not just by ligation of BDCA-2 but also by depleting NIPC (=BDCA-2+ BDCA-4+ plasmacytoid DC). The invention thus further encompasses in vivo, in vitro and ex vivo depletion of NIPC. Such depletion is suitable for use in treatment or prophylaxis of autoimmune diseases.

FIG. 14 shows ligation of BDCA-2 but not of BDCA-4 with a specific mAb followed by a secondary cross-linking mAb inhibits secretion of type I interferon by plasmiacytoid BDCA-2$^+$BDCA-4$^+$ DC from blood or tonsils in response to stimulation with influenza virus strain PR8. Plasmacytoid BDCA-2$^+$BDCA-4$^+$ DC from blood (A) or tonsils (B) were cultured for 24 hours in the presence of IL-3 alone (control); IL-3, anti-BDCA-2 mAb and rat anti-mouse IgG1 mAb (AC144+RamG1); IL-3, anti-BDCA-2 mAb, rat anti-mouse IgG1 mAb, and influenza virus strain PR8 (AC144+RamG1+FLU); IL-3 and influenza virus strain PR8 (FLU); IL-3, anti-cytokeratin mAb, rat anti-mouse IgG1 mAb, and influenza virus strain PR8 (CK3+RamG1+FLU); IL-3, anti-BDCA-4 mAb, rat anti-mouse IgG1 mAb, and influenza virus strain PR8 (17F6+RamG1+FLU). Secreted type I interferon (U/ml) in the culture supernatants was measured by a bioassay with reference to a standard type I interferon curve.

EXAMPLE 14

BDCA-2 is not Only Able to Endocytose a Ligand, but also to Deliver it to an Antigen-processing and Loading Compartment, and to Present it to CD$^{4+}$ Class II-restricted T Cells Materials and Methods:
BDCA-2- and BDCA-4-expressing plasmacytoid DC were isolated from PBMC by direct magnetic labeling with anti-BDCA-4 (AD5-17F6)-conjugated microbeads and enrichment of labeled cells by magnetic cell separation using MACS® (Miltenyi Biotec). Isolated BDCA-2- and BDCA-4-expressing plasmacytoid DC were co-cultured with $4 \times 10^4$ cells/well of the B13 T cell clone (Lanzavecchia et al. (1988) J. Exp. Med. 167:345-352) in 96-well flat-bottom microplates in the presence of IgG1 mAbs (0.2 µg/ml). mAbs used in the assay were the following: AC144 (anti-BDCA-2, IgG1), ZM3.8.(anti-ILT3, IgG1) and CK3-11D5 (anti-cytokeratin, IgG1). After 48 hours, the cultures were pulsed with ($^3$H)thymidine (1 µCi/well), and the radioactivity incorporated was measured after additional 16 hours. (3H)Thymidine uptake (cpm) was plotted against the number of isolated BDCA-2- and BDCA-4-expressing plasmacytoid DC in the cultures (FIG. 15).

FIG. 15 shows presentation of anti-BDCA-2 mAb (AC144, IgG1) to a T cell clone specific for mouse IgG1 by isolated BDCA-2- and BDCA-4-expressing plasmacytoid DC. BDCA-2$^+$BDCA-4$^+$ plasmacytoid DC present anti-BDCA-2 mAb (AC144, IgG1, ■) to T cells much more efficiently than anti-ILT-3 mAb (ZM3.8, IgG1, ▲) and anti-cytokeratin mAb (CK3-11D5, IgG1, ●).

Incubation of anti-BDCA-2 mAb (AC144, IgG1)-labeled BDCA-2$^+$BDCA-4$^+$ plasmacytoid DC at 37° C. results in extremely rapid internalization of the anti-BDCA-2 mAb/BDCA-2 complexes on the cell surface (see FIG. 8). Here, it is shown that the anti-BDCA-2 mAb (AC144, IgG1) accesses an antigen-processing and loading compartment and peptides derived from the antibody are efficiently presented to a CD4$^+$ class II-restricted T cell clone (B13) specific for a mouse IgG1 peptide epitope. The presentation of the anti-BDCA-2 mAb was compared to that of an IgG1 mAb that binds to a receptor (ILT3) known to be capable of targeting its ligand(s) into processing and peptide-loading compartments, and to that of an IgG1 mAb that does not bind to a cell-surface molecule on BDCA-2$^+$BDCA-4$^+$ plasmacytoid DC (anti-cytokeratin mAb CK3-11D5, IgG1), but can be taken up in the fluid phase. As shown in FIG. 15, BDCA-2$^+$BDCA-4$^+$ plasmacytoid DC presented anti-BDCA-2 mAb (AC144) to T cells much more efficiently than the anti-ILT-3 mAb and the anti-cytokeratin mAb.

EXAMPLE 15

Figure 16:
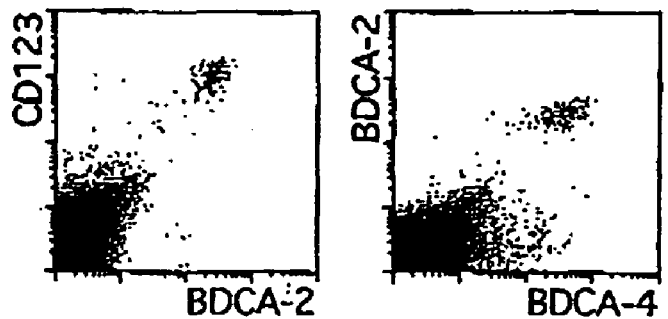
FIG. 16 shows expression of BDCA-2 and BDCA-4 on tonsillar plasmacytoid CD123+ DC.

In Tonsillar Cells, Expression of BDCA-2 is Restricted to CD123$^+$ T Cell-zone Associated Plasmacytoid DC, whereas BDCA-4 may also be Expressed at Low Levels on a Few Other Cells FIG. 16 shows expression of BDCA-2 and BDCA-4 on tonsillar plasmacytoid CD123$^+$ DC. Shown are two-color stainings of tonsillar cells with a FITC-conjugated mAb against BDCA-2 (AC144) and a PE-conjugated mAb against CD123 and BDCA-4 (AD5-17F6), respectively. Note that expression of BDCA-2 is restricted to CD123bright plasmacytoid DC, whereas BDCA-4 is also expressed at low levels on a few other cells.

EXAMPLE 16

BDCA-4 mAb (AD5-17F6) Recognizes Neuropilin-1

Neuropilin-1 is a receptor for the collapsin/semaphorin family that mediates neuronal cell guidance. Neuropilin-1 is also expressed by endothelial and tumor cells as an isoform-specific receptor for vascular endothelial growth factor. However, it was not known before, that neuropilin-1 is expressed on plasmacytoid DC in blood and tonsils and that it represents an excellent marker for plasmacytoid DC at least in fresh non-cultured blood.

Material and Methods:

Neuropilin-1 was immunoprecipitated from cell lysates of non-transfected PAE cells (P) and neuropilin-1-transfected PEA cells (NP) (Soker et al. (1998) Cell 92:735-745) using the anti-BDCA-4 mAb AD5-17F6 (anti-NRP-1 (ML)). Precipitated proteins were analyzed by SDS-PAGE and Western blotting with the BDCA-4-specific mAb AD5-17F6 (ML) or a neuropilin-1-specific mAb from Shay Soker, Children's Hospital, Boston, Mass. (S).

Figure 17:
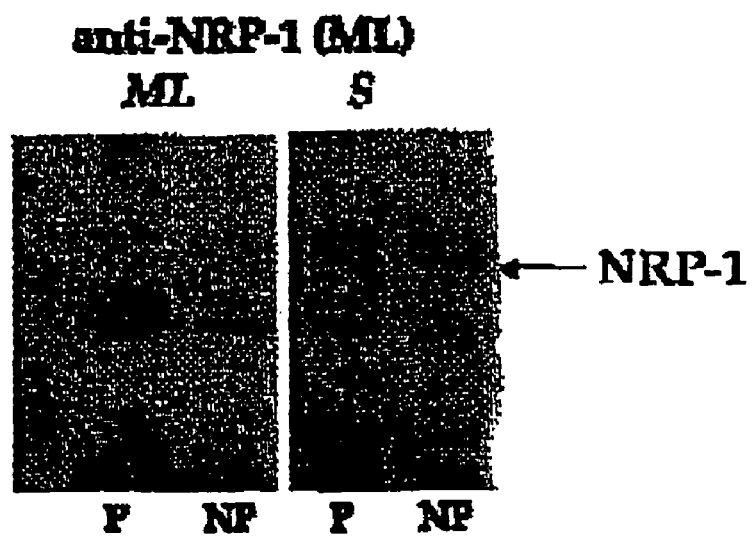
FIG. 17 shows that neuropilin-1 (GenBank Accession No. 003873) is immunoprecipitated from cell lysates of neuropilin-1-transfected PEA cells (NP), but not of non-transfected PAE cells (P) with the anti-BDCA-4 mAb AD5-17F6 (anti-NRP-1 (ML)). Precipitated proteins were analyzed by SDS-PAGE and Western blotting with the BDCA-4-specific mAb AD5-17F6 (ML) or an neuropilin-1-specific mAb from Shay Soker, Children's Hospital, Boston, Mass. (S).

FIG. 17 shows that neuropilin-1 was immunoprecipitated from cell lysates of neuropilin-1-transfected PEA cells (NP) but not of non-transfected PAE cells (P) with the anti-BDCA-4 mAb AD5-17F6 (anti-NRP-1 (ML)). Precipitated proteins were analyzed by SDS-PAGE and Western blotting with the BDCA-4-specific-mAb AD5-17F6 (ML) or a neuropilin-1-specific mAb from Shay Soker, Children's Hospital, Boston, Mass. (S).

Note that the BDCA-4-specific mAb AD5-17F6 immunoprecipitates a specific band of about 130-140 kDa from neuropilin-1-transfected PEA cells (NP), but not from non-transfected PAE cells (P). The band can be detected with the neuropilin-1-specific mAb from Shay Soker (S) but not with the anti-BDCA-4 mAb AD5-17F6 (ML). Thus, our anti-BDCA-4 mAb AD5-17F6 recognizes the native form of neuropilin-1 in standard immunoprecipitation experiments, but fails to detect the denatured form of neuropilin-1 when used in SDS-PAGE/Western blotting experiments.

Interestingly, neuropilin-1 is also-expressed by endothelial and tumor cells as an isoform-specific receptor for vascular endothelial growth factor (VEGF). More interestingly, several papers (Gabrilovich et al. (1996) Nature Med. 2:1267; Nature Med. 2: 1096-103; Gabrilovich et al. (1999) Clin. Cancer Res. 5: 2963-70; Ohm et al. (1999). J. Immunol. 163: 3260-8; Oyama et al. (1998) J. Immunol. 160:1224-32; Gabrilovich et al. (1998). Blood 92:4150-66; Ishida et al. (1998) J. Immunol. 161:4842-51) have shown that VEGF produced by a large percentage of tumors decreases DC generation and function in vivo. It is not clear whether these effects on DCs are mediated by neuropilin-1 (BDCA-4), but the invention encompasses neuropilin-1-mediated functional modulation of DCs.

EXAMPLE 17

Production of Type I Interferon (IFN-α) by Purified BDCA-2$^+$BDCA-4$^+$ BDC in Response to Stimulation with Poly I:C is Inhibited by Triggering of BDCA-2 with Anti-BDCA-2 mAb CD4$^+$CD123$^{bright}$CD11c$^-$ plasmacytoid DC were shown to be the chief type I interferon producers in response to enveloped viruses, bacteria, and tumor cells. Fitzgerald-Bocarsly et al. (1993) Pharmacol. Ther. 60:39-62; Siegal et al. (1999) Science 284: 1835-1837; Cella et al. (1999) Nature Med. 5:919-923. For this reason, they have also been called natural type I interferon producing cells (NIPC). Plasmacytoid DC express BDCA-2 and BDCA-4. As shown in FIG. 19, ligation of surface BDCA-2 on plasmacytoid DC with a specific mAb followed by a secondary cross-linking mAb (goat anti-mouse IgG), inhibits secretion of IFN-α by immunomagnetically purified plasmacytoid BDCA-2$^+$BDCA-4$^+$ DC from blood or tonsils in response to stimulation with poly I:C. The level of IFN-α production in cultures with anti-BDCA-2, poly I:C and cross-linking mAb (FIG. 18, AC144+Goat anti-mouse IgG+Poly I:C) is lower as in cultures with mouse IgG1, poly I:C and cross-linking mAb (FIG. 18, Mouse IgG1+Goat anti-mouse IgG+Poly I:C).

Materials and Methods:

CD11c$^-$CD123$^{bright}$ plasmacytoid DC were separated from human peripheral blood mononuclear cells using BDCA-4 microbeads. CD11c$^-$C$_{123}^{bright}$ plasmacytoid DC (1×10$^6$ cells/ml) were incubated with 10 μg/ml of AC144 mAb or mouse IgG1 mAb (CF6B, anti-TPO) in RPMI, 10% FCS, 110 mM HEPES, 50 μM 2-ME, 20 μg/ml gentamicin at 37° C. for 30 min. 20 μg/ml of goat anti-mouse IgG (Chemicon International) were added and cells were again incubated at 37° C. for 30 min. These cells were cultured with or without 20 kg of poly I:C (Sigma) at 37° C. for 24 hours. Culture supernatants were harvested and IFN-α concentrations were determined by ELISA (Endogen). The sensitivity of the assay is 3 μg/ml.

Figure 18:
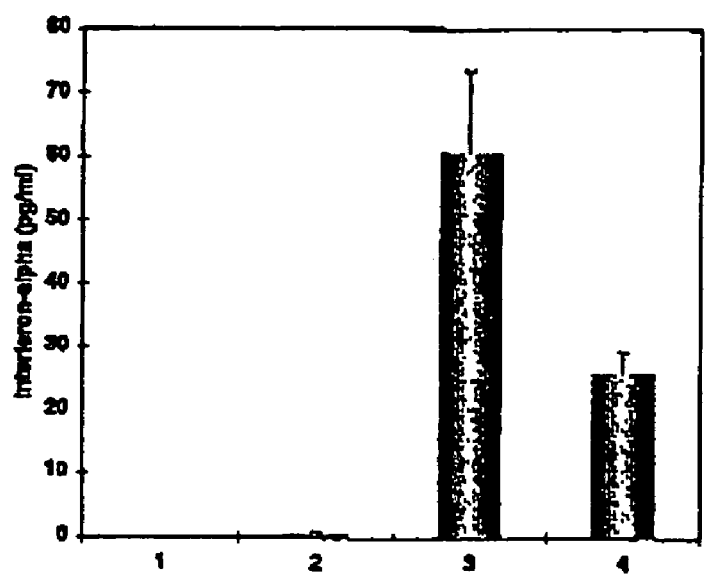
FIG. 18 shows ligation of BDCA-2 but not of BDCA-4 with a specific mAb followed by a secondary cross-linking mAb inhibits secretion of INF-α by plasmacytoid BDCA-2+ BDCA-4+ DC from blood or tonsils in response to stimulation with poly I:C. Plasmacytoid BDCA-2+ BDCA-4+ DC from blood were cultured with 10 μg/ml of AC144 mAb (2 and 4) or mouse IgG1 mAb (CF6B, anti-TPO, 1 and 3) at 37° C. for 30 min.
Figure 19:
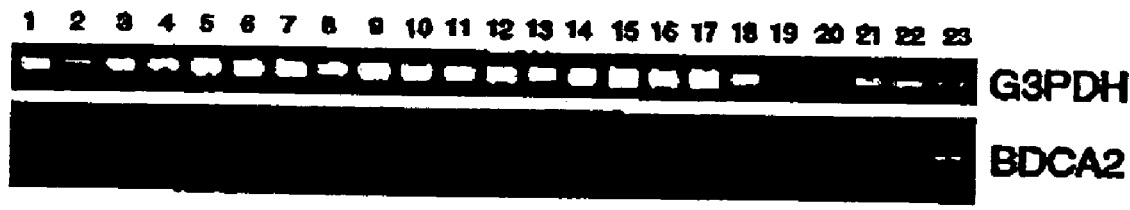
FIG. 19 shows an analysis of human multiple tissue cDNA panels from CLONTECH (lane 1: heart; lane 2: brain; lane 3: placenta; lane 4: lung; lane 5: liver; lane 6: skeletal muscle; lane 7: kidney; lane 8: pancreas; lane 9: spleen; lane 10: thymus; lane 11: testis; lane 12: ovary; lane 13: small intestine; lane 14: lymph node; lane 15: bone marrow; lane 16: fetal liver; lane 17: tonsil) and an analysis of cDNAs prepared from different populations of blood leukocytes (lane 18: T cells; lane 19: B cells; lane 20: NK cells; lane 21: monocytes; lane 22: CD11c$^{bright}$CD123$^{low}$BDC; lane23: CD11c-CD123 plasmacytoid DC) for BDCA-2 cDNA. The control is G3PDH.

FIG. 18 shows ligation of BDCA-2 but not of BDCA-4 with a specific mAb followed by a secondary cross-linking mAb inhibits secretion of IFN-α by plasmacytoid BDCA-2$^+$ BDCA-4$^+$ DC from blood or tonsils in response to stimulation with poly I:C. Plasmacytoid BDCA-2+ BDCA-4+ DC from blood were cultured with 10 μg/ml of AC144 mAb (2 and 4) or mouse IgG1 mAb (CF6B, anti-TPO, 1 and 3) at 37° C. for 30 min. 20 μg/ml of goat anti-mouse IgG were added and the cells were again incubated at 37° C. for 30 min. These cells were cultured with (3 and 4) or without (1 and 2) 20 μg of poly I:C at 37° C. for 24 hours. Culture supernatants were harvested and IFN-α concentrations were determined by ELISA.

EXAMPLE 18

BDCA-2 mRNA Expression Analysis by RT-PCR in Various Tissues and Purified Blood Cell Populations Nucleic and Amino Acid Sequences The cDNA encoding BDCA-2 was obtained by expression cloning in COS cells. FIG. 5 shows the amino acid sequence of BDCA-2 (the isoform with all six exons expressed). BDCA-2 is a novel C-type lectin type II membrane protein. Such lectins are described, for instance in Bates et al. (1999) J. Immunol. 163:1973-1983. Comparison of BDCA-2 to known C-type lectins is shown in Example 20.

FIG. 19 shows on analysis of human multiple-tissue cDNA panels from Clonetech (lane 1: heart; lane 2: brain; lane 3: placenta; lane 4: lung; lane 5: liver; lane 6: skeletal muscle; lane 7: kidney; lane 8: pancreas; lane 9: spleen; lane 10: thymus; lane 11: testis; lane 12: ovary; lane 13: small intestine; lane 14: lymph node; lane 15: bone marrow; lane 16: fetal liver; lane 17: tonsil) and on analysis of cDNAs prepared from different populations of blood leukocytes (lane 18: T cells; lane 19: B cells; lane 20: NK cells; lane 21: monocytes;

lane 22: CD11c^bright CD123^low DC; lane23: CD11c-CD123^bright plasmacytoid BDC) for the presence of BDCA-2 cDNA.

All cDNAs were normalized to the mRNA expression level of several different housekeeping genes (glyceraldehyde-3-phosphate dehydrogenase, phospholipase A2, α-tubulin, and β-actin). Normalization ensures an accurate assessment of tissue specificity and relative abundance of target mRNAs. The same amount of cDNA (about 50 µg) was used for each RT-PCR reaction. RT-PCR reactions were performed with specific primers for BDCA-2 (forward: 5'-TTGAAAGAAC-CACACCCCGAAAGT (SEQ ID NO:7) and reverse: 5'-TAGCTTTCTACAACGGTGGATGCC (SEQ ID NO:8)) and primers for the four housekeeping genes (CLONTECH) mentioned above using AdvanTaq Plus DNA Polymerase (CLONTECH).

Cycle conditions were as follows: 94° C. for 30 sec and 68° C. for 2 min. 34 cycles were used for BDCA-2 and 38 cycles for glyceraldehyde-3-phosphate dehydrogenase (G3PDH). Note that BDCA-2 mRNA signals are only detected in CD11c^-CD123^bright plasmacytoid DC. If four more PCR cycles were used for amplification of BDCA-2 cDNA (38 cycles instead of 34 cycles), weak signals were also detected in pancreas, testis, ovary, bone marrow and tonsil. With cDNA from testis (38 PCR cycles), signals of shorter transcripts (splice variants) were more prominent as compared to the signals from CD11c^-CD123^bright and signals from the full-length transcript were actually only detectable with even more PCR cycles.

EXAMPLE 19

Exon/Intron Structure of BDCA-2 and Splice Variants of BDCA-2

Figure 20:
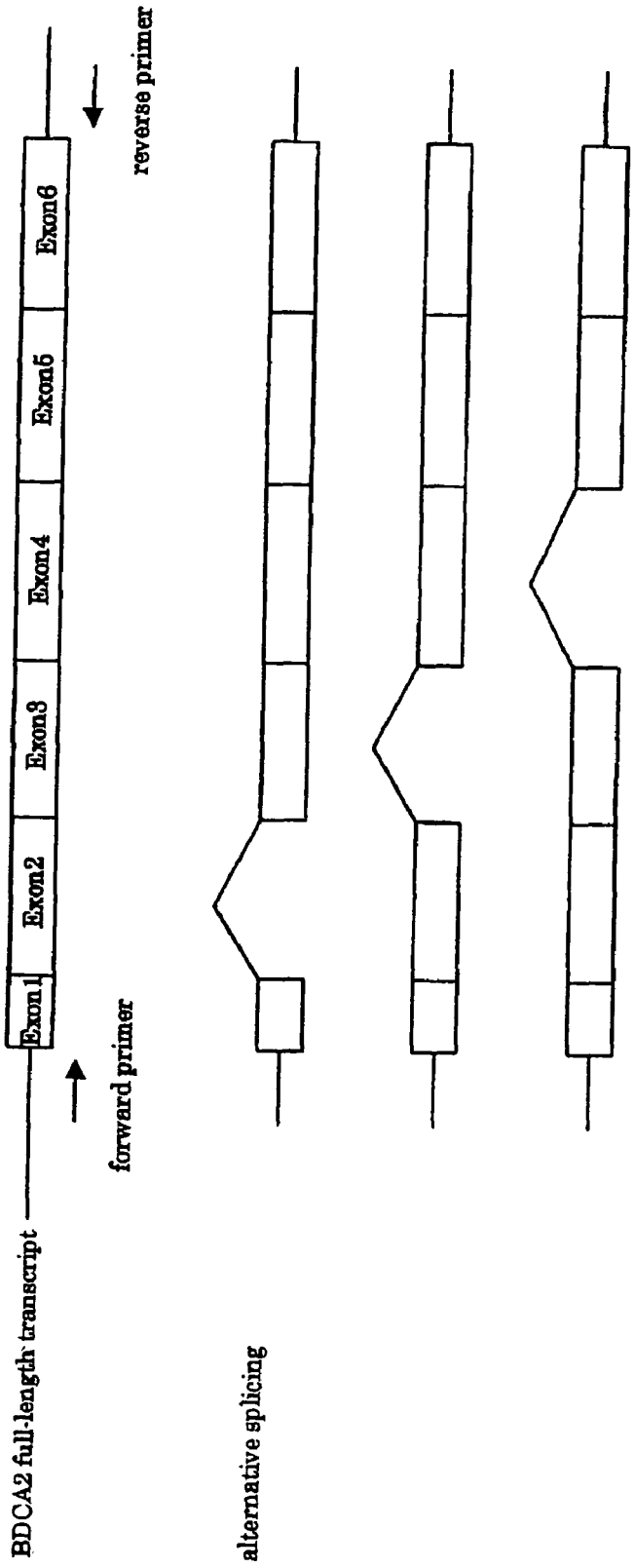
FIG. 20 shows the splice variants of the BDCA-2 transcript. Splice variants were analyzed by RT-PCR using the specific primers for BDCA-2 used in expression analysis. The amplified fragments were cloned to plasmid vectors and sequenced.
Figure 21:
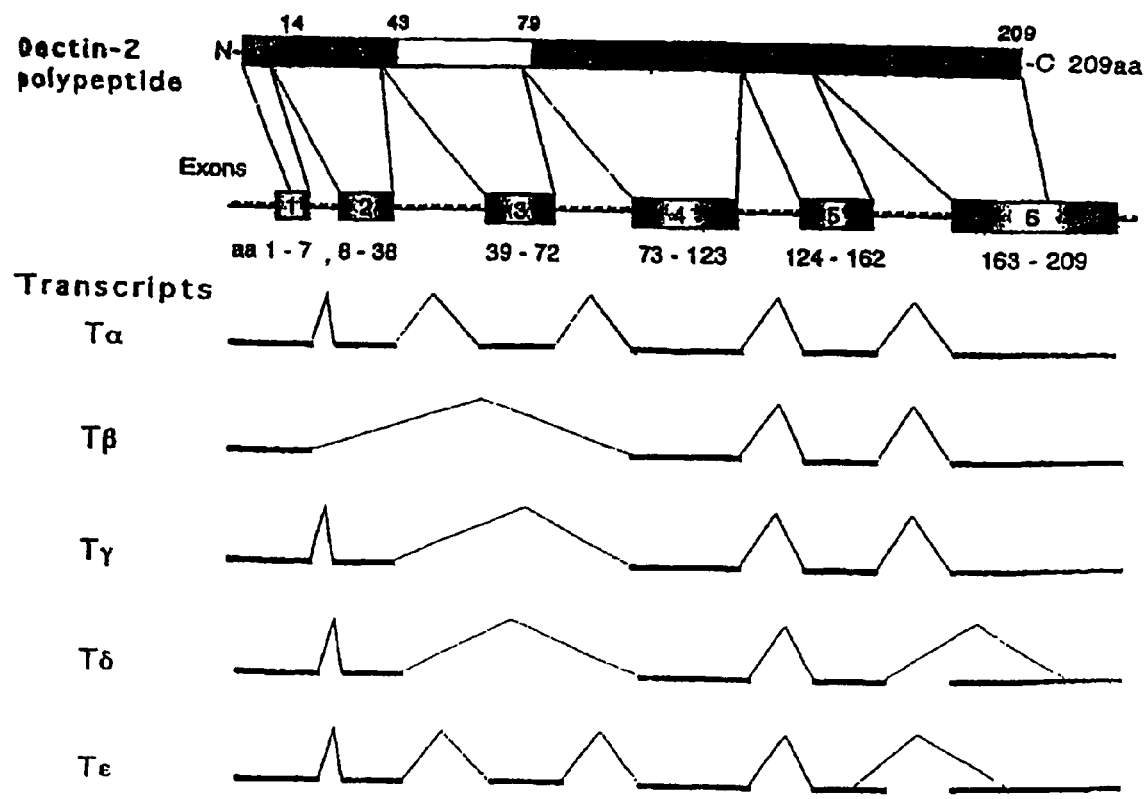
FIG. 21 shows the splice variants of Dectin-2 transcripts.

The information on the splice variants of BDCA-2 was obtained by RT-PCR amplification of mRNA from plasmacytoid DC with primers complementary to mRNA sequences in front of the start codon (forward primer: 5'-TTGAAA-GAACCACACCCCGAAAGT (SEQ ID NO:7)) and behind the stop codon (reverse primer: 5'-TAGCTTTCTACAACG-GTGGATGCC(SEQ ID NO:8)), cloning of the resulting fragments in plasmids and sequencing of the inserts. The results are shown in FIG. 20. For comparison, splice variants of mouse dendritic cell-associated C-type lectin 2 (Dectin-2) are shown in FIG. 21.

FIG. 22 shows an alignment of the mRNA sequences of BDCA-2 and mouse Dectin-2 with the positions of the deduced introns being indicated. Table 3 shows the parameters of the exons.

TABLE 3

| Exon | mRNA | amino acid residues encoded | Number of amino acid residues encoded |
|---|---|---|---|
| 0 | 0-361 | | 0 |
| 1 | 362-522 | 1-10 | 10 |
| 2 | 523-615 | 11-41 | 31 |
| 3 | 616-726 | 42-78 | 37 |
| 4 | 727-872 | 78-127 | 49 |
| 5 | 873-988 | 128-166 | 39 |
| 6 | 989-1283 | 167-213 | 47 |

The positions of the introns are based on Homo sapiens Chromosome 12 Clone RP11-277J24, Working Draft Sequence, 21 unordered pieces (GenBank Accession Number AC006517) and the rules for splicing of transcripts. The intron/exon makeup BDCA-2 is similar to that of Dectin-2.

At least four splice variants of BDCA-2 are produced. These are an mRNA encoding a protein with all six exons; an mRNA encoding a protein containing exons 1, 3, 4, 5, and 6; an mRNA encoding a protein containing exons 1, 2, 4, 5, and 6 and an mRNA encoding a protein containing exons 1, 2, 3, 5, and 6.

EXAMPLE 20

BDCA-2 Homology and Protein Domains

An alignment of the amino acid sequences of human BDCA-2, human DCIR (dendritic cell immunoreceptor), and mouse Dectin-2 (dendritic cell-associated C-type lectin-2) is shown in FIG. 23.

Human DCIR (GenBank Accession Number AJ133532) is the molecule with the highest homology to BDCA-2 among human molecules (see Bates et al. (1999) J. Immunol. 163: 1973) with about 51% of the aa being identical over a stretch of 191 aa.

Mouse Dectin-2 (GenBank Accession Number AF240357) is most likely the murine homolog of human BDCA-2 (see Ariizumi et al. (2000) J. Biol. Chem. 16:11957; WO 98/28332; PCT/US97/23761; and U.S. Pat. No. 6,046,158) with about 51% of the aa being identical over a stretch of 211 aa.

BDCA-2 (213 aa), DCIR (237 aa) and Dectin-2 (209 aa) are all type II membrane glycoproteins of the calcium-dependent (C-type) lectin family. Each of the molecules contains a putative cytoplasmic domain (BDCA-2: aa 1-21; DCIR: aa 1-44; Dectin-2: aa 1-17), a putative transmembrane domain (BDCA-2: aa 22-41; DCIR: 44-69; Dectin-2: 18-40), and a putative extracellular domain (BDCA-2: aa 42-213; DCIR: 70-237; Dectin-2: 40-209). Within the putative extracellular domain, each of the molecules contains a single carbohydrate recognition domain (CRD) at the COOH-terminal end (BDCA-2: aa 83-206; DCIR: 106-230; Dectin-2: 79-202). FIG. 23 shows the alignment of human BDCA-2, human DCIR and mouse Dectin-2.

Putative protein domains/motifs as found using the PROSITE database are shown in Table 4.

TABLE 4

| Domain | BDCA-2 |
|---|---|
| ASN glycosylation | 110-113 NCSV (SEQ ID NO: 9) |
| | 137-140 NSSY (SEQ ID NO: 10) |
| | 164-167 NVTF (SEQ ID NO: 11) |
| cAMP- and cGMP-dependent protein kinase phosphorylation site | 53-56 KRLS (SEQ ID NO: 14) |
| | 135-138 SQK |
| Protein Kinase C phosphorylation site | 51-53 TVK |
| | 107-109 SQK |
| Casein kinase II phosphorylation site | 123-126 TREE (SEQ ID NO: 16) |
| | 187-190 SSEE (SEQ ID NQ: 17) |
| Tyrosine kinase phosphorylation site | 57-64 KLREYQQY (SEQ ID NO: 30) |
| Amidation site | 148-151 GGRR (SEQ ID NO: 32) |
| N-myristylation site | |
| C-type lectin domain signature | 180-206 |
| | Dectin-2 |
| ASN glycosylation | 131-134 NESL (SEQ ID NO: 12) |
| cAMP- and cGMP-dependent protein kinase phosphorylation site | |

TABLE 4-continued

| Domain | |
|---|---|
| Protein Kinase C phosphorylation site | 15-17 TLR |
| | 49-51 SRR |
| | 72-74 SEK |
| | 94-96 STK |
| Casein kinase II phosphorylation site | 94-97 STKE (SEQ ID NO: 18) |
| | 101-104 STSE (SEQ ID NO: 19) |
| | 119-122 TEAE (SEQ ID NO: 20) |
| | 200-203 SICE (SEQ ID NO: 21) |
| Tyrosine kinase phosphorylation site | 50-58 RRLYELHTY |
| | (SEQ ID NO: 31) |
| Amidation site | |
| N-myristylation site | 11-16 GVCWTL |
| | (SEQ ID NO: 33) |
| | 68-73 GTMVSE (SEQ ID NO: 34) |
| | 77-82 GCCPNH 9SEQ |
| | ID NO: 35) |
| C-type lectin domain signature | 11-17 176-202 |
| | DCIR |
| ASN glycosylation | 185-188 NESS (SEQ ID NO: 13) |
| CamP- and cGMP-dependent protein kinase phosphorylation site | 78-81 KKTT (SEQ ID NO: 15) |
| Protein Kinase C phosphorylation site | 80-82 TTK |
| | 130-132 SEK |
| | 211-213 SPK |
| Casein kinase II phosphorylation site | 1-9 TYAE (SEQ ID NO: 22) |
| | 80-83 TTKE (SEQ ID NO: 23) |
| | 87-90 TTLE (SEQ ID NO: 24) |
| | 126-129 SWQD (SEQ ID NO: 25) |
| | 130-133 SEKD (SEQ ID NO: 26) |
| | 146-149 TQEE (SEQ ID NO: 27) |
| | 168-171 SDPE (SEQ ID NO: 28) |
| | 228-231 SVCE (SEQ ID NO: 29) |
| Tyrosine kinase phosphorylation site | |
| Amidation site | |
| N-myristylation site | 20-25 GINTAS (SEQ ID NO: 36) |
| C-type lectin domain signature | 203-230 |

BDCA-2 contains three putative N-glycosylation sites (aa 110-113 NCSV; aa 137-140 NSSY; aa 164-167 NVTF), whereas Dectin-2 (aa 131-134 NESL) and DCIR (aa 185-188-NESS) contain only one putative N-glycosylation site. All the putative phosphorylation sites of BDCA-2 and Dectin-2 are located in the putative extracellular domain. Thus, it is rather unlikely that they become phosphorylated by intracellular kinases. Like many C-type lectins (e.g. CD94, Ly-49, and NKG2) that are encoded in the natural killer gene complex, DCIR contains the consensus immunoreceptor tyrosine-based inhibitory motif (ITIM motif; (I/V)XYXX(L/V) (SEQ ID NO:37)) in the cytoplasmic domain (aa 5-10 ITYAEV (SEQ ID NO:38)). Interestingly, this ITIM motif is not found in the relatively short cytoplasmic tail of BDCA-2 and Dectin-2 (BDCA-2: 21 aa; Dectin-2: 17 aa).

EXAMPLE 21

BDCA-3 Protein Analysis

BDCA-3-7expressing HD-MY-Z cells were stimulated for 24 hours with 10 ng/ml PMA (Sigma) and 0.5 mg/ml Ionomycin to up-regulate BDCA-3-expression. $3 \times 10^7$ PMA/Ionomycin stimulated HD-MY-Z cells were surface biotinylated by incubation for 15 minutes at 4° C. with 1 mg/ml Sulfo-NHS-LC-Biotin (Pierce), and washed twice. Cells were resuspended in 50 mM Tris-HCl pH 8.0 supplemented with 10% sucrose and proteinase inhibitors (Phenylmethyl-sulfonylfluoride, Pepstatin A, Leupeptin, and Aprotinin from Serva) and at 0° C. ultrasonified (5×4 seconds, 70% output). Sonified cells were centrifuged at 900×g at 4° C. for 10 minutes to remove nuclei and intact cells. The supernatant was centrifuged at 30,000×g at 4° C. for 2 hours to obtain purified cell membranes. Membranes were lysed by incubation in 50 mM Tris-HCl pH 8.0, 150 mM NaCl supplemented with proteinase inhibitors and 1% NP-40 for 1 hour at 0° C. Non-solubilized membrane fragments were removed by centrifugation at 30,000×g at 4° C. To the supernatant, $MnCl_2$ and $CaCl_2$ were added to a final concentration of 1 mM each. The lysate was adsorbed onto a ConA Sepharose column (1 ml), and bound proteins were eluted with 10 ml elution buffer (0.5 M D(+) Mannose, 20 mM Tris-HCl pH 7.4, 0.5 M NaCl, 1% NP-40) and concentrated to a volume of 1 ml using Cetriprep-10 centrifugal concentrators (Amicon).

The proteins were pre-cleared by incubation with 150 μl anti-NIP mAb-conjugated MicroBeads (Miltenyi Biotec) for 30 minutes at 4° C. and magnetic cell separation column separation. For specific immunoprecipitation of BDCA-3, proteins were either incubated with 2 μg of the NIP-conjugated BDCA-3-specific mAb AD5-14H12 (IgG1) or for control of specificity with 2 μg of the NIP-conjugated CD19-specific mAb SJ25-C1 (IgG1) as primary reagent for 14 hours at 4° C., and with anti-NIP mAb-conjugated MicroBeads as secondary reagent for 3 hours at 4° C. Precipitated proteins were isolated by column separation. Retained proteins were eluted with 70 μl SDS-PAGE buffer containing DTT. Precipitated proteins were analyzed by SDS-PAGE (4-12%) and Western blotting with streptavidin-peroxidase.

The results in FIG. 24 show that the BDCA-3-specific mAb AD5-14H12 specifically immunoprecipitates a cell surface protein of about 100 kD from HD-MY-Z cells. Thus, BDCA-3 has an apparent molecular weight of 100 kD.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended claims.

The invention claimed is:

1. A method for isolating or enriching for dendritic cells from a mixture of human cells:
   a) obtaining a mixture of human cells;
   b) contacting cells in the mixture with an antibody that binds BDCA-4, or antigen-binding fragment thereof, under conditions in which the antibody or antigen-binding fragment labels BDCA-4+ dendritic cells; and
   c) separating dendritic cells bound by the antibody or antigen-binding fragment from other cells in the mixture:
   wherein the mixture of human cells is obtained from bone marrow, peripheral blood, cell culture, umbilical cord blood, tonsil, lymph node, nasal membrane, spleen, skin, airway epithelia, lung, liver, gut, thymus,or Peyers patches.

2. The method of claim 1 wherein the dendritic cells are separated by immunomagnetic cell sorting.

3. The method of claim 1 wherein the dendritic cells are separated by flow cytometry.

4. The method of claim 1, wherein the mixture of human cells is obtained from bone marrow, from peripheral blood, or from cell culture.

5. The method of claim 1 wherein the mixture of human cells is obtained by leukopheresis of peripheral blood.

6. The method of claim 1 wherein the mixture of human cells is from a source selected from umbilical cord blood, tonsil, lymph node, nasal membrane, spleen, skin, airway epithelia, lung, liver, gut, spleen, thymus, and Peyers patches.

7. The method of claim 1, further comprising treating the cells with an agent that modulates dendritic cell cytokine production.

8. The method of claim 4, wherein the mixture of human cells is obtained from peripheral blood.

9. A method for isolating or enriching for human dendritic cells:
   a) obtaining human cells from a one or more human hematopoietic tissues, one or more human non-hematopoietic tissues, or both;
   b) contacting cells with an antibody that binds BDCA-4, or antigen-binding fragment thereof, under conditions in which the antibody or antigen-binding fragment labels BDCA-4+ dendritic cells; and
   c) separating dendritic cells bound by the antibody or antigen-binding fragment thereof from cells that are not bound by the antibody or antigen-binding site.

10. The method of claim 9 wherein the dendritic cells are separated by immunomagnetic cell sorting.

11. The method of claim 9 wherein the dendritic cells are separated by flow cytometry.

12. The method of claim 9, wherein the human cells are obtained from bone marrow or from peripheral blood.

13. The method of claim 9 wherein the human cells are obtained by leukopheresis of peripheral blood.

14. The method of claim 9 wherein the human cells are from a source selected from umbilical cord blood, tonsil, lymph node, nasal membrane, skin, airway epithelia, lung, liver, gut, spleen, thymus, and Peyers patches.

15. The method of claim 9, further comprising treating the dendritic cells with an agent that modulates dendritic cell cytokine production.

16. The method of claim 15, wherein the human cells are obtained from peripheral blood.

17. A method for isolating or enriching for human dendritic cells:
   a) obtaining cultured human cells comprising dendritic cells;
   b) contacting the cells with an antibody that binds BDCA-4, or antigen-binding fragment thereof, under conditions in which the antibody or antigen-binding fragment labels BDCA-4+ dendritic cells; and
   c) separating dendritic cells bound by the antibody or antigen-binding fragment thereof from cells that are not bound by the antibody or antigen-binding fragment thereof.

* * * * *

SEQUENCE LISTING

```
<160> NUMBER OF SEQ ID NOS: 38

<210> SEQ ID NO 1
<211> LENGTH: 1312
<212> TYPE: DNA
<213> ORGANISM: Homo sapiens
<220> FEATURE:
<221> NAME/KEY: misc_feature
<222> LOCATION: (1)..(1312)
<223> OTHER INFORMATION: BDCA-2 cDNA sequence
```

<400> SEQUENCE: 1

```
cagtgattct cgtgcctcag cctcctgagt agccgaaatt acagacgtgt gccaccatgc    60
ttggctaatt ttttggattt ttagtagaga tggggtttca ctatgttggc caggctagtc   120
ttgaactcct ggcctgaagc aatccgccca cctcagcctc ccaaagtgct gagattatag   180
gcacgagcca ctacacctgg ccacaaaatt ctttaaagaa gccaatccca tcctccctca   240
agagccaagg ggccacctca ccctcttgtt acagcagatc ctgcctccac agtcaccctg   300
ctcccaagtg caacctctgt ctgaccctgc atggtgtgcg gtgccctcct gcctcaggcc   360
gcgaagaagg atctaagggc ttggcttgtt tgaaagaacc acaccccgaa agtaacatct   420
ttggagaaag tgatacaaga gcttctgcac ccacctgata gaggaagtcc aaagggtgtg   480
cgcacacaca atggtgcctg aagaagagcc tcaagaccga gagaaaggac tctggtggtt   540
ccagttgaag gtctggtcca tgcagtcgt atccatcttg ctcctcagtg tctgtttcac   600
tgtgagttct gtggtgcctc acaatttat gtatagcaaa actgtcaaga ggctgtccaa   660
gttacgagag tatcaacagt atcatccaag cctgacctgc gtcatggaag gaaaggacat   720
agaagattgg agctgctgcc caaccccttg gacttcattt cagtctagtt gctactttat   780
ttctactggg atgcaatctt ggactaagag tcaaaagaac tgttctgtga tggggctga   840
tctggtggtg atcaacacca gggaagaaca ggatttcatc attcagaatc tgaaaagaaa   900
ttcttcttat tttctggggc tgtcagatcc aggggtcgg cgacattggc aatgggttga   960
ccagacacca taatgaaaa atgtcacatt ctggcactca ggtgaaccca ataaccttga  1020
tgagcgttgt gcgataataa atttccgttc ttcagaagaa tggggctgga atgacattca  1080
ctgtcatgta cctcagaagt caatttgcaa gatgaagaag atctacatat aaatgaaata  1140
ttctccctgg aaatgtgttt gggttggcat ccaccgttgt agaaagctaa attgatttt   1200
taatttatgt gtaagttttg tacaaggaat gcccctaaaa tgtttcagca ggctgtcacc  1260
tattacactt atgatataat ccaaaaaaaa aaaaaaaaaa aaaaaaaaaa aa          1312
```

<210> SEQ ID NO 2
<211> LENGTH: 213
<212> TYPE: PRT
<213> ORGANISM: Homo sapiens
<220> FEATURE:
<221> NAME/KEY: UNSURE
<222> LOCATION: (1)..(213)
<223> OTHER INFORMATION: amino acid sequence of one of the isoforms of
      BDCA-2 with all six exons expressed

<400> SEQUENCE: 2

```
Met Val Pro Glu Glu Pro Gln Asp Arg Glu Lys Gly Leu Trp Trp
1               5                  10                  15

Phe Gln Leu Lys Val Trp Ser Met Ala Val Val Ser Ile Leu Leu
                20                  25                  30

Ser Val Cys Phe Thr Val Ser Ser Val Val Pro His Asn Phe Met Tyr
                35                  40                  45

Ser Lys Thr Val Lys Arg Leu Ser Lys Leu Arg Glu Tyr Gln Gln Tyr
            50                  55                  60

His Pro Ser Leu Thr Cys Val Met Glu Gly Lys Asp Ile Glu Asp Trp
65                  70                  75                  80

Ser Cys Cys Pro Thr Pro Trp Thr Ser Phe Gln Ser Ser Cys Tyr Phe
                    85                  90                  95

Ile Ser Thr Gly Met Gln Ser Trp Thr Lys Ser Gln Lys Asn Cys Ser
                100                 105                 110
```

```
            Val Met Gly Ala Asp Leu Val Val Ile Asn Thr Arg Glu Glu Gln Asp
                115                 120                 125

Phe Ile Ile Gln Asn Leu Lys Arg Asn Ser Ser Tyr Phe Leu Gly Leu
    130                 135                 140

Ser Asp Pro Gly Gly Arg Arg His Trp Gln Trp Val Asp Gln Thr Pro
145                 150                 155                 160

Tyr Asn Glu Asn Val Thr Phe Trp His Ser Gly Glu Pro Asn Asn Leu
                165                 170                 175

Asp Glu Arg Cys Ala Ile Ile Asn Phe Arg Ser Ser Glu Glu Trp Gly
                180                 185                 190

Trp Asn Asp Ile His Cys His Val Pro Gln Lys Ser Ile Cys Lys Met
                195                 200                 205

Lys Lys Ile Tyr Ile
        210

<210> SEQ ID NO 3
<211> LENGTH: 1227
<212> TYPE: DNA
<213> ORGANISM: Mus musculus
<220> FEATURE:
<221> NAME/KEY: CDS
<222> LOCATION: (146)..(775)
<223> OTHER INFORMATION: coding sequence of mouse Dectin-2
<300> PUBLICATION INFORMATION:
<308> DATABASE ACCESSION NUMBER: AF240357
<309> DATABASE ENTRY DATE: 2000-05-02
<313> RELEVANT RESIDUES: (1)..(1227)

<400> SEQUENCE: 3
```

| | |
|---|---|
| cattggcccg ctctgtggca tttaactcaa gtgtgtgtgg aagttgattc tgaactctgg | 60 |
| cctctttgac agaagccagg tccctgagtc gtattttgga gacagatgca agaaaccccct | 120 |
| gaccttctga acatacacct caaca atg gtg cag gaa aga caa tcc caa ggg | 172 |
|                                         Met Val Gln Glu Arg Gln Ser Gln Gly<br>                                       1                5 | |
| aag gga gtc tgc tgg acc ctg aga ctc tgg tca gct gct gtg att tcc<br>Lys Gly Val Cys Trp Thr Leu Arg Leu Trp Ser Ala Ala Val Ile Ser<br> 10               15                   20                   25 | 220 |
| atg tta ctc ttg agt acc tgt ttc att gcg agc tgt gtg gtg act tac<br>Met Leu Leu Leu Ser Thr Cys Phe Ile Ala Ser Cys Val Val Thr Tyr<br>               30                   35                   40 | 268 |
| caa ttt att atg gac cag ccc agt aga aga cta tat gaa ctt cac aca<br>Gln Phe Ile Met Asp Gln Pro Ser Arg Arg Leu Tyr Glu Leu His Thr<br>               45                   50                   55 | 316 |
| tac cat tcc agt ctc acc tgc ttc agt gaa ggg act atg gtg tca gaa<br>Tyr His Ser Ser Leu Thr Cys Phe Ser Glu Gly Thr Met Val Ser Glu<br>        60                   65                   70 | 364 |
| aaa atg tgg gga tgc tgc cca aat cac tgg aag tca ttt ggc tcc agc<br>Lys Met Trp Gly Cys Cys Pro Asn His Trp Lys Ser Phe Gly Ser Ser<br>75                   80                   85 | 412 |
| tgc tac ctc att tct acc aag gag aac ttc tgg agc acc agt gag cag<br>Cys Tyr Leu Ile Ser Thr Lys Glu Asn Phe Trp Ser Thr Ser Glu Gln<br> 90               95                  100              105 | 460 |
| aac tgt gtt cag atg ggg gct cat ctg gtg gtg atc aat act gaa gcg<br>Asn Cys Val Gln Met Gly Ala His Leu Val Val Ile Asn Thr Glu Ala<br>                     110                 115                 120 | 508 |
| gag cag aat ttc atc acc cag cag ctg aat gag tca ctt tct tac ttc<br>Glu Gln Asn Phe Ile Thr Gln Gln Leu Asn Glu Ser Leu Ser Tyr Phe<br>              125                   130                 135 | 556 |
| ctg ggt ctt tcg gat cca caa ggt aat ggc aaa tgg caa tgg atc gat<br>Leu Gly Leu Ser Asp Pro Gln Gly Asn Gly Lys Trp Gln Trp Ile Asp<br>              140                   145                 150 | 604 |

```
gat act cct ttc agt caa aat gtc agg ttc tgg cac ccc cat gaa ccc      652
Asp Thr Pro Phe Ser Gln Asn Val Arg Phe Trp His Pro His Glu Pro
    155                 160                 165 aat ctt cca gaa gag cgg tgt gtt tca ata gtt tac tgg aat cct tcg      700
Asn Leu Pro Glu Glu Arg Cys Val Ser Ile Val Tyr Trp Asn Pro Ser
170                 175                 180                 185 aaa tgg ggc tgg aat gat gtt ttc tgt gat agt aaa cac aat tca ata      748
Lys Trp Gly Trp Asn Asp Val Phe Cys Asp Ser Lys His Asn Ser Ile
                    190                 195                 200 tgt gaa atg aag aag att tac cta tga gtgcctgtta ttcattaata            795
Cys Glu Met Lys Lys Ile Tyr Leu
                205 tctttaaagt tcagacctac caagaagcca taacttcttg gcctgtacat ctgacagagg    855 ccgttctttt cctagccact attcttact caaacagaat gagcccttc tccttctgat      915 ggttagagtt ttgtcaactt gacacaaact agagtcacct ggggagtagg atcttcagct    975 aaggaattgc ctctgtcagc ttgaccagtc agcatgtctg ggggcatttt cttgattaat   1035 gattgttgta agagggtcca ggtggtaagc aaaggtgtta aacccatgaa gagcaagcca   1095 gggagcatca tccatccatc tctgccctca ggtttctgcc ccagggtctt gcctggttt    1155 ctttctatga actgctgtta cttgaaagta taagatgaat aaacaatttc atccaaaaaa   1215 aaaaaaaaaa aa                                                        1227

<210> SEQ ID NO 4
<211> LENGTH: 209
<212> TYPE: PRT
<213> ORGANISM: Mus musculus

<400> SEQUENCE: 4

Met Val Gln Glu Arg Gln Ser Gln Gly Lys Gly Val Cys Trp Thr Leu
1               5                   10                  15

Arg Leu Trp Ser Ala Ala Val Ile Ser Met Leu Leu Ser Thr Cys
            20                  25                  30

Phe Ile Ala Ser Cys Val Val Thr Tyr Gln Phe Ile Met Asp Gln Pro
        35                  40                  45

Ser Arg Arg Leu Tyr Glu Leu His Thr Tyr His Ser Ser Leu Thr Cys
    50                  55                  60

Phe Ser Glu Gly Thr Met Val Ser Glu Lys Met Trp Gly Cys Cys Pro
65                  70                  75                  80

Asn His Trp Lys Ser Phe Gly Ser Ser Cys Tyr Leu Ile Ser Thr Lys
                85                  90                  95

Glu Asn Phe Trp Ser Thr Ser Glu Gln Asn Cys Val Gln Met Gly Ala
            100                 105                 110

His Leu Val Val Ile Asn Thr Glu Ala Glu Gln Asn Phe Ile Thr Gln
        115                 120                 125

Gln Leu Asn Glu Ser Leu Ser Tyr Phe Leu Gly Leu Ser Asp Pro Gln
    130                 135                 140

Gly Asn Gly Lys Trp Gln Trp Ile Asp Asp Thr Pro Phe Ser Gln Asn
145                 150                 155                 160

Val Arg Phe Trp His Pro His Glu Pro Asn Leu Pro Glu Glu Arg Cys
                165                 170                 175

Val Ser Ile Val Tyr Trp Asn Pro Ser Lys Trp Gly Trp Asn Asp Val
            180                 185                 190

Phe Cys Asp Ser Lys His Asn Ser Ile Cys Glu Met Lys Lys Ile Tyr
        195                 200                 205
```

Leu

<210> SEQ ID NO 5
<211> LENGTH: 237
<212> TYPE: PRT
<213> ORGANISM: Homo sapiens
<220> FEATURE:
<221> NAME/KEY: UNSURE
<222> LOCATION: (1)..(237)
<223> OTHER INFORMATION: amino acid sequence of human DCIR
<300> PUBLICATION INFORMATION:
<308> DATABASE ACCESSION NUMBER: AJ133532
<309> DATABASE ENTRY DATE: 1999-09-01
<313> RELEVANT RESIDUES: (1)..(237)

<400> SEQUENCE: 5

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ala Ser Lys Glu Arg
            20                  25                  30

Thr Ala Pro His Lys Ser Asn Thr Gly Phe Pro Lys Leu Leu Cys Ala
        35                  40                  45

Ser Leu Leu Ile Phe Phe Leu Leu Leu Ala Ile Ser Phe Phe Ile Ala
    50                  55                  60

Phe Val Ile Phe Phe Gln Lys Tyr Ser Gln Leu Leu Glu Lys Lys Thr
65                  70                  75                  80

Thr Lys Glu Leu Val His Thr Thr Leu Glu Cys Val Lys Lys Asn Met
                85                  90                  95

Pro Val Glu Glu Thr Ala Trp Ser Cys Cys Pro Lys Asn Trp Lys Ser
            100                 105                 110

Phe Ser Ser Asn Cys Tyr Phe Ile Ser Thr Glu Ser Ala Ser Trp Gln
        115                 120                 125

Asp Ser Glu Lys Asp Cys Ala Arg Met Glu Ala His Leu Leu Val Ile
    130                 135                 140

Asn Thr Gln Glu Glu Gln Asp Phe Ile Phe Gln Asn Leu Gln Glu Glu
145                 150                 155                 160

Ser Ala Tyr Phe Val Gly Leu Ser Asp Pro Glu Gly Gln Arg His Trp
                165                 170                 175

Gln Trp Val Asp Gln Thr Pro Tyr Asn Glu Ser Ser Thr Phe Trp His
            180                 185                 190

Pro Arg Glu Pro Ser Asp Pro Asn Glu Arg Cys Val Val Leu Asn Phe
        195                 200                 205

Arg Lys Ser Pro Lys Arg Trp Gly Trp Asn Asp Val Asn Cys Leu Gly
    210                 215                 220

Pro Gln Arg Ser Val Cys Glu Met Met Lys Ile His Leu
225                 230                 235

<210> SEQ ID NO 6
<211> LENGTH: 5
<212> TYPE: PRT
<213> ORGANISM: Artificial Sequence
<220> FEATURE:
<223> OTHER INFORMATION: basic unit of a linking peptide

<400> SEQUENCE: 6

Gly Gly Gly Gly Ser
1               5

<210> SEQ ID NO 7
<211> LENGTH: 24
<212> TYPE: DNA

```
<213> ORGANISM: Artificial Sequence
<220> FEATURE:
<223> OTHER INFORMATION: primer

<400> SEQUENCE: 7
ttgaaagaac cacaccccga aagt                                              24

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
tagctttcta caacggtgga tgcc                                              24

<210> SEQ ID NO 9
<211> LENGTH: 4
<212> TYPE: PRT
<213> ORGANISM: Homo sapiens

<400> SEQUENCE: 9

Asn Cys Ser Val
1

<210> SEQ ID NO 10
<211> LENGTH: 4
<212> TYPE: PRT
<213> ORGANISM: Homo sapiens

<400> SEQUENCE: 10

Asn Ser Ser Tyr
1

<210> SEQ ID NO 11
<211> LENGTH: 4
<212> TYPE: PRT
<213> ORGANISM: Homo sapiens

<400> SEQUENCE: 11

Asn Val Thr Phe
1

<210> SEQ ID NO 12
<211> LENGTH: 4
<212> TYPE: PRT
<213> ORGANISM: Mus musculus

<400> SEQUENCE: 12

Asn Glu Ser Leu
1

<210> SEQ ID NO 13
<211> LENGTH: 4
<212> TYPE: PRT
<213> ORGANISM: Homo sapiens

<400> SEQUENCE: 13

Asn Glu Ser Ser
1

<210> SEQ ID NO 14
<211> LENGTH: 4
<212> TYPE: PRT
<213> ORGANISM: Homo sapiens
```

```
<400> SEQUENCE: 14

Lys Arg Leu Ser
1

<210> SEQ ID NO 15
<211> LENGTH: 4
<212> TYPE: PRT
<213> ORGANISM: Homo sapiens

<400> SEQUENCE: 15

Lys Lys Thr Thr
1

<210> SEQ ID NO 16
<211> LENGTH: 4
<212> TYPE: PRT
<213> ORGANISM: Homo sapiens

<400> SEQUENCE: 16

Thr Arg Glu Glu
1

<210> SEQ ID NO 17
<211> LENGTH: 4
<212> TYPE: PRT
<213> ORGANISM: Homo sapiens

<400> SEQUENCE: 17

Ser Ser Glu Glu
1

<210> SEQ ID NO 18
<211> LENGTH: 4
<212> TYPE: PRT
<213> ORGANISM: Mus musculus

<400> SEQUENCE: 18

Ser Thr Lys Glu
1

<210> SEQ ID NO 19
<211> LENGTH: 4
<212> TYPE: PRT
<213> ORGANISM: Mus musculus

<400> SEQUENCE: 19

Ser Thr Ser Glu
1

<210> SEQ ID NO 20
<211> LENGTH: 4
<212> TYPE: PRT
<213> ORGANISM: Mus musculus

<400> SEQUENCE: 20

Thr Glu Ala Glu
1

<210> SEQ ID NO 21
<211> LENGTH: 4
<212> TYPE: PRT
<213> ORGANISM: Mus musculus

<400> SEQUENCE: 21
```

```
Ser Ile Cys Glu
1

<210> SEQ ID NO 22
<211> LENGTH: 4
<212> TYPE: PRT
<213> ORGANISM: Homo sapiens

<400> SEQUENCE: 22

Thr Tyr Ala Glu
1

<210> SEQ ID NO 23
<211> LENGTH: 4
<212> TYPE: PRT
<213> ORGANISM: Homo sapiens

<400> SEQUENCE: 23

Thr Thr Lys Glu
1

<210> SEQ ID NO 24
<211> LENGTH: 4
<212> TYPE: PRT
<213> ORGANISM: Homo sapiens

<400> SEQUENCE: 24

Thr Thr Leu Glu
1

<210> SEQ ID NO 25
<211> LENGTH: 4
<212> TYPE: PRT
<213> ORGANISM: Homo sapiens

<400> SEQUENCE: 25

Ser Trp Gln Asp
1

<210> SEQ ID NO 26
<211> LENGTH: 4
<212> TYPE: PRT
<213> ORGANISM: Homo sapiens

<400> SEQUENCE: 26

Ser Glu Lys Asp
1

<210> SEQ ID NO 27
<211> LENGTH: 4
<212> TYPE: PRT
<213> ORGANISM: Homo sapiens

<400> SEQUENCE: 27

Thr Gln Glu Glu
1

<210> SEQ ID NO 28
<211> LENGTH: 8
<212> TYPE: PRT
<213> ORGANISM: Homo sapiens
<220> FEATURE:
<221> NAME/KEY: UNSURE
<222> LOCATION: (1)..(8)
<223> OTHER INFORMATION: Tyrosine kinase phosphorylation site in human
      BDCA-2
```

```
<400> SEQUENCE: 28

Lys Leu Arg Glu Tyr Gln Gln Tyr
1               5

<210> SEQ ID NO 29
<211> LENGTH: 4
<212> TYPE: PRT
<213> ORGANISM: Homo sapiens

<400> SEQUENCE: 29

Ser Val Cys Glu
1

<210> SEQ ID NO 30
<211> LENGTH: 4
<212> TYPE: PRT
<213> ORGANISM: Homo sapiens

<400> SEQUENCE: 30

Ser Val Cys Glu
1

<210> SEQ ID NO 31
<211> LENGTH: 9
<212> TYPE: PRT
<213> ORGANISM: Mus musculus
<220> FEATURE:
<221> NAME/KEY: UNSURE
<222> LOCATION: (1)..(9)
<223> OTHER INFORMATION: Tyrosine kinase phosphorylation site in mouse
      dectin-2

<400> SEQUENCE: 31

Arg Arg Leu Tyr Glu Leu His Thr Tyr
1               5

<210> SEQ ID NO 32
<211> LENGTH: 4
<212> TYPE: PRT
<213> ORGANISM: Homo sapiens

<400> SEQUENCE: 32

Gly Gly Arg Arg
1

<210> SEQ ID NO 33
<211> LENGTH: 6
<212> TYPE: PRT
<213> ORGANISM: Mus musculus
<220> FEATURE:
<221> NAME/KEY: UNSURE
<222> LOCATION: (1)..(6)
<223> OTHER INFORMATION: N-myristylation site in mouse dectin-2

<400> SEQUENCE: 33

Gly Val Cys Trp Thr Leu
1               5

<210> SEQ ID NO 34
<211> LENGTH: 6
<212> TYPE: PRT
<213> ORGANISM: Mus musculus
<220> FEATURE:
<221> NAME/KEY: UNSURE
<222> LOCATION: (1)..(6)
<223> OTHER INFORMATION: N-myristylation site in mouse dectin-2

<400> SEQUENCE: 34
```

```
Gly Thr Met Val Ser Glu
1               5

<210> SEQ ID NO 35
<211> LENGTH: 6
<212> TYPE: PRT
<213> ORGANISM: Mus musculus
<220> FEATURE:
<221> NAME/KEY: UNSURE
<222> LOCATION: (1)..(6)
<223> OTHER INFORMATION: N-myristylation site in mouse dectin-2

<400> SEQUENCE: 35

Gly Cys Cys Pro Asn His
1               5

<210> SEQ ID NO 36
<211> LENGTH: 6
<212> TYPE: PRT
<213> ORGANISM: Homo sapiens
<220> FEATURE:
<221> NAME/KEY: UNSURE
<222> LOCATION: (1)..(6)
<223> OTHER INFORMATION: N-myristylation site in human DCIR

<400> SEQUENCE: 36

Gly Ile Asn Thr Ala Ser
1               5

<210> SEQ ID NO 37
<211> LENGTH: 6
<212> TYPE: PRT
<213> ORGANISM: Unknown
<220> FEATURE:
<223> OTHER INFORMATION: consensus ITIM motif
<220> FEATURE:
<221> NAME/KEY: misc_feature
<222> LOCATION: (2)..(5)
<223> OTHER INFORMATION: consensus immunoreceptor tyrosine-based
      inhibitory motif (ITIM motif) (I/V)XYXX(L/V), amino acid "X" from
      position 2, 4 and 5 can be any amino acid
<220> FEATURE:
<221> NAME/KEY: misc_feature
<222> LOCATION: (1)..(1)
<223> OTHER INFORMATION: amino acid "X" at position 1 can be either
      amino acid "I " or "V"
<220> FEATURE:
<221> NAME/KEY: misc_feature
<222> LOCATION: (6)..(6)
<223> OTHER INFORMATION: amino acid "X" at position 6 can be either
      amino acid "L " or "V"

<400> SEQUENCE: 37

Xaa Xaa Tyr Xaa Xaa Xaa
1               5

<210> SEQ ID NO 38
<211> LENGTH: 6
<212> TYPE: PRT
<213> ORGANISM: Homo sapiens
<220> FEATURE:
<221> NAME/KEY: UNSURE
<222> LOCATION: (1)..(6)
<223> OTHER INFORMATION: immunoreceptor tyrosine-based inhibitory motif
      (ITIM motif) in DCIR

<400> SEQUENCE: 38

Ile Thr Tyr Ala Glu Val
1               5
```